United States Patent
Caffes et al.

(10) Patent No.: US 10,588,620 B2
(45) Date of Patent: Mar. 17, 2020

(54) DEVICE FOR SUTURE ATTACHMENT FOR MINIMALLY INVASIVE HEART VALVE REPAIR

(71) Applicant: NeoChord, Inc., St. Louis Park, MN (US)

(72) Inventors: Levi Caffes, Denver, CO (US); Joel Helgerson, Erie, CO (US); Andrew Schifle, Superior, CO (US); Daryl Edmiston, Draper, UT (US)

(73) Assignee: NeoChord, Inc., St. Louis Park, MN (US)

( * ) Notice: Subject to any disclaimer, the term of this patent is extended or adjusted under 35 U.S.C. 154(b) by 0 days.

(21) Appl. No.: 16/363,701

(22) Filed: Mar. 25, 2019

(65) Prior Publication Data

US 2019/0290260 A1    Sep. 26, 2019

Related U.S. Application Data

(60) Provisional application No. 62/647,162, filed on Mar. 23, 2018, provisional application No. 62/728,349, filed on Sep. 7, 2018.

(51) Int. Cl.
  *A61B 17/04*    (2006.01)
  *A61B 17/06*    (2006.01)
  (Continued)

(52) U.S. Cl.
  CPC .... *A61B 17/0469* (2013.01); *A61B 17/00234* (2013.01); *A61B 17/06* (2013.01);
  (Continued)

(58) Field of Classification Search
  CPC ................................................. A61B 17/0482
  (Continued)

(56) References Cited

U.S. PATENT DOCUMENTS

| 2,751,908 A | 6/1956 | Wallace |
| 3,664,330 A | 5/1972 | Deutsch |

(Continued)

FOREIGN PATENT DOCUMENTS

| EP | 1039851 B1 | 7/2005 |
| EP | 1637091 A2 | 3/2006 |

(Continued)

OTHER PUBLICATIONS

Interactive Cardio Vascular and Thoracic Surgery; Abstracts; Suppl 3 to vol. 7 (Sep. 2008) 52 pages.
(Continued)

*Primary Examiner* — Martin T Ton
(74) *Attorney, Agent, or Firm* — Patterson Thuente Pederson, P.A.

(57) ABSTRACT

In one embodiment, a suture attachment catheter configured to repair a heart valve by inserting a suture in a valve leaflet of a beating heart of a patient includes a handle control, a flexible catheter body, and a suture attachment assembly at a distal end of the catheter body. The suture attachment assembly can include a rail between a distal clamping jaw hingedly attached to the rail, and a proximal clamping jaw. One of the proximal clamping jaw or distal clamping jaw can be selectively slideable with respect to the other on the rail using a jaw actuator of the control handle to adjust a distance between the proximal clamping jaw and the distal clamping jaw. A needle can be selectively slideable within the catheter body by using a needle actuator of the proximal handle control to penetrate a valve leaflet and insert a suture through the valve leaflet when the valve leaflet is captured between the proximal clamping jaw and the distal clamping jaw.

19 Claims, 39 Drawing Sheets

(51) Int. Cl.
*A61B 17/00* (2006.01)
*A61M 25/00* (2006.01)
*A61F 2/24* (2006.01)

(52) U.S. Cl.
CPC ... *A61B 2017/00243* (2013.01); *A61F 2/2457* (2013.01); *A61M 25/0082* (2013.01)

(58) Field of Classification Search
USPC .......................................................... 606/139
See application file for complete search history.

(56) References Cited

U.S. PATENT DOCUMENTS

| | | | |
|---|---|---|---|
| 3,667,474 A | 6/1972 | Lapkin | |
| 3,842,840 A | 10/1974 | Schweizer | |
| 4,258,716 A | 3/1981 | Sutherland | |
| 4,351,345 A | 9/1982 | Carney | |
| 4,759,348 A | 7/1988 | Cawood | |
| 4,836,204 A | 6/1989 | Landymore et al. | |
| 4,935,027 A | 6/1990 | Yoon | |
| 4,957,498 A | 9/1990 | Caspari | |
| 4,967,498 A | 9/1990 | Caspari | |
| 4,960,424 A | 10/1990 | Grooters | |
| 4,967,798 A | 11/1990 | Hammer | |
| 4,972,874 A | 11/1990 | Jackson | |
| 5,053,013 A | 10/1991 | Ensminger | |
| 5,059,201 A | 10/1991 | Asnis | |
| 5,211,650 A | 5/1993 | Noda | |
| 5,297,536 A | 3/1994 | Wilk | |
| 5,304,185 A | 4/1994 | Taylor | |
| 5,312,423 A | 5/1994 | Rosenbluth et al. | |
| 5,336,229 A | 8/1994 | Noda | |
| 5,383,877 A | 1/1995 | Clarke | |
| 5,431,666 A | 7/1995 | Sauer et al. | |
| 5,452,733 A | 9/1995 | Sterman | |
| 5,474,519 A | 12/1995 | Bloomer | |
| 5,547,455 A | 8/1996 | McKenna et al. | |
| 5,556,411 A | 9/1996 | Tasoda et al. | |
| 5,571,215 A | 11/1996 | Sterman | |
| 5,601,578 A | 2/1997 | Murphy | |
| 5,626,607 A | 5/1997 | Malecki | |
| 5,653,716 A | 8/1997 | Malo et al. | |
| 5,665,100 A | 9/1997 | Yoon | |
| 5,667,472 A | 9/1997 | Finn et al. | |
| 5,667,473 A | 9/1997 | Finn et al. | |
| 5,667,478 A | 9/1997 | McFarlin et al. | |
| 5,693,091 A | 12/1997 | Larson, Jr. et al. | |
| 5,728,113 A | 3/1998 | Sherts | |
| 5,762,458 A | 6/1998 | Wang et al. | |
| 5,762,613 A | 6/1998 | Sutton et al. | |
| 5,766,163 A | 6/1998 | Mueller et al. | |
| 5,769,791 A | 6/1998 | Benaron et al. | |
| 5,772,597 A | 6/1998 | Goldberger et al. | |
| 5,772,672 A | 6/1998 | Toy et al. | |
| 5,785,658 A | 7/1998 | Benaron et al. | |
| 5,797,960 A | 8/1998 | Stevens et al. | |
| 5,830,231 A | 11/1998 | Geiges, Jr. | |
| 5,839,639 A | 11/1998 | Sauer et al. | |
| 5,857,961 A | 1/1999 | Vanden Hoek et al. | |
| 5,897,564 A | 4/1999 | Schulze et al. | |
| 5,908,428 A | 6/1999 | Scirica et al. | |
| 5,908,429 A | 6/1999 | Yoon | |
| 5,919,128 A | 7/1999 | Fitch | |
| 5,961,440 A | 10/1999 | Schweich, Jr. | |
| 5,972,004 A | 10/1999 | Williamson et al. | |
| 5,972,030 A | 10/1999 | Garrison et al. | |
| 5,984,939 A | 11/1999 | Yoon | |
| 5,993,466 A | 11/1999 | Yoon | |
| 5,993,467 A | 11/1999 | Yoon | |
| 6,022,360 A | 2/2000 | Reimels et al. | |
| 6,045,497 A | 4/2000 | Schweich, Jr. | |
| 6,050,936 A | 4/2000 | Schweich, Jr. | |
| 6,053,933 A | 4/2000 | Balazs et al. | |
| 6,059,715 A | 5/2000 | Schweich, Jr. | |
| 6,077,214 A | 6/2000 | Mortier et al. | |
| 6,117,144 A | 9/2000 | Nobles et al. | |
| 6,129,683 A | 10/2000 | Sutton et al. | |
| 6,149,660 A | 11/2000 | Laufer et al. | |
| 6,152,934 A | 11/2000 | Harper et al. | |
| 6,162,168 A | 12/2000 | Schweich, Jr. | |
| 6,162,233 A | 12/2000 | Williamson | |
| 6,165,119 A | 12/2000 | Schweich, Jr. | |
| 6,165,120 A | 12/2000 | Schweich, Jr. | |
| 6,165,183 A | 12/2000 | Kuehn et al. | |
| 6,178,346 B1 | 1/2001 | Amundson et al. | |
| 6,179,195 B1 * | 1/2001 | Adams ............ A61B 17/07207 227/179.1 | |
| 6,183,411 B1 | 2/2001 | Mortier et al. | |
| 6,190,357 B1 | 2/2001 | Ferrari et al. | |
| 6,234,079 B1 | 5/2001 | Chdetkow | |
| 6,234,995 B1 | 5/2001 | Peacock, III | |
| 6,245,079 B1 | 6/2001 | Nobles et al. | |
| 6,260,552 B1 | 7/2001 | Mortier et al. | |
| 6,261,222 B1 | 7/2001 | Schweich, Jr. | |
| 6,264,602 B1 | 7/2001 | Mortier et al. | |
| 6,269,819 B1 | 8/2001 | Oz et al. | |
| 6,270,508 B1 | 8/2001 | Klieman et al. | |
| 6,283,993 B1 | 9/2001 | Cosgrove et al. | |
| 6,312,447 B1 | 11/2001 | Grimes | |
| 6,332,863 B1 | 12/2001 | Schweich, Jr. et al. | |
| 6,332,864 B1 | 12/2001 | Schweich, Jr. et al. | |
| 6,332,893 B1 | 12/2001 | Mortier et al. | |
| 6,355,050 B1 | 3/2002 | Andreas et al. | |
| 6,401,720 B1 | 6/2002 | Stevens et al. | |
| 6,402,679 B1 | 6/2002 | Mortier et al. | |
| 6,402,680 B2 | 6/2002 | Mortier et al. | |
| 6,402,781 B1 | 6/2002 | Langberg et al. | |
| 6,406,420 B1 | 6/2002 | McCarthy et al. | |
| 6,419,626 B1 | 7/2002 | Yoon | |
| 6,436,107 B1 | 8/2002 | Wang et al. | |
| 6,443,922 B1 | 9/2002 | Roberts et al. | |
| 6,451,054 B1 | 9/2002 | Stevens | |
| 6,461,366 B1 | 10/2002 | Seguin | |
| 6,508,777 B1 | 1/2003 | Macoviak et al. | |
| 6,514,194 B2 | 2/2003 | Schweich, Jr. et al. | |
| 6,533,796 B1 | 3/2003 | Sauer et al. | |
| 6,537,198 B1 | 3/2003 | Vidlund et al. | |
| 6,537,314 B2 | 3/2003 | Langberg et al. | |
| 6,551,331 B2 | 4/2003 | Nobles et al. | |
| 6,558,416 B2 | 5/2003 | Cosgrove et al. | |
| 6,562,052 B2 | 5/2003 | Nobles et al. | |
| 6,564,805 B2 | 5/2003 | Garrison et al. | |
| 6,582,388 B1 | 6/2003 | Coleman et al. | |
| 6,585,727 B1 | 7/2003 | Cashman et al. | |
| 6,589,160 B2 | 7/2003 | Schweich, Jr. et al. | |
| 6,602,288 B1 | 8/2003 | Cosgrove et al. | |
| 6,616,684 B1 | 9/2003 | Vidlund et al. | |
| 6,619,291 B2 | 9/2003 | Hlavka et al. | |
| 6,622,730 B2 | 9/2003 | Ekvall et al. | |
| 6,626,917 B1 | 9/2003 | Craig | |
| 6,626,930 B1 | 9/2003 | Allen et al. | |
| 6,629,534 B1 | 10/2003 | St. Goar et al. | |
| 6,629,921 B1 | 10/2003 | Schweich, Jr. et al. | |
| 6,629,984 B1 | 10/2003 | Chan | |
| 6,645,205 B2 | 11/2003 | Ginn | |
| 6,679,268 B2 | 1/2004 | Stevens et al. | |
| 6,692,605 B2 | 2/2004 | Kerr et al. | |
| 6,695,866 B1 | 2/2004 | Kuehn et al. | |
| 6,709,456 B2 | 3/2004 | Langberg et al. | |
| 6,718,985 B2 | 4/2004 | Hlavka et al. | |
| 6,723,038 B1 | 4/2004 | Schroeder et al. | |
| 6,733,509 B2 | 5/2004 | Nobles et al. | |
| 6,740,107 B2 | 5/2004 | Loeb et al. | |
| 6,746,471 B2 | 6/2004 | Mortier et al. | |
| 6,752,713 B2 | 6/2004 | Johnson, Jr. | |
| 6,752,813 B2 | 6/2004 | Goldfarb et al. | |
| 6,755,777 B2 | 6/2004 | Schweich, Jr. et al. | |
| 6,764,510 B2 | 7/2004 | Vidlund et al. | |
| 6,770,083 B2 | 8/2004 | Seguin | |
| 6,770,084 B1 | 8/2004 | Bain et al. | |
| 6,793,618 B2 | 9/2004 | Schweich, Jr. et al. | |
| 6,802,860 B2 | 10/2004 | Cosgrove et al. | |
| 6,808,488 B2 | 10/2004 | Mortier et al. | |
| 6,810,882 B2 | 11/2004 | Langberg et al. | |

(56) References Cited

U.S. PATENT DOCUMENTS

| | | |
|---|---|---|
| 6,840,246 B2 | 1/2005 | Downing |
| 6,858,003 B2 | 2/2005 | Evans et al. |
| 6,875,224 B2 | 4/2005 | Grimes |
| 6,893,448 B2 | 5/2005 | O'Quinn et al. |
| 6,908,424 B2 | 6/2005 | Mortier et al. |
| 6,918,917 B1 | 7/2005 | Nguyen et al. |
| 6,921,407 B2 | 7/2005 | Nguyen et al. |
| 6,929,715 B2 | 8/2005 | Fladda et al. |
| 6,936,054 B2 | 8/2005 | Chu |
| 6,955,175 B2 | 10/2005 | Stevens et al. |
| 6,962,605 B2 | 11/2005 | Cosgrove et al. |
| 6,978,176 B2 | 12/2005 | Lattouf |
| 6,986,775 B2 | 1/2006 | Morales et al. |
| 6,989,028 B2 | 1/2006 | Lashinski et al. |
| 6,991,635 B2 | 1/2006 | Takamoto et al. |
| 6,997,950 B2 | 2/2006 | Chawla |
| 7,004,176 B2 | 2/2006 | Lau |
| 7,004,952 B2 | 2/2006 | Nobles et al. |
| 7,011,669 B2 | 3/2006 | Kimblad |
| 7,044,905 B2 | 5/2006 | Vidlund et al. |
| 7,048,754 B2 | 5/2006 | Martin et al. |
| 7,077,862 B2 | 7/2006 | Vidlund et al. |
| 7,083,628 B2 | 8/2006 | Bachman |
| 7,083,638 B2 | 8/2006 | Foerster |
| 7,090,686 B2 | 8/2006 | Nobles et al. |
| 7,094,244 B2 | 8/2006 | Schreck |
| 7,100,614 B2 | 9/2006 | Stevens et al. |
| 7,112,207 B2 | 9/2006 | Allen et al. |
| 7,112,219 B2 | 9/2006 | Vidlund et al. |
| 7,115,110 B2 | 10/2006 | Frazier et al. |
| 7,118,583 B2 | 10/2006 | O'Quinn et al. |
| 7,122,040 B2 | 10/2006 | Hill et al. |
| 7,179,291 B2 | 2/2007 | Rourke et al. |
| 7,186,264 B2 | 3/2007 | Liddicoat et al. |
| 7,189,199 B2 | 3/2007 | McCarthy et al. |
| 7,217,240 B2 | 5/2007 | Snow |
| 7,226,467 B2 | 6/2007 | Lucatero et al. |
| 7,247,134 B2 | 7/2007 | Vidlund et al. |
| 7,250,028 B2 | 7/2007 | Julian et al. |
| 7,288,097 B2 | 10/2007 | Seguin |
| 7,294,148 B2 | 11/2007 | McCarthy |
| 7,381,210 B2 | 6/2008 | Zarbatany et al. |
| 7,464,712 B2 | 12/2008 | Oz et al. |
| 7,563,267 B2 | 7/2009 | Goldfarb et al. |
| 7,563,273 B2 | 7/2009 | Goldfarb et al. |
| 7,604,646 B2 | 10/2009 | Goldfarb et al. |
| 7,608,091 B2 | 10/2009 | Goldfarb et al. |
| 7,635,386 B1 | 12/2009 | Gammie |
| 7,666,204 B2 | 2/2010 | Thornton et al. |
| 7,815,654 B2 | 10/2010 | Chu |
| 7,879,048 B2 | 2/2011 | Bain et al. |
| 7,887,552 B2 | 2/2011 | Bachman |
| 8,465,500 B2 | 6/2013 | Speziali |
| 8,545,551 B2 | 10/2013 | Loulmet |
| 8,758,393 B2 | 6/2014 | Zentgraf |
| 8,968,338 B2 | 3/2015 | Speziali |
| 9,044,221 B2 | 6/2015 | Zentgraf et al. |
| 9,192,374 B2 | 11/2015 | Zentgraf |
| 9,364,213 B2 | 6/2016 | Speziali |
| 9,700,300 B2 | 7/2017 | Speziali |
| 2001/0005787 A1 | 6/2001 | Oz |
| 2001/0016675 A1 | 8/2001 | Mortier et al. |
| 2001/0021872 A1 | 9/2001 | Bailey et al. |
| 2002/0013571 A1 | 1/2002 | Goldfarb et al. |
| 2002/0029080 A1 | 3/2002 | Mortier et al. |
| 2002/0049402 A1 | 4/2002 | Peacock, III |
| 2002/0077524 A1 | 6/2002 | Schweich, Jr. |
| 2002/0169359 A1 | 11/2002 | McCarthy |
| 2002/0173694 A1 | 11/2002 | Mortier et al. |
| 2002/0183766 A1 | 12/2002 | Seguin |
| 2003/0004562 A1 | 1/2003 | DiCarlo |
| 2003/0032979 A1 | 2/2003 | Mortier et al. |
| 2003/0050529 A1 | 3/2003 | Vidlund et al. |
| 2003/0050693 A1 | 3/2003 | Quijano |
| 2003/0078600 A1 | 4/2003 | O'Quinn et al. |
| 2003/0105519 A1 | 6/2003 | Fasol |
| 2003/0130731 A1 | 7/2003 | Vidlund et al. |
| 2003/0163029 A1 | 8/2003 | Sonnenschein et al. |
| 2003/0166992 A1 | 9/2003 | Schweich, Jr. |
| 2003/0167071 A1 | 9/2003 | Martin et al. |
| 2003/0171641 A1 | 9/2003 | Schweich, Jr. |
| 2003/0181928 A1 | 9/2003 | Vidlund et al. |
| 2003/0187457 A1 | 10/2003 | Weber |
| 2003/0195529 A1 | 10/2003 | Takamoto et al. |
| 2003/0199975 A1 | 10/2003 | Gabbay |
| 2004/0003819 A1 | 1/2004 | St. Goar |
| 2004/0030382 A1 | 2/2004 | St. Goar |
| 2004/0039442 A1 | 2/2004 | St. Goar |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0049552 A1 | 3/2004 | Motoyama |
| 2004/0087975 A1 | 5/2004 | Lucatero et al. |
| 2004/0087978 A1 | 5/2004 | Velez et al. |
| 2004/0092962 A1 | 5/2004 | Thornton et al. |
| 2004/0097805 A1 | 5/2004 | Verard et al. |
| 2004/0116767 A1 | 6/2004 | Lebovic |
| 2004/0122448 A1 | 6/2004 | Levine |
| 2004/0127983 A1 | 7/2004 | Mortier et al. |
| 2004/0133063 A1 | 7/2004 | McCarthy et al. |
| 2004/0167374 A1 | 8/2004 | Schweich et al. |
| 2004/0167539 A1 | 8/2004 | Kuehn et al. |
| 2004/0225300 A1 | 11/2004 | Goldfarb et al. |
| 2004/0225304 A1 | 11/2004 | Vidlund et al. |
| 2004/0236353 A1 | 11/2004 | Bain et al. |
| 2004/0236354 A1 | 11/2004 | Seguin |
| 2004/0243229 A1 | 12/2004 | Vidlund et al. |
| 2004/0267083 A1 | 12/2004 | McCarthy |
| 2005/0004668 A1 | 1/2005 | Aklog et al. |
| 2005/0021055 A1 | 1/2005 | Toubia et al. |
| 2005/0021056 A1 | 1/2005 | St. Goar |
| 2005/0021057 A1 | 1/2005 | St. Goar |
| 2005/0033446 A1 | 2/2005 | Deem et al. |
| 2005/0044365 A1 | 2/2005 | Bachman |
| 2005/0065396 A1 | 3/2005 | Mortier et al. |
| 2005/0075723 A1 | 4/2005 | Schroeder et al. |
| 2005/0075727 A1 | 4/2005 | Wheatley |
| 2005/0101975 A1 | 5/2005 | Nguyen et al. |
| 2005/0125011 A1 | 6/2005 | Spence et al. |
| 2005/0131277 A1 | 6/2005 | Schweich, Jr. |
| 2005/0131533 A1 | 6/2005 | Alfieri et al. |
| 2005/0143620 A1 | 6/2005 | Mortier et al. |
| 2005/0148815 A1 | 7/2005 | Mortier et al. |
| 2005/0149014 A1 | 7/2005 | Hauck et al. |
| 2005/0154402 A1 | 7/2005 | Sauer et al. |
| 2005/0165419 A1 | 7/2005 | Sauer et al. |
| 2005/0171601 A1 | 8/2005 | Cosgrove |
| 2005/0216039 A1 | 9/2005 | Lederman |
| 2005/0240202 A1 | 10/2005 | Shennib et al. |
| 2005/0251187 A1 | 11/2005 | Beane et al. |
| 2006/0020275 A1 | 1/2006 | Goldfarb et al. |
| 2006/0036317 A1 | 2/2006 | Vidlund et al. |
| 2006/0041306 A1 | 2/2006 | Vidlund et al. |
| 2006/0052868 A1 | 3/2006 | Mortier et al. |
| 2006/0058871 A1 | 3/2006 | Zakay et al. |
| 2006/0074484 A1 | 4/2006 | Huber |
| 2006/0074485 A1 | 4/2006 | Realyvasquez |
| 2006/0089671 A1 | 4/2006 | Goldfarb et al. |
| 2006/0100699 A1 | 5/2006 | Vidlund et al. |
| 2006/0127509 A1 | 6/2006 | Eckman |
| 2006/0135993 A1 | 6/2006 | Seguin |
| 2006/0149123 A1 | 7/2006 | Vidlund et al. |
| 2006/0161040 A1 | 7/2006 | McCarthy |
| 2006/0161193 A1 | 7/2006 | Beane et al. |
| 2006/0184203 A1 | 8/2006 | Martin et al. |
| 2006/0195012 A1 | 8/2006 | Mortier et al. |
| 2006/0195134 A1 | 8/2006 | Crittenden |
| 2006/0195183 A1 | 8/2006 | Navia et al. |
| 2006/0241340 A1 | 10/2006 | Vidlund |
| 2006/0287657 A1 | 12/2006 | Bachman |
| 2007/0002627 A1 | 1/2007 | Youn |
| 2007/0027451 A1 | 2/2007 | Desinger et al. |
| 2007/0049952 A1 | 3/2007 | Weiss |
| 2007/0050022 A1 | 3/2007 | Vidlund et al. |

(56) References Cited

U.S. PATENT DOCUMENTS

| | | | |
|---|---|---|---|
| 2007/0055303 A1 | 3/2007 | Vidlund et al. |
| 2007/0088375 A1 | 4/2007 | Beane et al. |
| 2007/0100356 A1 | 5/2007 | Lucatero et al. |
| 2007/0112244 A1 | 5/2007 | McCarthy |
| 2007/0118151 A1 | 5/2007 | Davidson |
| 2007/0118154 A1 | 5/2007 | Crabtree |
| 2007/0118155 A1 | 5/2007 | Goldfarb et al. |
| 2007/0129737 A1 | 6/2007 | Goldfarb et al. |
| 2007/0179511 A1 | 8/2007 | Paolitto |
| 2007/0197858 A1 | 8/2007 | Goldfarb et al. |
| 2007/0203391 A1 | 8/2007 | Bloom et al. |
| 2007/0232941 A1 | 10/2007 | Rabinovich |
| 2007/0239272 A1 | 10/2007 | Navia et al. |
| 2007/0265643 A1 | 11/2007 | Beane et al. |
| 2007/0299468 A1 | 12/2007 | Viola |
| 2008/0004485 A1 | 1/2008 | Moreschi |
| 2008/0027468 A1 | 1/2008 | Fenton |
| 2008/0051703 A1 | 2/2008 | Thornton et al. |
| 2008/0065011 A1 | 3/2008 | Marchand et al. |
| 2008/0065156 A1 | 3/2008 | Hauser et al. |
| 2008/0065205 A1 | 3/2008 | Nguyen et al. |
| 2008/0091059 A1 | 4/2008 | Machold |
| 2008/0091264 A1 | 4/2008 | Machold |
| 2008/0097482 A1 | 4/2008 | Bain et al. |
| 2008/0097489 A1 | 4/2008 | Goldfarb et al. |
| 2008/0109069 A1 | 5/2008 | Coleman et al. |
| 2008/0125861 A1 | 5/2008 | Webler et al. |
| 2008/0167714 A1 | 7/2008 | St. Goar |
| 2008/0183194 A1 | 7/2008 | Goldfarb et al. |
| 2008/0188873 A1 | 8/2008 | Speziali |
| 2008/0195200 A1 | 8/2008 | Vidlund et al. |
| 2008/0208006 A1 | 8/2008 | Farr |
| 2008/0228223 A1 | 9/2008 | Alkhatib |
| 2008/0243245 A1 | 10/2008 | Thamber et al. |
| 2009/0105729 A1 | 4/2009 | Zentgraf |
| 2009/0105751 A1* | 4/2009 | Zentgraf ............ A61B 17/0469 606/206 |
| 2009/0131880 A1 | 5/2009 | Speziali et al. |
| 2009/0156995 A1 | 6/2009 | Martin et al. |
| 2009/0163934 A1 | 6/2009 | Raschdorf, Jr. |
| 2009/0192598 A1 | 7/2009 | Lattouf et al. |
| 2009/0259304 A1 | 10/2009 | O'Beirne et al. |
| 2010/0030061 A1 | 2/2010 | Canfield et al. |
| 2010/0042147 A1 | 2/2010 | Janovsky et al. |
| 2010/0160726 A1 | 6/2010 | Windheuser |
| 2010/0174297 A1 | 7/2010 | Speziali |
| 2010/0217283 A1 | 8/2010 | St. Goar |
| 2012/0184971 A1 | 7/2012 | Zentgraf et al. |
| 2013/0035757 A1 | 2/2013 | Zentgraf et al. |
| 2013/0150710 A1 | 6/2013 | Zentgraf et al. |
| 2014/0039324 A1 | 2/2014 | Speziali |
| 2014/0364875 A1 | 12/2014 | Zentgrat |
| 2015/0148821 A1 | 5/2015 | Speziali |
| 2017/0290582 A1 | 10/2017 | Speziali |

FOREIGN PATENT DOCUMENTS

| | | |
|---|---|---|
| EP | 1845861 A2 | 10/2007 |
| EP | 1408850 B1 | 9/2009 |
| JP | 06142114 | 5/1994 |
| JP | 2004-531337 | 10/2004 |
| JP | 2007-535342 | 12/2007 |
| WO | WO 1999/00059 A1 | 1/1999 |
| WO | WO 1999/30647 A1 | 6/1999 |
| WO | WO 2000/06026 A2 | 2/2000 |
| WO | WO 2000/06027 A2 | 2/2000 |
| WO | WO 2000/06028 A1 | 2/2000 |
| WO | WO 2000/16700 A1 | 3/2000 |
| WO | WO 2001/66018 A1 | 9/2001 |
| WO | WO 2001/95809 A1 | 12/2001 |
| WO | WO 2003/001893 A2 | 1/2003 |
| WO | WO 2003/059209 A2 | 7/2003 |
| WO | WO 2003/082157 A2 | 10/2003 |
| WO | WO 2003/082158 A1 | 10/2003 |
| WO | WO 2004/021893 A1 | 3/2004 |
| WO | WO 2004/043265 A2 | 5/2004 |
| WO | WO 2005/039428 A2 | 5/2005 |
| WO | WO 2005/087140 A1 | 9/2005 |
| WO | WO 2005/094525 A2 | 10/2005 |
| WO | WO 2006/012750 A1 | 2/2006 |
| WO | WO 2006/032051 A2 | 3/2006 |
| WO | WO 2006/065966 A2 | 6/2006 |
| WO | WO 2006/078694 A2 | 7/2006 |
| WO | WO 2006/116310 A2 | 11/2006 |
| WO | WO 2006/127509 A2 | 11/2006 |
| WO | WO 2007/002627 A1 | 1/2007 |
| WO | WO 2007/027451 A2 | 3/2007 |
| WO | WO 2007/062128 A2 | 5/2007 |
| WO | WO 2007/081418 A1 | 7/2007 |
| WO | WO 2007/117612 A1 | 10/2007 |
| WO | WO 2008/010738 A2 | 1/2008 |
| WO | WO 2009/052528 A2 | 4/2009 |
| WO | WO 2011/070477 A1 | 6/2011 |
| WO | WO 2011/137336 A1 | 11/2011 |
| WO | WO 2012/167120 A2 | 12/2012 |

OTHER PUBLICATIONS

Machine translation of JP 06142114.
Port Access System for Mitral Valve Repair Proves Its Value in Study; MedGadget Jul. 9, 2009 (2 pages).
PCT/US2012/040512, filed Jun. 1, 2012, Search Report and Written Opinion dated Dec. 21, 2012, 19 pages.
PCT International Search Report and Written Opinion, PCT/US06/01699, dated May 6, 2008, 5 pages.
PCT Application No. PCT/US2008/080560, Search Report/Written Opinion dated Aug. 25, 2009, 8 pages.
PCT International Search Report and Written Opinion, PCT/US2019/023876, dated Jun. 17, 2019, 11 pages.
EP Application No. 12792116.1, Extended Search Report dated Jan. 8, 2015, 7 pages.
JP Application No. 2014-513757, Notification of Refusal dated Mar. 7, 2016, translation as obtained through Global Dossier, 3 pages.
AU Application No. 2012261998, Patent Examination Report No. 1, dated Mar. 3, 2016, 4 pages.
CN Application No. 201280038285.7, First Office Action dated Aug. 4, 2015, translation as obtained through Global Dossier, 6 pages.
EP Application No. 12792116.1, Communication Pursuant to Article 94(3) EPC, dated May 24, 2018, 7 pages.
Canadian Application No. 2,837,206, Office Action dated Apr. 18, 2018, 3 pages.
Extended European Search Report, EP 08839048.9, dated Sep. 16, 2010, 7 pages.
Extended European Search Report, EP 06718728.6, dated Nov. 11, 2009.
Application and File History for U.S. Appl. No. 11/813,695, filed Jul. 11, 2007, now U.S. Pat. No. 8,465,500. Inventors: Speziali.
Applciation and File History for U.S. Appl. No. 12/254,808, filed Oct. 20, 2008, now U.S. Pat. No. 9,192,374. Inventors: Zentgraf.
Application and File History for U.S. Appl. No. 12/254,807, filed Oct. 20, 2008, now U.S. Pat. No. 8,758,393. Inventors: Zentgraf.
Application and File History for U.S. Appl. No. 14/310,069, filed Jun. 20, 2014. Inventors: Zentgraf.
Application and File History for U.S. Appl. No. 14/614,570, filed Feb. 5, 2015. Inventors: Speziali.
Application and File History for U.S. Appl. No. 16/406,736, filed May 8, 2019. Inventors: Smirnov et al.
Application and File History for U.S. Appl. No. 16/406,764, filed May 8, 2019. Inventors: Garvin et al.
Application and File History for U.S. Appl. No. 16/406,799, filed May 8, 2019. Inventors: Garvin et al.

* cited by examiner

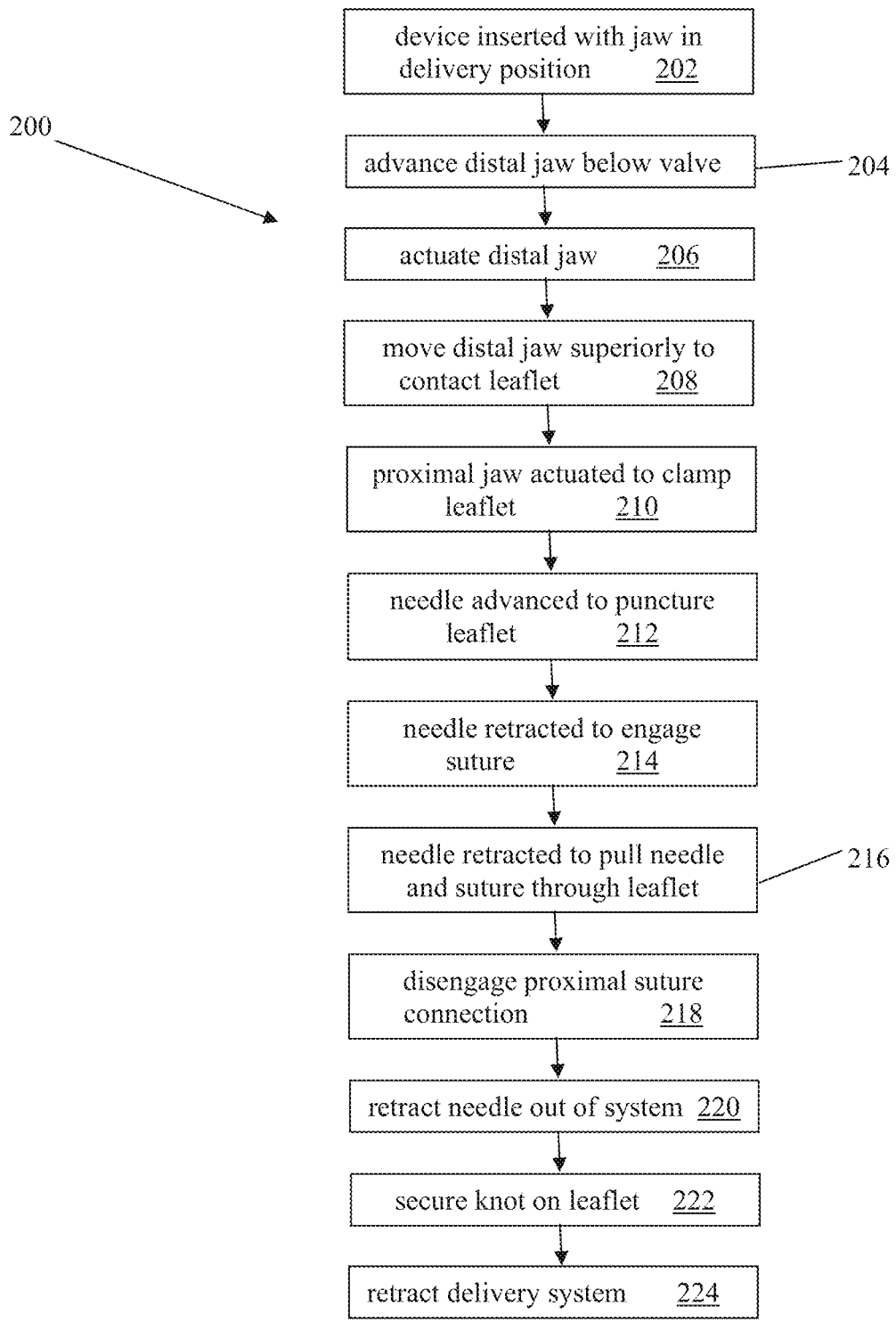

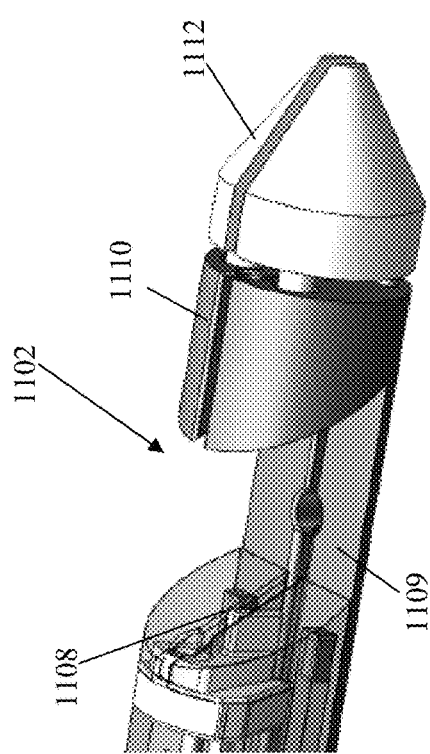
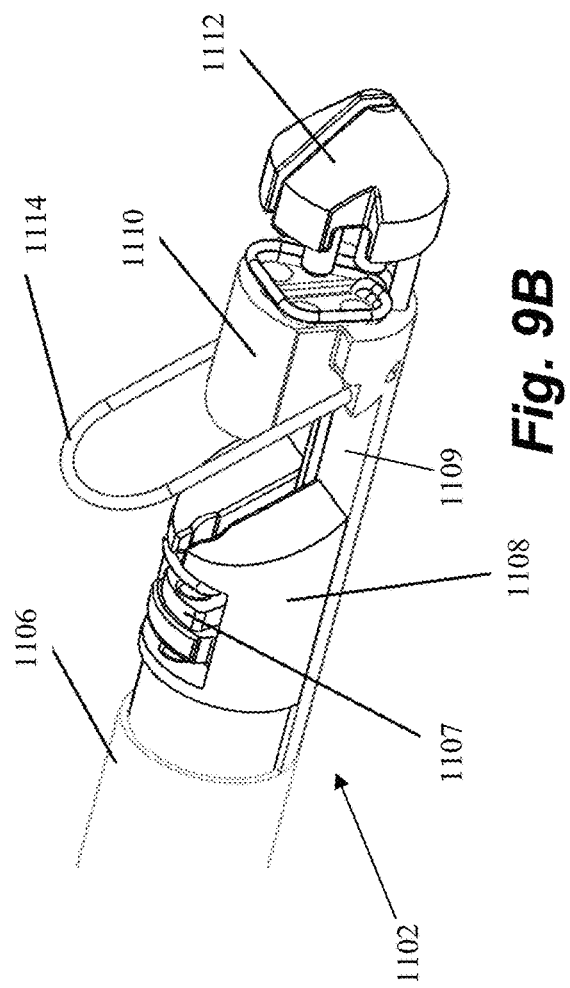

DEVICE FOR SUTURE ATTACHMENT FOR MINIMALLY INVASIVE HEART VALVE REPAIR

RELATED APPLICATION

This application claims the benefit of U.S. Provisional Application No. 62/647,162 filed Mar. 23, 2018, and U.S. Provisional Application No. 62/728,349 filed Sep. 7, 2018, each of which is hereby fully incorporated herein by reference.

TECHNICAL FIELD

The present invention relates to minimally invasive delivery of a suture. More particularly, the disclosed embodiments relate to attaching the suture as an artificial chordae tendineae to a flailing or prolapsing leaflet in a beating heart.

BACKGROUND

The mitral and tricuspid valves inside the human heart include an orifice (annulus), two (for the mitral) or three (for the tricuspid) leaflets and a subvalvular apparatus. The subvalvular apparatus includes multiple chordae tendineae, which connect the mobile valve leaflets to muscular structures (papillary muscles) inside the ventricles. Rupture or elongation of the chordae tendineae results in partial or generalized leaflet prolapse, which causes mitral (or tricuspid) valve regurgitation. A commonly used technique to surgically correct mitral valve regurgitation is the implantation of artificial chordae (usually 4-0 or 5-0 Gore-Tex sutures) between the prolapsing segment of the valve and the papillary muscle.

This procedure was traditionally an open heart operation generally carried out through a median sternotomy and requiring cardiopulmonary bypass with aortic cross-clamp and cardioplegic arrest of the heart. Using such open heart techniques, the large opening provided by a median sternotomy or right thoracotomy enables the surgeon to see the mitral valve directly through the left atriotomy, and to position his or her hands within the thoracic cavity in close proximity to the exterior of the heart for manipulation of surgical instruments, removal of excised tissue, and/or introduction of an artificial chordae through the atriotomy for attachment within the heart. However, these invasive open heart procedures produce a high degree of trauma, a significant risk of complications, an extended hospital stay, and a painful recovery period for the patient. Moreover, while heart valve surgery produces beneficial results for many patients, numerous others who might benefit from such surgery are unable or unwilling to undergo the trauma and risks of such techniques.

Techniques for minimally invasive thoracoscopic repair of heart valves while the heart is still beating have also been developed. U.S. Pat. No. 8,465,500 to Speziali, which is incorporated by reference herein, discloses a thoracoscopic heart valve repair method and apparatus. Instead of requiring open heart surgery on a stopped heart, the thoracoscopic heart valve repair methods and apparatus taught by Speziali utilize fiber optic technology in conjunction with transesophageal echocardiography (TEE) as a visualization technique during a minimally invasive surgical procedure that can be utilized on a beating heart. More recent versions of these techniques are disclosed in U.S. Pat. Nos. 8,758,393 and 9,192,374 to Zentgraf, which disclose an integrated device that can enter the heart chamber, navigate to the leaflet, capture the leaflet, confirm proper capture, and deliver a suture as part of a mitral valve regurgitation (MR) repair. These minimally invasive repairs are generally performed through a small, between the ribs access point, followed by a puncture into the ventricle through the apex of the heart. Although far less invasive and risky for the patient than an open heart procedure, these procedures are still involving significant recovery time and pain.

It would be advantageous for a minimally invasive suture delivery system to be able to suture valve leaflets in a beating heart procedure without requiring an open surgical approach or an incision into the exterior ventricular wall in order to minimize blood loss and reduce recovery time and pain. To that end, various approaches to heart valve repair using intravascular access have been proposed, including U.S. Patent Publication Nos. 2007/0118151 and 2013/0035757 and U.S. Pat. Nos. 7,635,386 and 8,545,551.

SUMMARY

Disclosed herein are minimally invasive systems and methods for intravascularly accessing the heart and performing a transcatheter repair of a heart valve by inserting a suture as an artificial chordae into a heart valve leaflet. In other embodiments, such systems and methods can be employed in other heart valve repair procedures such an edge to edge repair to coapt leaflets by inserting one or more sutures that retain the leaflets in a coapted positioned or inserting a suture to repair a tear in a leaflet, for example.

In one embodiment, a suture attachment catheter configured to repair a heart valve by inserting a suture in a valve leaflet of a beating heart of a patient includes a handle control, a flexible catheter body, and a suture attachment assembly at a distal end of the catheter body. The suture attachment assembly can include a rail between a distal clamping jaw hingedly attached to the rail, and a proximal clamping jaw. One of the proximal clamping jaw or distal clamping jaw can be selectively slideable with respect to the other on the rail using a jaw actuator of the control handle to adjust a distance between the proximal clamping jaw and the distal clamping jaw. A needle can be selectively slideable within the catheter body by using a needle actuator of the proximal handle control to penetrate a valve leaflet and insert a suture through the valve leaflet when the valve leaflet is captured between the proximal clamping jaw and the distal clamping jaw.

Various embodiments of systems, devices, and methods have been described herein. These embodiments are given only by way of example and are not intended to limit the scope of the present invention. It should be appreciated, moreover, that the various features of the embodiments that have been described may be combined in various ways to produce numerous additional embodiments. Moreover, while various materials, dimensions, shapes, implantation locations, etc. have been described for use with disclosed embodiments, others besides those disclosed may be utilized without exceeding the scope of the invention.

BRIEF DESCRIPTION OF THE DRAWINGS

The invention may be more completely understood in consideration of the following detailed description of various embodiments of the invention in connection with the accompanying drawings, in which:

FIG. 6 depicts a flowchart of method steps for inserting one or more sutures into a valve leaflet according to an embodiment.

FIGS. 9A-9B depict a distal capture assembly of a leaflet capture catheter according to an embodiment.

Figure 1A:
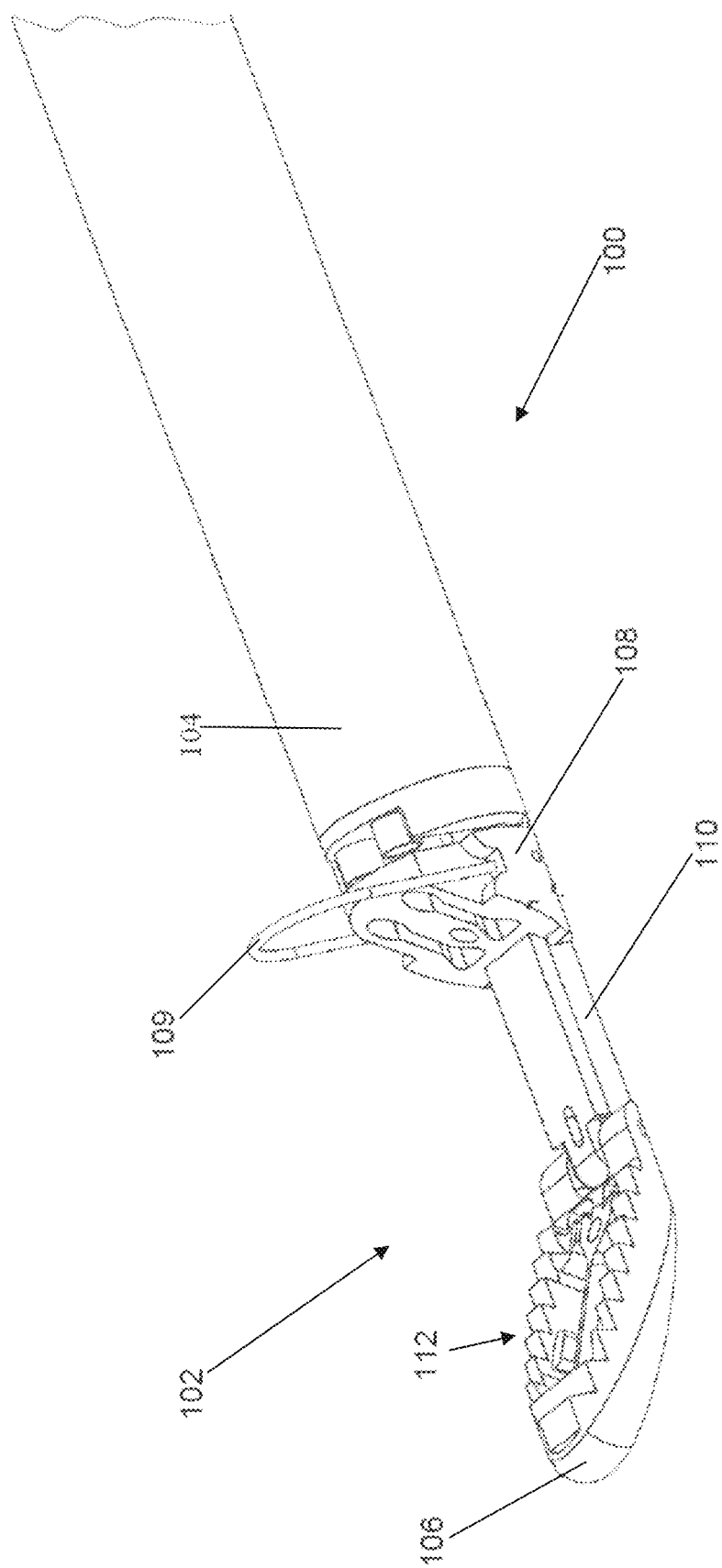
FIGS. 1A-1C depict a distal end of a suture attachment device according to an embodiment.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present application describes various devices and methods that can be employed on the beating heart of a patient in a minimally invasive manner to treat mitral valve regurgitation as described above. Embodiments as described herein can be used to restrain a prolapsing leaflet to prevent leaflet prolapse and to promote leaflet coaptation. In other embodiments, such systems and methods can be employed in other heart valve repair procedures such an edge to edge repair to coapt leaflets by inserting one or more sutures that retain the leaflets in a coapted positioned or inserting a suture to repair a tear in a leaflet, for example.

Figure 1B:
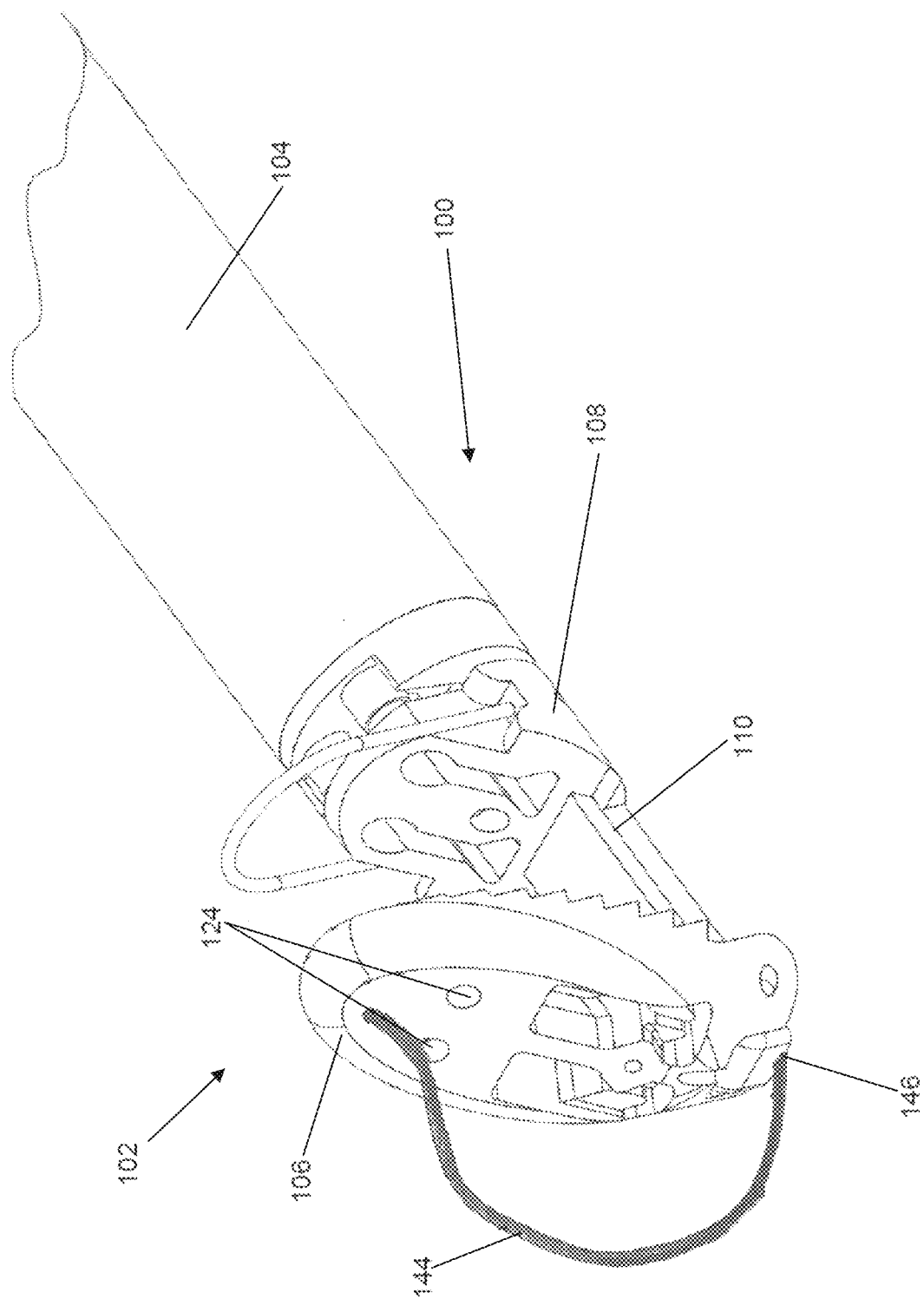
Figure 1C:
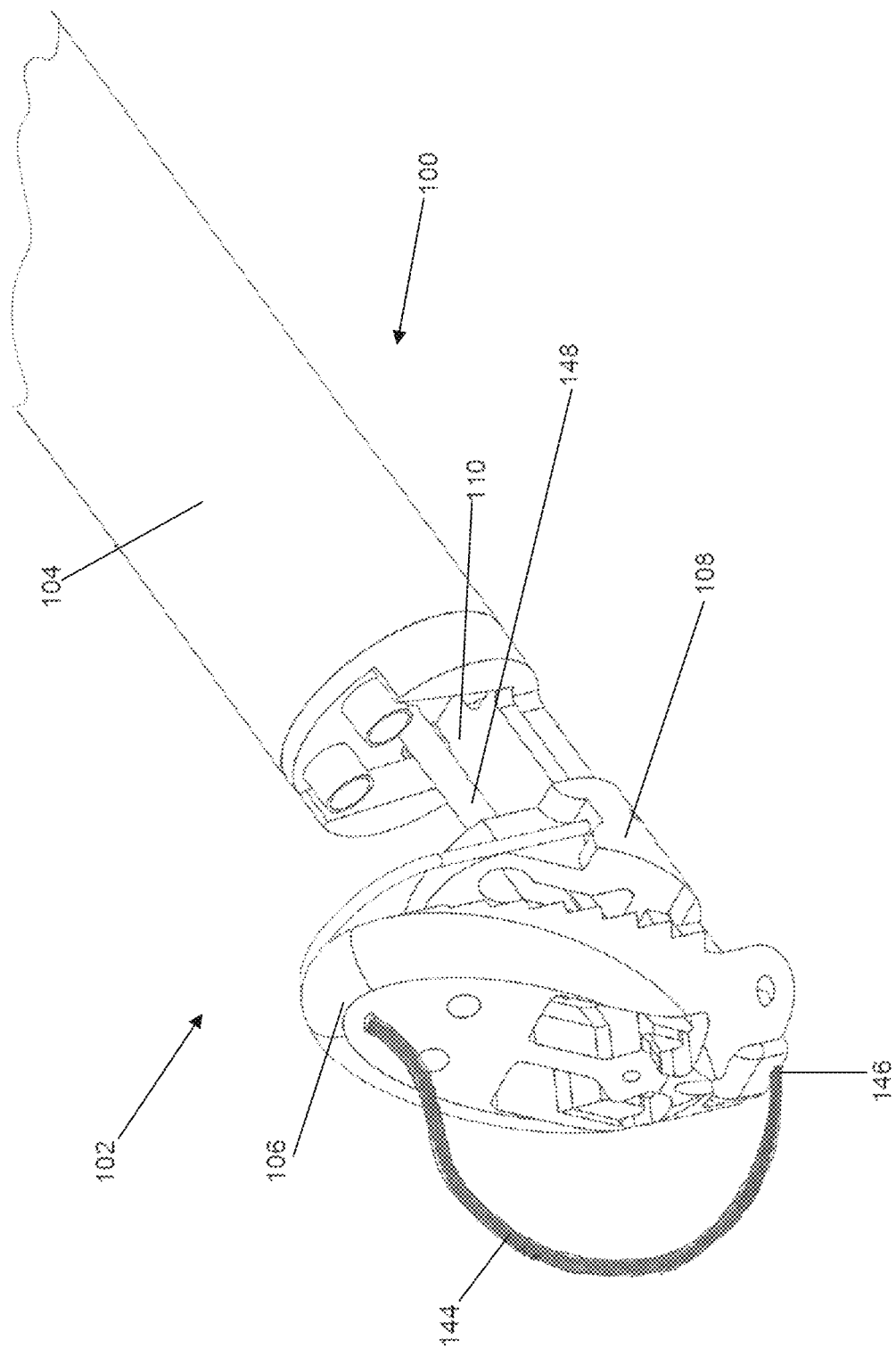

FIGS. 1A-1C depict a distal end 102 of a suture attachment device 100 according to an embodiment. Suture attachment device 100 can be configured as leaflet attachment catheter with the distal end 102 being the distal capture portion of the leaflet attachment catheter. In embodiments, the catheter is configured to enter the patient through a delivery sheath which is inserted at the groin, extends through the inferior vena cava to the right atrium and then through a transseptal puncture into the left atrium. The catheter has a shaft or body 104 of a length to extend through the delivery sheath while allowing the distal end 102 to extend distal to the distal end of the delivery sheath within the patient while also extending proximally to the proximal end of the delivery sheath at the proximal end of the catheter allowing the physician to access the control handle attached to the proximal end of the catheter. In such an embodiment, the catheter body 104 can be flexible.

In embodiments, the total working length of the catheter body can be between about 130 cm and 140 cm. On a typical patient, this length enables the catheter to be advanced into the heart from the groin with additional length for the delivery system catheters and control handles. The catheter can be flexible and configured to be able to flex around a curve having a diameter between 0.75 inches and 1.5 inches, such as, for example, a 0.9 inch diameter curve, depending on the septal puncture location and the specific anatomy of the patient. In other embodiments, the total working length can be between about 100 cm and 170 cm in order to accommodate very short or very tall patients.

In embodiments, the working length of the distal end 102 of the device advanced out of the delivery system can be between about 3 cm and 6 cm. The distal end 102 can be generally rigid, but provided with some flexibility as the device is advanced through the delivery system by a hinged distal jaw as will be described herein. This flexibility enables the distal end to traverse curves on the range of 0.75 inches to 1.5 inches within the internal diameter of the delivery system which, in some embodiments, may be approximately 5-6 mm.

In embodiments, catheter shaft or body is comprised of a combination of stainless steel braid and coil reinforced nylon or polyurethane to provide axial and torsional rigidity along with flexibility. The components of the distal end, such as the clamping jaws as will be described herein, can be comprised of, for example, medical grade polymers or machined stainless steel.

The distal end 102 of the catheter 100 includes a distal jaw 106 and a proximal jaw 108 and mechanisms that actuate the jaws between their respective positions depending on the portion of the procedure being done, as will be described herein. Distal jaw 106 is hingedly attached to a rail 110. Proximal jaw 108 is selectively slideable along rail 110 and can include a loop 109 configured as a wire extending upwardly therefrom. In embodiments, wire loop 109 can be formed from a shape memory material such as, e.g., nitinol. In operation, distal jaw 106 can selectively be actuated between a first position shown in FIG. 1A and a second position shown in FIGS. 1B-1C. Proximal jaw 108 can selectively slide along rail 110 between a first, proximal position depicted in FIGS. 1A-1B and second, distal position depicted in FIG. 1C. In another embodiment, the proximal jaw 108 can be fixed in its axial movement and the rail 110 with the distal jaw 106 attached can slide distally from a first position with respect to the fixed proximal jaw to a second position to effectively increase the distance between the proximal jaw and the distal jaw.

Figure 2A:
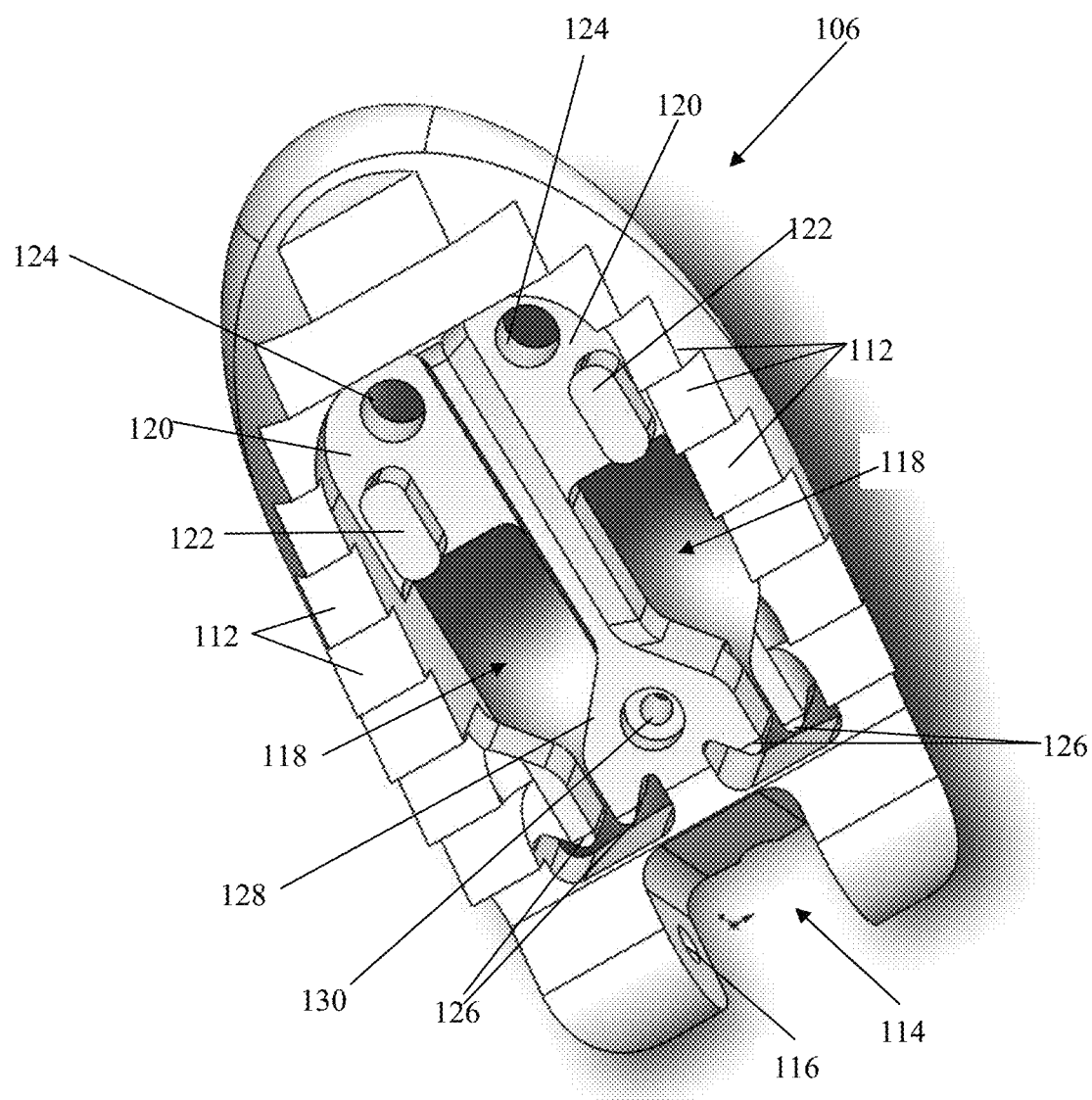
FIGS. 2A-2B depict a distal jaw of the suture attachment device of FIGS. 1A-1C.
Figure 2B:
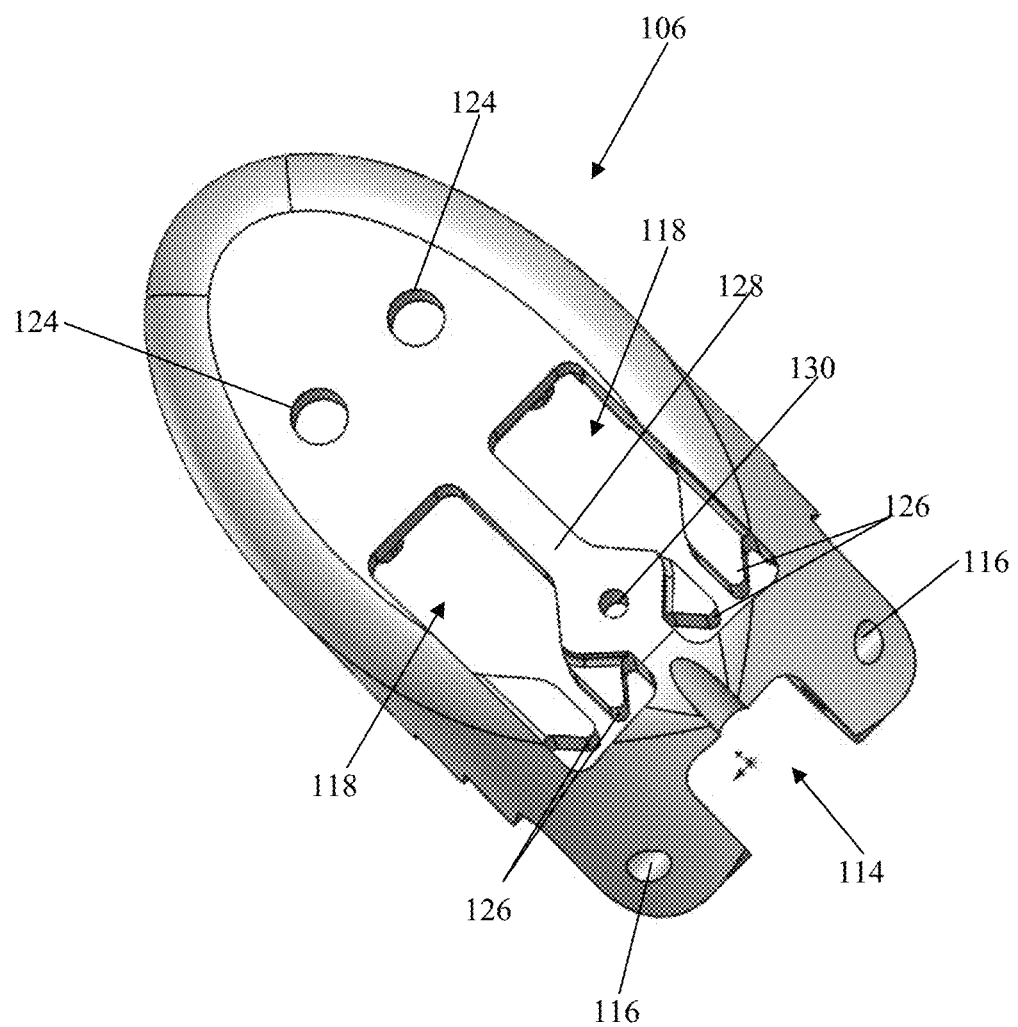

Referring now also to FIG. 2A-2B, further details regarding the distal jaw 106 according to an embodiment will be described. Distal jaw 106 includes a leaflet clamping surface having a plurality of stepped ridges 112 configured to enhance the ability of the jaws to clamp and retain a valve leaflet. Distal jaw 106 further includes a rail opening 114 and a pair of aligned apertures 116 extending through distal jaw 106. Rail opening 114 is configured to receive a distal end of rail 110 (see FIG. 1A) with the apertures 116 configured to receive a pin, rod, etc. that extends through a corresponding aperture in rail 110 to form the hinged attachment between distal jaw 106 and rail 110. Distal jaw 106 further includes a pair of clamping face openings 118. A portion of clamping face openings 118 extends completely through the distal jaw 106 whereas another portion extends only partway through due to the presence of ledges 120. A distal post 122 extends upwardly from and a distal aperture 124 extends through each ledge 120. Clamping face openings 118 further each define a pair of intermediate tabs 126. A recessed opening 130 also extends through a ledge 128 extending between the openings 118.

Figure 3:
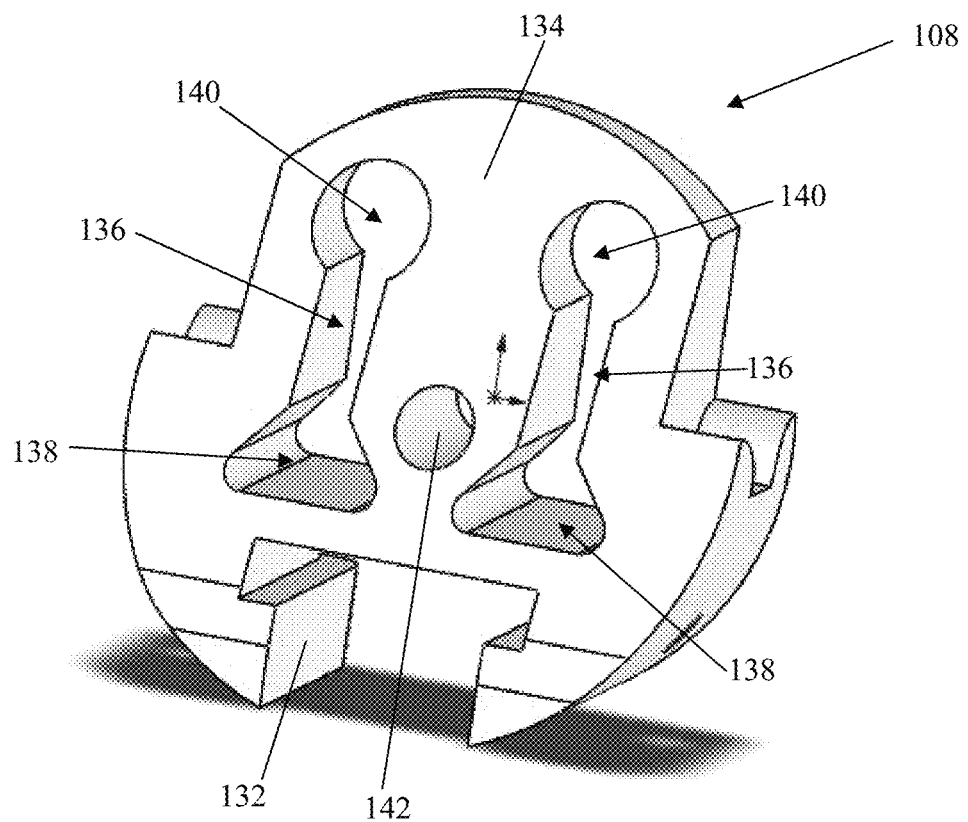
FIG. 3 depicts a proximal clamping jaw of the suture attachment device of FIGS. 1A-1C.

Referring now to FIG. 3, further details regarding an embodiment of a proximal clamping jaw 108 are depicted. Proximal jaw 108 includes a rail opening 132 that conforms to a shape of the rail 110 (see FIG. 1A) to enable proximal jaw 108 to selectively slide along rail 110. Proximal jaw 108 further includes a distal clamping face 134 having a pair of elongate slots 136 therethrough. Elongate slots 136 each define both a suture slot 138 and a needle hole 140. An actuator aperture 142 is further defined through proximal jaw 108.

As noted above, and with reference again to FIGS. 1A-1C, distal jaw 106 can be actuated between at least two positions. The first, delivery position is depicted in FIG. 1A and includes the distal jaw 106 being positioned at an obtuse angle (i.e., an angle between 90 and 180 degrees) relative to the rail 110. In the depicted embodiment, the distal jaw 106 is positioned approximately 120 degrees relative to the rail. The delivery position is the configuration in which the distal end 102 is delivered through the delivery system to the point of use (i.e., adjacent a valve leaflet). The second, clamping position is depicted in FIGS. 1B-1C and includes the distal jaw 106 positioned at a right angle or acute angle (less than 90 degrees) relative to the rail 110. In the depicted embodiment, the distal jaw 106 has been actuated approximately 90 degrees relative to the first position, such that the jaw 106 is positioned at an approximately 60 degree angle relative to the rail 110. The clamping position is the position the distal jaw 106 is moved to when the jaw 106 has been positioned inferior to a leaflet to enable to jaw surface to contact and stabilize the leaflet for capture of the leaflet.

Actuation of the distal jaw 106 between the delivery position and the clamping position is accomplished with a flexible member 144. In embodiments, flexible member 144 can be a nitinol wire. Flexible member 144 can extend through a lumen 146 through the catheter shaft or body 104 and the rail 110 and exits lumen 146 at a distal face of the rail 110. The distal end of the flexible member 144 attaches to the distal jaw 106. Although not depicted as such in FIGS. 1B-1C, in embodiments the flexible member 144 can be attached to the distal jaw 106 via one or more of distal apertures 124. When this flexible member 144 is further extended from the lumen 146, its connection to the distal jaw 106 moves the jaw from the first, delivery position in which it is delivered to the second, clamping position in which is able to contact the inferior surface of the valve leaflet. The distal jaw 106 can be moved back to the delivery position by pulling on the flexible member 144. Flexible member 144 can be controlled with sliding movement of an actuator disposed at a proximal end of the device.

The proximal jaw 108 is actuated with a flexible proximal jaw actuator rod 148, as shown in FIG. 1C, that connects to the actuator aperture 142 of the proximal jaw 108. The actuator rod 148 can be pushed moved an actuator control at the proximal end of the device to advance the proximal jaw 108 along the rail 110 to close the distance between the proximal jaw 108 and the distal jaw 106 to clamp a leaflet therebetween. Wire loop 109 on proximal jaw 108 is configured to approximately mate (on opposite sides of the leaflet) with the distal jaw 106 when both jaws have been actuated to the clamping position. When the proximal jaw 108 is advanced to the actuated distal jaw 106 with the valve leaflet between them, it will provide pressure to stabilize the leaflet between the jaws while minimizing potential damage to the leaflet. In some embodiments, distal clamping face of proximal jaw 108 can be angled to match the angle of distal jaw 106 in the clamping position (i.e., approximately 60 degrees in the depicted embodiment).

The above-described jaw configuration provides a number of advantages. One advantage is that it allows for relatively large surface areas to be included in the clamping portion of the jaw by providing for a first configuration in which the larger distal jaw can more easily be delivered and a second, different configuration in which the larger jaw is employed to capture and retain a leaflet. Another advantage is that the hinged connection reduces the rigid length of the device while still allowing a large jaw opening distance. It does this by allowing the hinged distal jaw to flex as needed while the system is advanced through the small radius that is required for delivery to the mitral valve through the vasculature and a septal puncture.

Figure 4A:
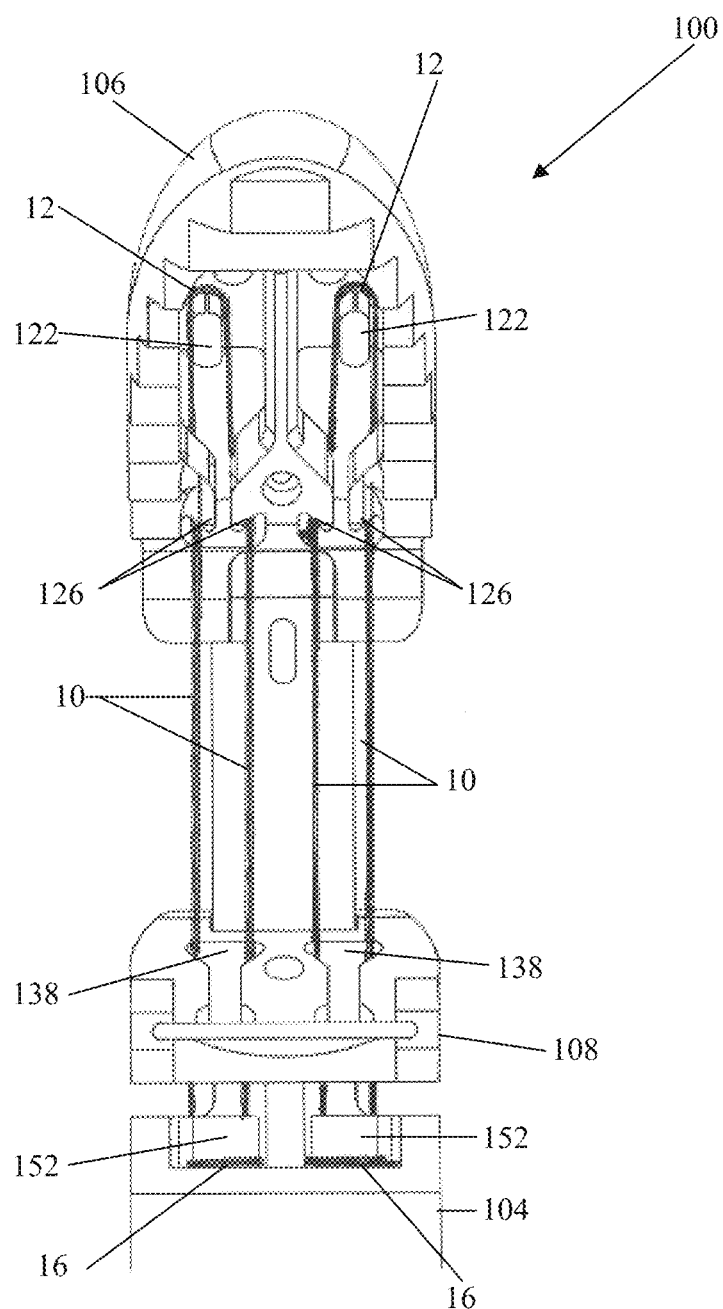
FIGS. 4A-4B depict schematic representations of the routing of one or more sutures through a suture attachment device according to an embodiment.
Figure 4B:
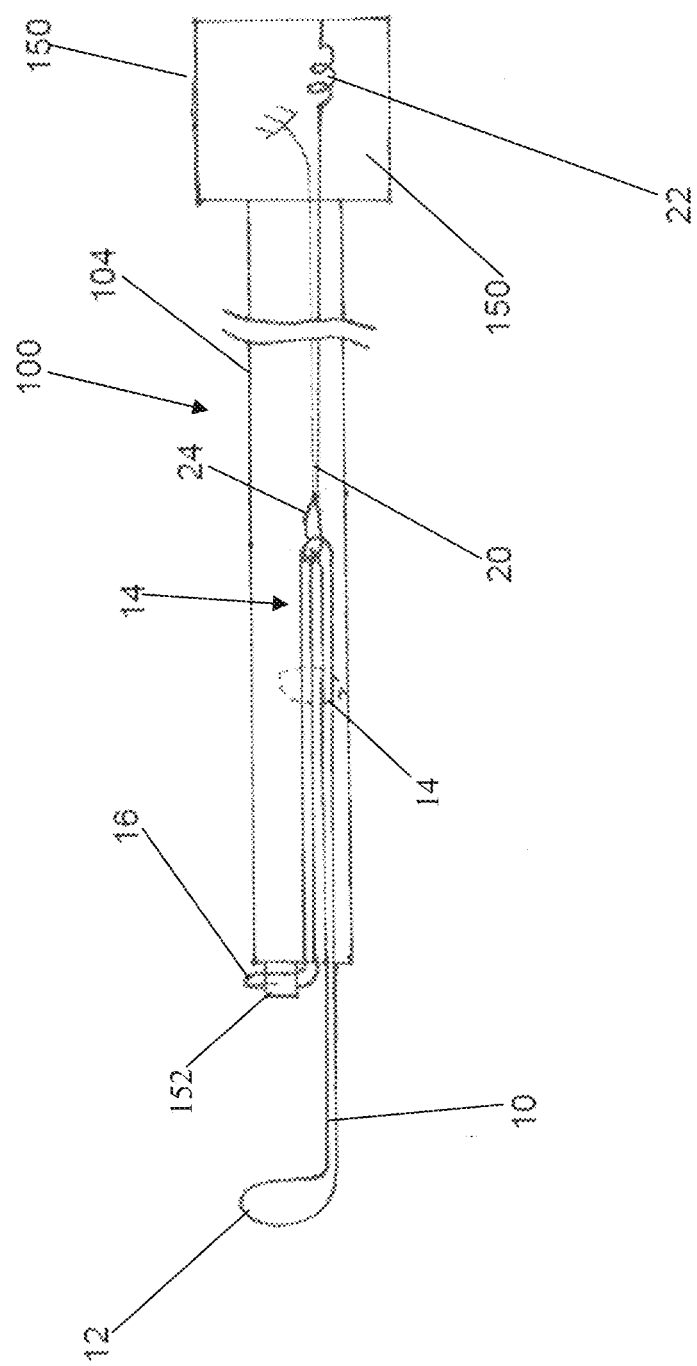

FIGS. 4A-4B depict schematic representations of an embodiment of a manner in which one or more sutures can be routed through the device 100. FIG. 4B depicts device without the proximal jaw 108 and distal jaw 106 as well as a single suture 10 for sake of clarity. FIG. 4A depicts a pair of sutures 10 carried side by side in device 100. Because each suture is routed through device in an identical but side by side manner, only the routing of a single suture 10 will be described in detail. In embodiments, one or more sutures can be preinstalled in the catheter prior to delivery to the end user (i.e., surgeon).

Suture 10 can be configured in a continuous loop through device 100. The routing of the suture 10 through the distal jaw is done by securing a first distal end suture loop 12 portion around the distal post 122 on the leaflet clamping surface side of the distal jaw 106. The suture 10 then extends from both sides of the post and around the opposite side of the intermediate tabs 126 in the distal clamping jaw 106, through the suture slots 138 in the proximal jaw 108 and then into a suture channel extending through the catheter body 104. Within each suture channel of the catheter body 104, both legs of the suture 10 are doubled with the resulting proximal double loop 14 of suture 10 being held with a separate looped suture 20 which is connected within the proximal control handle 150 by a spring 22 to keep tension on the suture 10 to keep it in place in the catheter body 104. The second, proximal end suture loop 16 extends from the doubling point 14 distally until it is looped around a needle support tube 152 through which the needle is advanced to penetrate the leaflet and insert the suture around the leaflet.

Figure 5A:
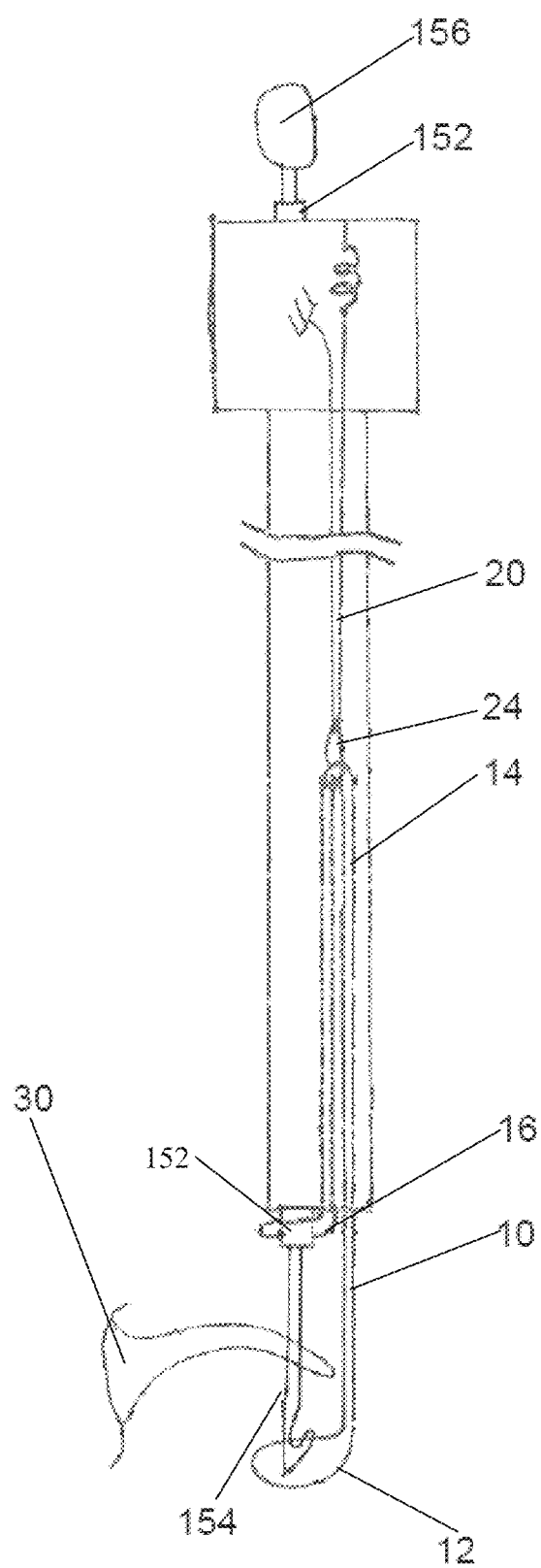
FIG. 5A-5D depict a sequence of steps for inserting one or more sutures into a valve leaflet according to an embodiment.

The proximal control mechanism 150 for the device 100, depicted schematically in FIG. 4B, consists of a main body that allows comfortable access to the controls of the device. The separate looped suture 20 is secured in the handle 150 by a spring 22 at one end of the loop 20, and a disengageable connection 24 at the other. As shown in FIG. 5A, the needle 154 extends through the control mechanism 150 and the proximal end of the needle contains a handle 156 which allows for comfortable access and control of the needle 154.

The control handle also houses two sliding controls (not depicted). The first sliding control is connected to the distal jaw actuator such as flexible member 144 extending through a lumen in the catheter body 104. Distal relative movement of the first slider with respect to the control handle 150 will actuate the distal jaw 108. The second sliding control is connected by a flexible rod 148 extending through the catheter body 104 to the proximal jaw 108. Distal relative movement of the second slider with respect to the control handle 150 will actuate the proximal jaw 108. Further details regarding proximal controls for control elements at a distal end of a leaflet capture catheter can be found in U.S. Provisional Patent Application No. 62/647,162, filed Mar. 23, 2018, which is hereby incorporated by reference herein.

FIGS. 5A-5D depict a sequence of steps of an embodiment of using device 100 to insert one or more sutures into a valve leaflet and FIG. 6 depicts a flowchart of method steps 200 corresponding to the sequence. FIGS. 5A-5D depict the device 100 without the distal jaw 106 and proximal jaw 108 for sake of clarity. In step 202, the device is inserted through the delivery system with the distal jaw in the un-actuated, first delivery configuration. In embodiments, access into the heart adjacent the mitral valve can be gained intravascularly as described herein. Further details regarding such access can be found in U.S. Provisional Patent Application No. 62/647,162 incorporated by reference above. In embodiments, the device is inserted with two sutures 10 loaded into the device, though only a single suture 10 is depicted in FIGS. 5A-5D for sake of clarity.

After exiting the delivery system, the distal jaw of the device is advanced below the level of the mitral valve at step 204 and the distal jaw is actuated at step 206 moving the jaw to an angle in which it will contact the valve leaflet. After the device is positioned to the desired point of leaflet attachment, the system is moved superiorly at step 208 with respect to the valve until the lower (distal) jaw contacts the inferior side of the valve leaflet. The proximal jaw is then actuated at step 210 by sliding it along the rail until the leaflet is clamped and stabilized between the jaws.

Figure 5B:
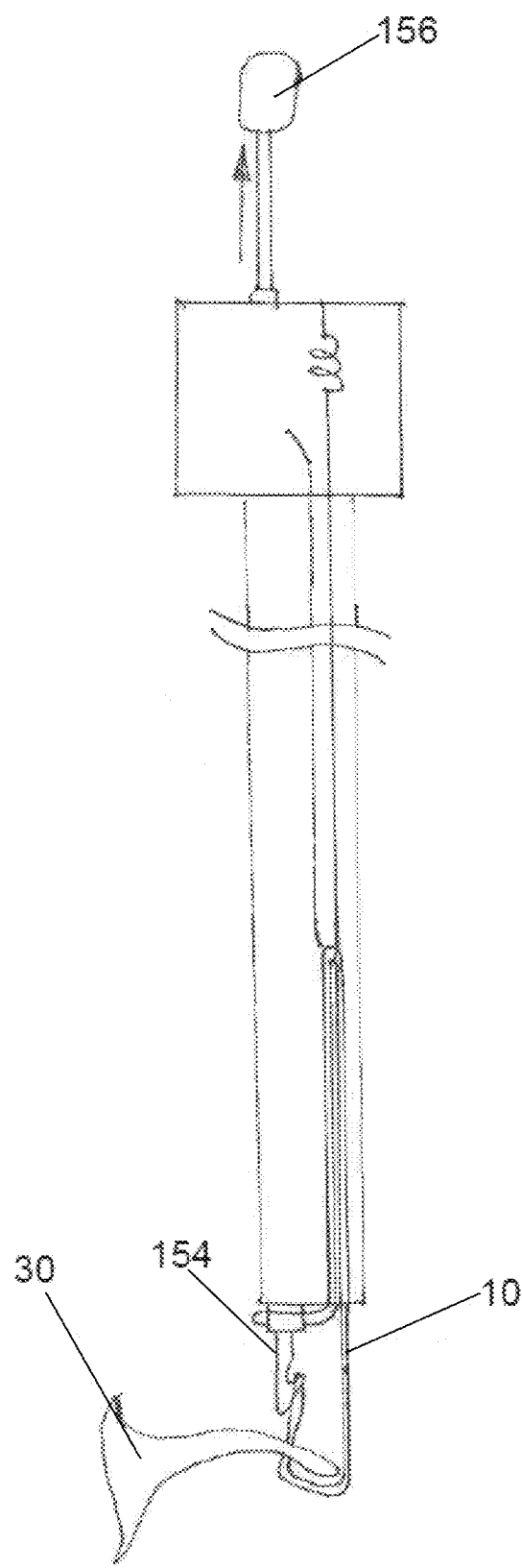
Figure 5C:
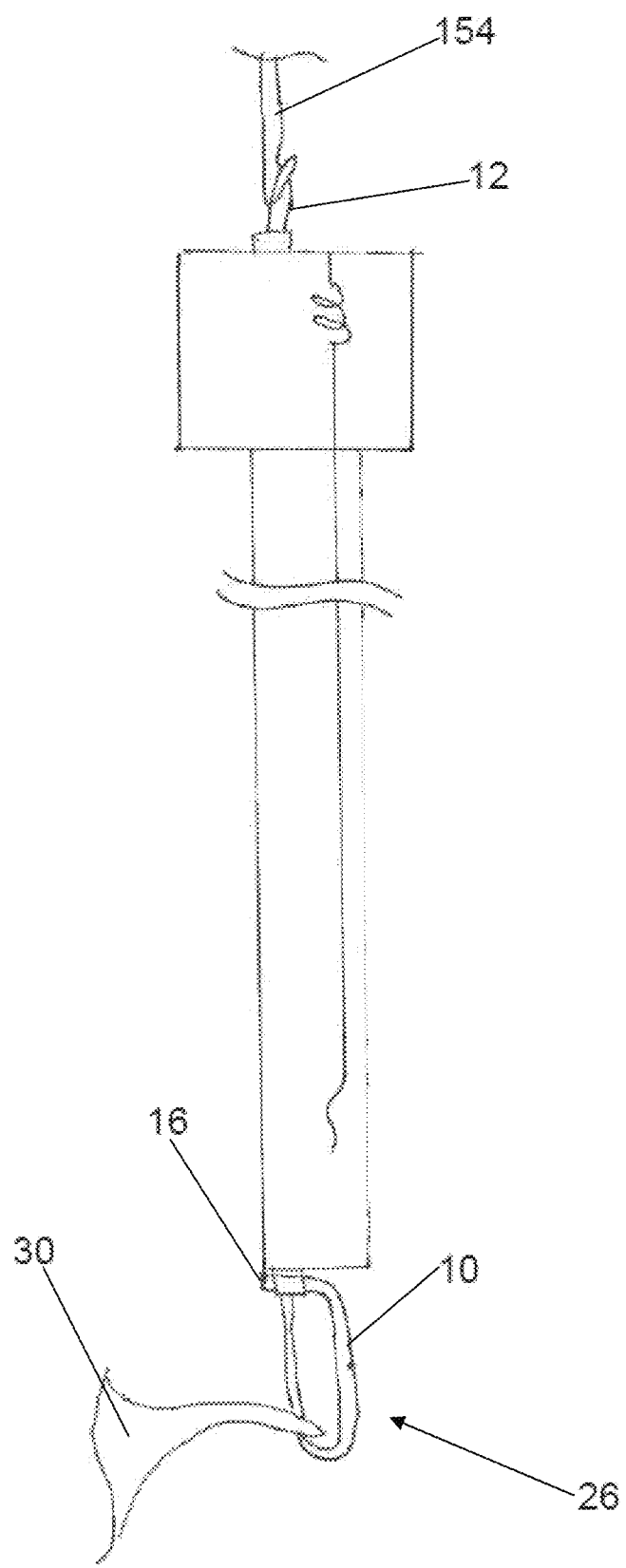
Figure 5D:
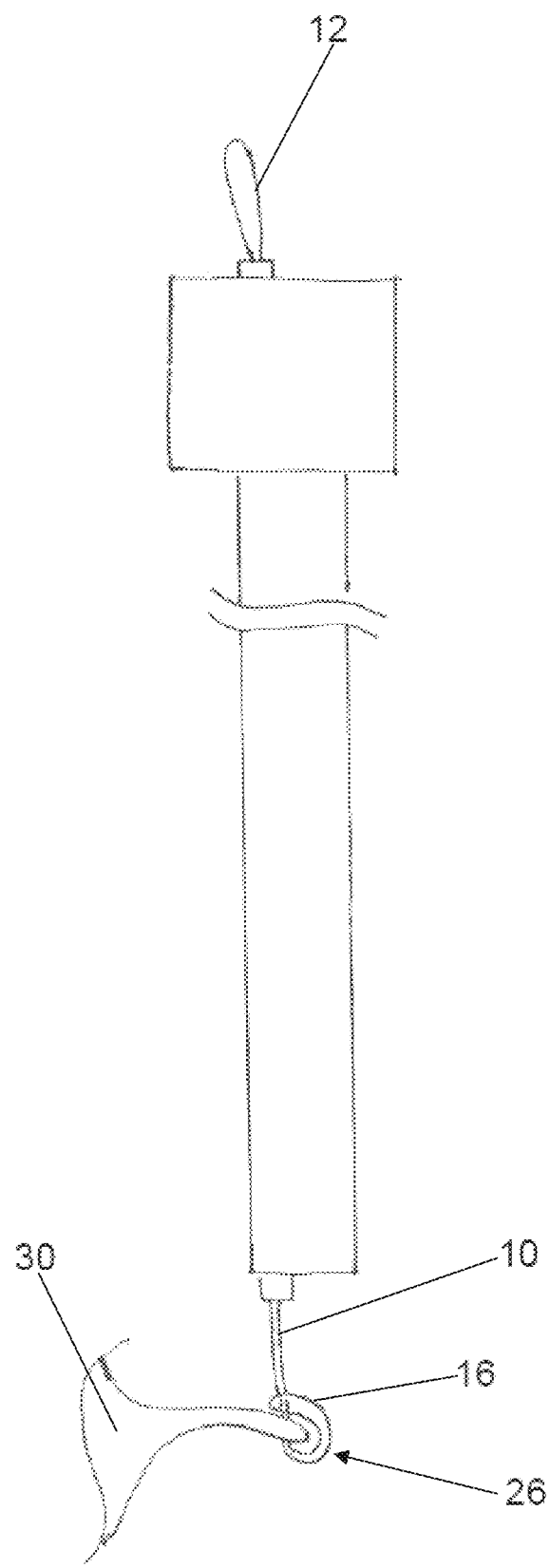

Once the leaflet 30 is stabilized between the jaws, the needle 154 is advanced at step 212 puncturing the valve leaflet and extended through an opening in the distal jaw and between the suture segments that are positioned around the post and intermediate tabs in the distal jaw. The needle 154 is then retracted which engages the suture with the hook in the needle profile as shown in FIG. 5A at step 214. This pulls the distal suture loop 12 off from the distal post of the distal jaw and the needle can then pull the suture loop through the puncture in the valve leaflet 30 at step 216 as depicted in FIG. 5B. Due to the angle geometry of the intermediate tabs 126, a distal portion of the suture will remain wrapped around them keeping this distal portion of the suture from contacting the distal side of the leaflet. This enables the suture to be tightened without putting force on the leaflet that could potentially damage the leaflet. With the needle 154 on the proximal side of the valve leaflet 30 and the distal suture loop 12 in the needle hook, the disengageable connection 24 to the proximal suture loop 16 via the separate suture 20 looped around the double loop 14 is released in the control handle at step 218. Further retraction of the needle 154 at step 220 will then pull the proximal loop 16 distally into the system. At the point that the needle 154 is fully pulled from the system with the distal suture loop 12 that is in the needle 154 exposed, the resulting girth hitch knot 26 is very close to being tightened at the distal end of the system as depicted in FIG. 5C. The final step 222 to tighten the knot 26 is when the secured distal loop 12 is pulled distally from the needle tube allowing the knot 26 to be secured at the leaflet as depicted in FIG. 5D.

Once the knot 26 is tightened on the leaflet 30, the delivery system can be retracted at step 224. To do so, the proximal jaw may be released and moved proximally, un-clamping the valve leaflet. The distal jaw is then un-actuated. The change in the distal jaw angle releases the suture from intermediate tabs 126 in the distal jaw which then fully detaches the system from the leaflet. The catheter can then be retracted into the delivery system or the optional second suture may be delivered by moving the system to a different position along the leaflet and repeating the process sequence described above. Once one or more sutures have been attached to the leaflet, the suture(s) can be adjusted to provide an appropriate length and/or tension for proper valve function and anchored.

Figure 7:
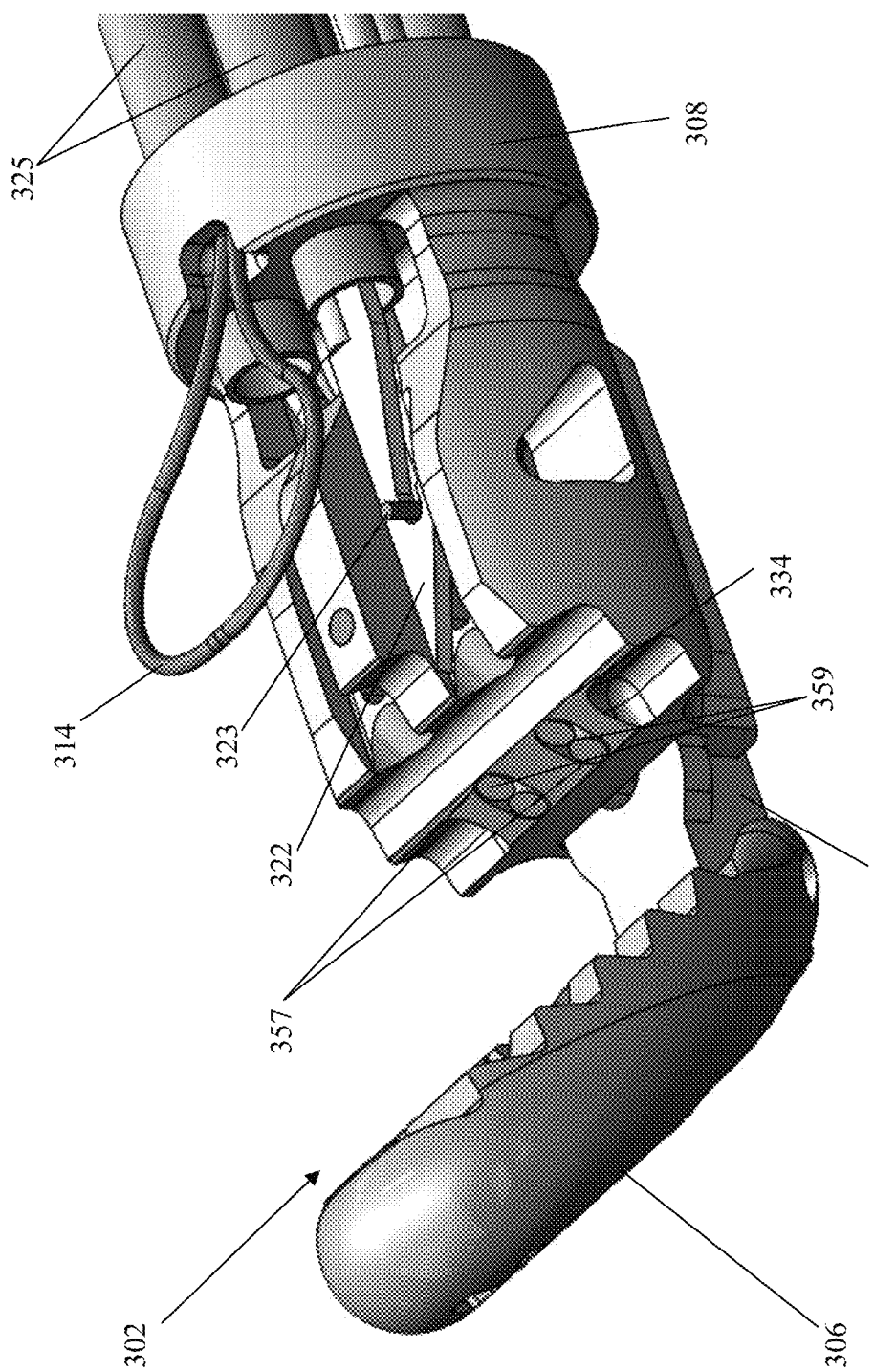
FIG. 7 depicts a distal end of a suture attachment device according to an embodiment.

FIG. 7 depicts another distal end of a leaflet capture catheter 302 according to an embodiment. In this embodiment, the proximal jaw 308 is stationary and longitudinally fixed in place. Rail 310 can be slidable to adjust the distance between proximal jaw 308 and distal jaw 306 to aid in leaflet capture as will be discussed in more detail below with regard to FIGS. 8A-8D. As with leaflet capture catheter 102, the distal jaw 306 can be pivotable to also aid in leaflet capture. Each needle 322 can include a keying wire 323 that retains the needle in place distally of the needle lumens 325. In one embodiment, keying wire 323 can be provided with a forward bias and the needle 322 a backward bias to keep the needle in place and when the needle 322 is pushed forward the wire 323 drops out of the path of the needle 322. In another embodiment, the keying wire 323 can be retracted, such as with a control element on the proximal handle of the device attached to the wire, such that no spring biases are utilized. As will be discussed in more detail below, this embodiment depicts two sets of fiber optic cables 359 (each including one transmission fiber and one return fiber) disposed in fiber optic channels at the distal clamping face 334 of the proximal jaw 108 to aid in verifying proper leaflet capture. The depicted embodiment further includes a stabilizing loop 314 as described in more detail below. Leaflet capture catheter 302 can further include any feature described with respect to the other embodiments disclosed herein.

Figure 8A:
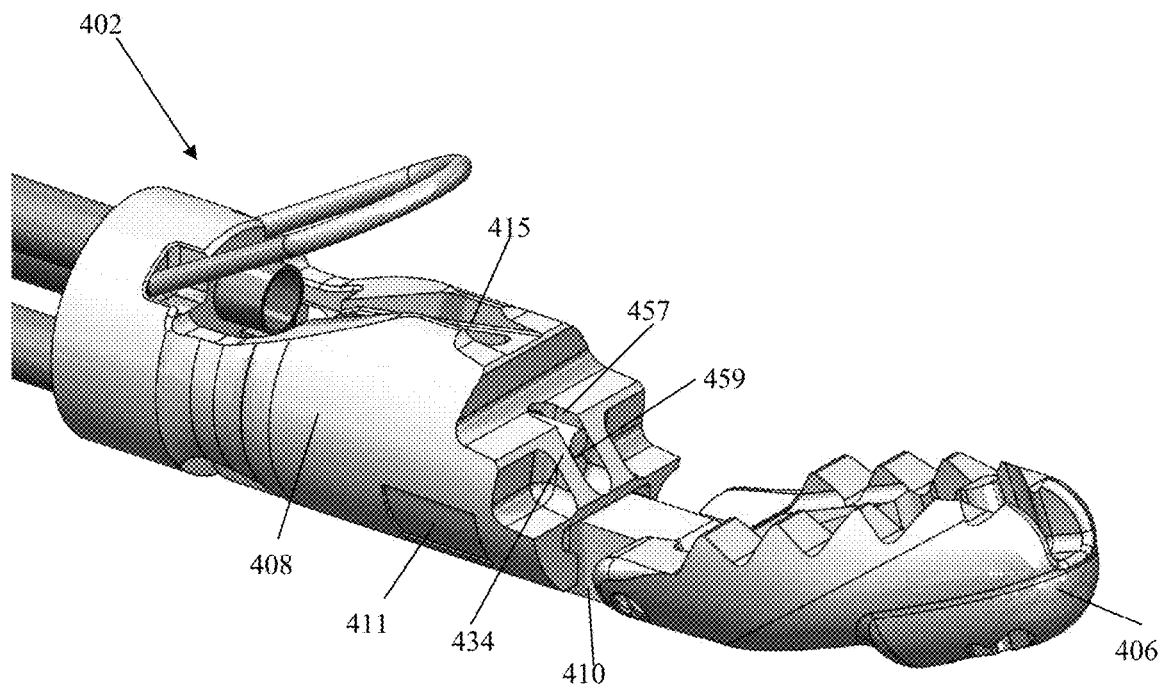
FIGS. 8A-8F depict a distal end of a suture attachment device according to an embodiment.
Figure 8B:
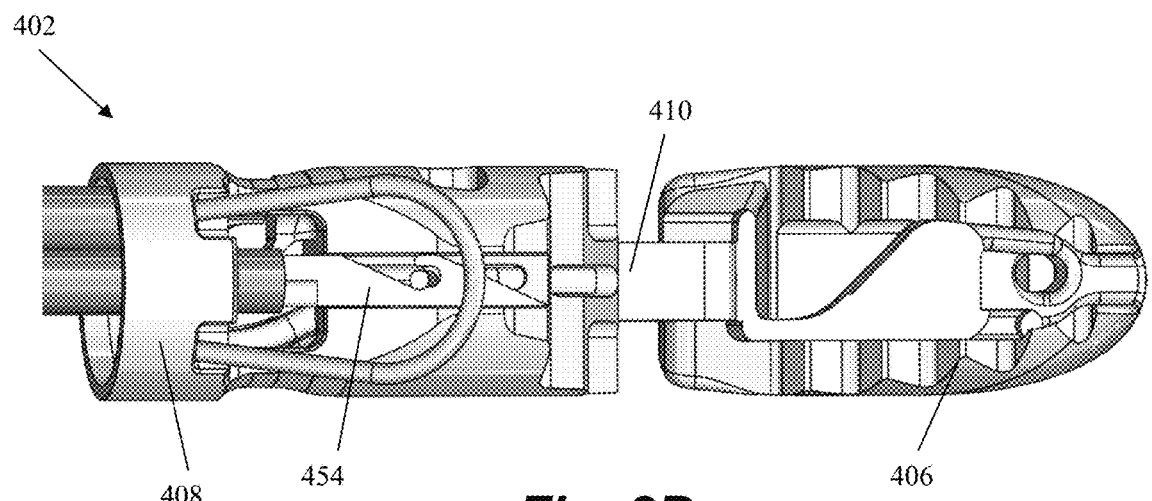
Figure 8C:
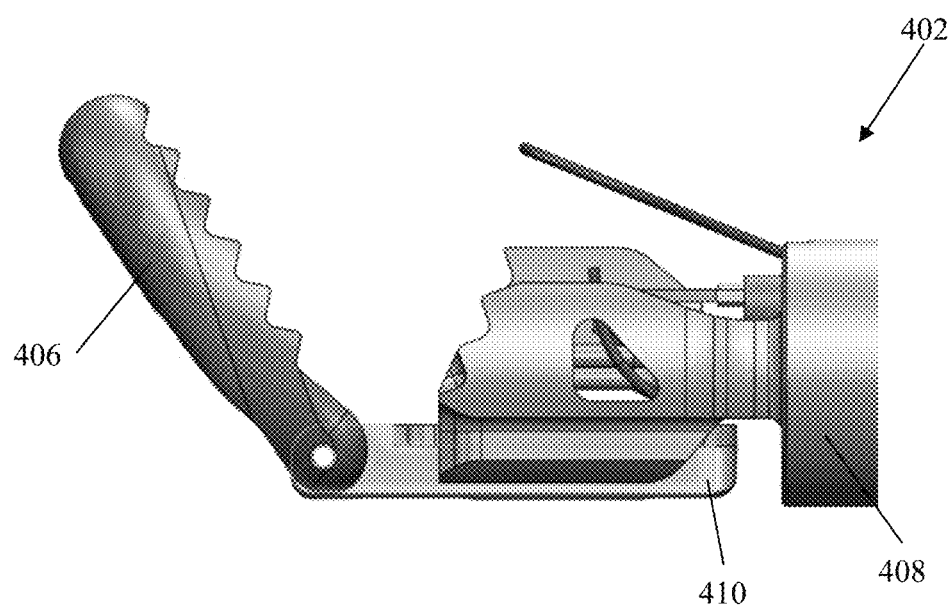
Figure 8D:
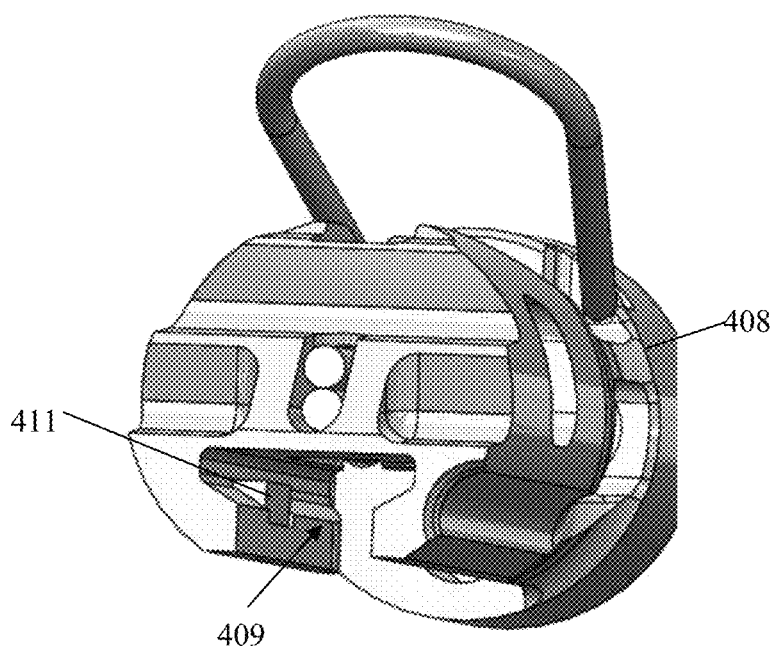

FIGS. 8A-8D depict another distal end of a leaflet capture catheter 402 according to an embodiment. This embodiment can be configured to carry only a single suture and a single needle 454 and can have a single pair of fiber optics 459 in a fiber optic channel 457. Distal jaw 406 can be hingedly attached to rail 410. Rail 410 can be slideable with respect to proximal jaw 408 to adjust a separation distance between the jaws 408, 410. Referring to FIGS. 8C-8D, rail 410 can have limited length and be connected to a hypotube (not pictured) controllable from the proximal handle to slide rail 410 within a rail channel 409 defined in proximal clamping jaw 408. Proximal jaw 408 can further including a locking tab 411 that can mechanically interact with a locking feature on rail 410 to prevent the rail 410 from being completed moved distally from the rail channel 409. In embodiments, the rail 410 can be biased proximally, towards a closed position with a spring force that is overcome to open the jaws, which enables the jaws to remain clamped around a leaflet once a leaflet is captured. Referring to FIG. 8A, the needle channel 415 along proximal jaw 408 across which the needle 454 travels to engage the leaflet can be ramped at an upwards angle to ensure the leaflet is pierced sufficiently above the leaflet edge. Leaflet capture catheter 402 can further include any feature described with respect to the other embodiments disclosed herein.

Figure 8E:
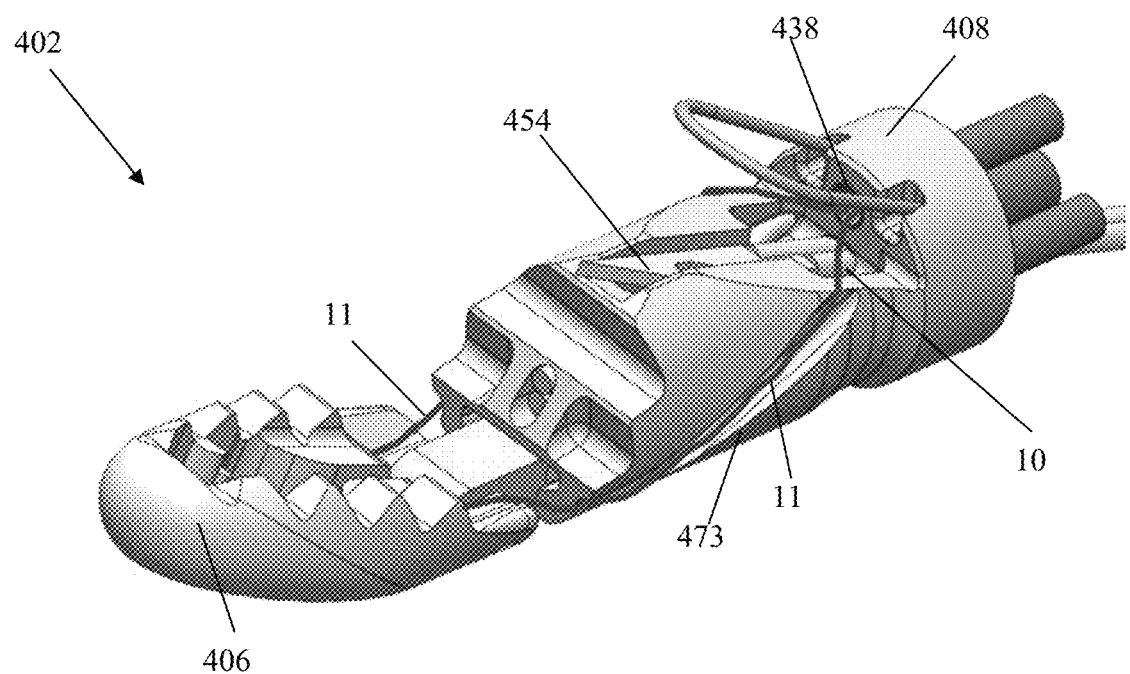
Figure 8F:
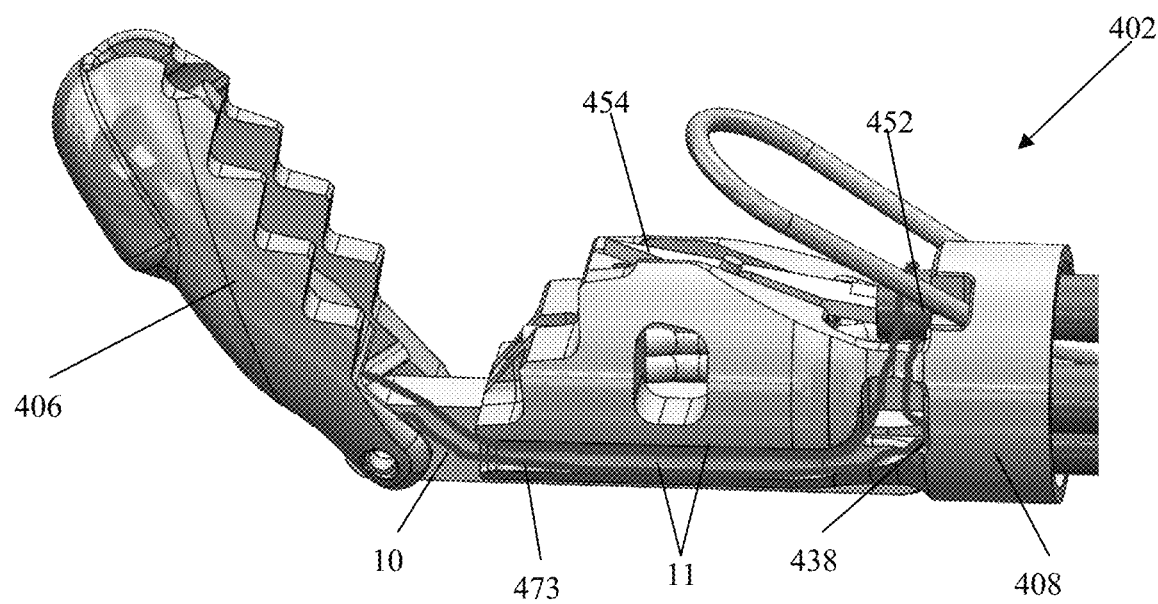

FIGS. 8E-8F depict alternatives as to how a suture can be routed to the distal capture jaw of any of the leaflet capture catheters disclosed herein including, for exemplary purposes, leaflet capture catheter 402. Referring to FIG. 8E, in this embodiment the suture 10 extends from a lumen 438 in the proximal clamping jaw 408, with each strand 11 of the suture extending around a channel 473 one either side of the proximal clamping jaw 408. The strands then extend up and form a loop at the distal clamping jaw for retrieval by the needle 454. The suture 10 extends back to the proximal handle control where it can be maintained under an appropriate tension for retrieval by the needle. In this embodiment, the suture lumen 438 is positioned above the needle 454 such that the suture 10 emerges from the proximal clamping jaw 408 from above the needle 454. Referring now to FIG. 8F, in this embodiment the suture 10 extends from a lumen 438 in a lower part of the proximal clamping jaw 408 below the needle 454 and wraps around the needle tube 452 containing the needle 454. Both suture ends 11 then extend along the same channel 473 on a single side of the proximal clamping jaw 408 and to the distal clamping jaw 406. The suture 10 also can then extend back to the proximal handle control. For suture capture by the needle 454, the suture 10 is released from the needle tube 452 by an actuation means, such as a control mechanism that attaches to and withdraws the tube or a wire that holds the suture on the tube and is then retracted, for example. In each of these embodiments, the suture 10 can be held in the proximal jaw by a variety of means including, for example, with features such as the distal posts 122 and intermediate tabs 126 described above.

Both of the embodiments of FIGS. 8E-8F greatly simply the suture routing and tensioning aspects of the device with respect to, for example, FIG. 4B. The suture 10 in these embodiments is no longer folded in half and can extend back to the handle, eliminating the need for the separate looped suture 20 and disengageable connection 24 as well as, in the embodiment of FIG. 8E, the proximal end suture loop 16 around the needle tube 152.

FIGS. 9A-12E depict various aspects of additional embodiments of a distal leaflet capture assembly 1102 for a leaflet capture catheter. Referring to FIGS. 9A-9B, leaflet capture assembly 1102 can generally include a shaft 1106, a proximal clamping jaw 1108 extending therefrom, a distal clamping jaw 1110 and a nose cone 1112. In one embodiment, distal clamping jaw 1110 is stationary and proximal clamping jaw 1108 is longitudinally slidable with respect to distal clamping jaw 1110 to aid in capturing a leaflet therebetween. In another embodiment, proximal clamping jaw 1108 is stationary and distal clamping jaw 1110 is slidable. Nose cone 1112 is slidable relative to distal clamping jaw 1110 and aids in suture retention and capture, as will be discussed in further detail below.

Figure 10A:
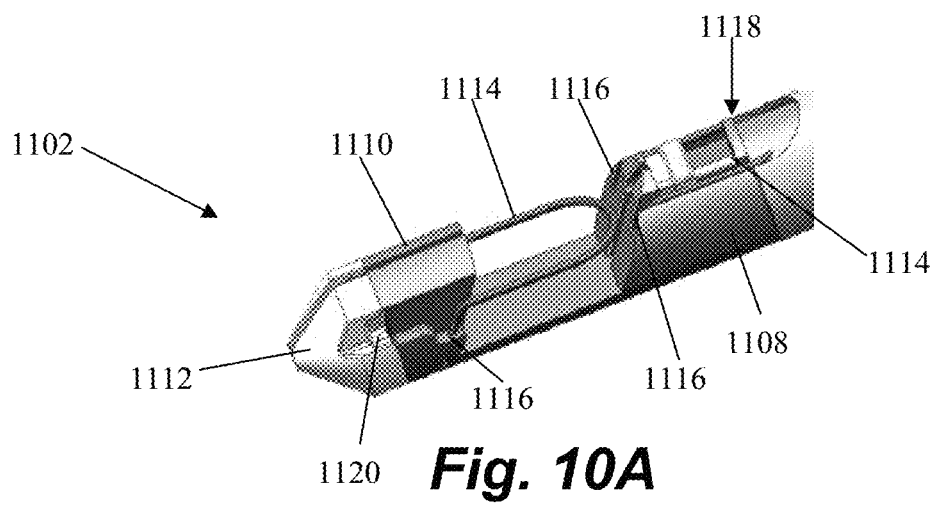
FIGS. 10A-10C depict a distal capture assembly of a leaflet capture catheter according to an embodiment.
Figure 10B:
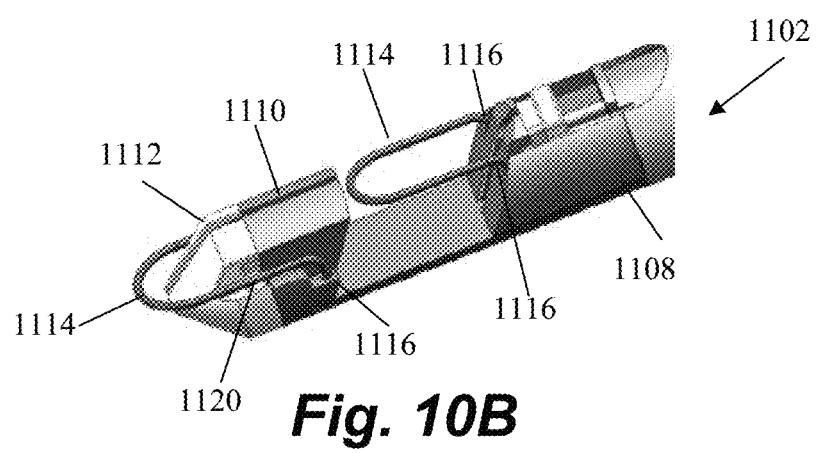
Figure 10C:
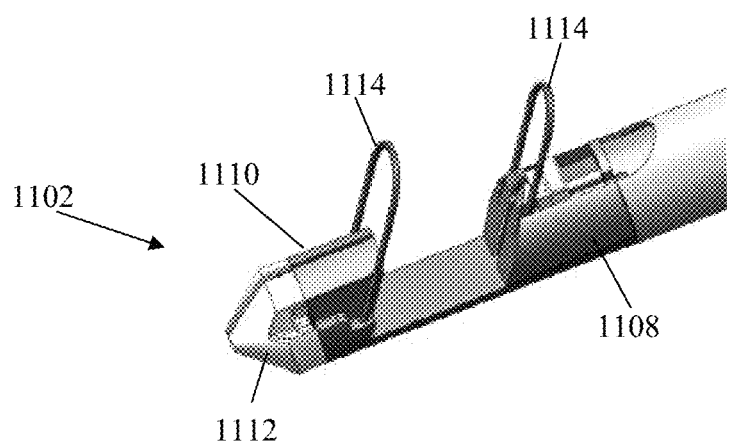

Referring to FIGS. 10A-10C, in some embodiments leaflet capture assembly 1102 can include one or more leaflet stabilizing loops 1114. A stabilizing loop 1114 can comprise a wire having opposing ends extending from openings 1116 in or adjacent the proximal clamping jaw 1108 and/or the distal clamping jaw 1110 and forming a looped shape therebetween. Stabilizing loops 1114 provide additional area for leaflet contact in order to increase the time and efficiency of leaflet capture. Stabilizing loops 1114 further provide additional support for the leaflet when the needle and suture are traversed through the leaflet. In one embodiment, as shown in FIGS. 10A-10C there are stabilizing loops 1114 on both jaws. In another embodiment, as shown in, e.g., FIGS. 11A-11B, there is a stabilizing loop 1114 only on the distal clamping jaw 1110. The one or more stabilizing loops 1114 can be collapsible such that they conform to the shape of the leaflet capture assembly 1102 as shown in, for example, FIG. 10A when contained within the guide catheters during insertion. When the leaflet capture assembly 1102 is extended from the guide catheters, the one or more stabilizing loops can passively flex outward without requiring any actuating force into a position such as that shown in FIG. 8C to provide an expanded capture and support surface for the leaflet. In one embodiment, this can be accomplished by constructing the stabilizing loops of a shape memory material such as, for example, Nitinol. When the leaflet capture assembly 1102 is withdrawn back into the guide catheters following suture deployment, the stabilizing loops can again collapse, as depicted in, for example, FIG. 8B. In this manner, stabilizing loops 1114 effectively increase the size of the capture surface of the jaws without increasing the size of the device profile. In some embodiments, proximal clamping jaw 1108, distal clamping jaw 1110 and/or nose cone 1112 can include one or more recesses 1118, grooves 1120, etc. that accommodate and/or retain a corresponding stabilizing loop 1114 in the collapsed position.

In a further embodiment, a stabilizing element as described above can be comprised of a solid portion of material rather than a wire loop and that encompasses the same area as the loop 1114. Such a stabilizing similarly serves to increase the effective capture area of the device while being collapsible so as not to increase the device profile. Such an element can be a flexible, self-actuating element similar to stabilizing loops or can in other embodiments be actuated by connection to a sliding element or rod extending to and actuated from the proximal handle control. Such a stabilizing element could in some embodiments be hinged to allow it to be brought into contact and removed from contact with the leaflet by such a sliding element actuated by the proximal handle control or by a spring force of the hinge.

As noted above, one or more stabilizing loops 1114 or elements can significantly increase the capture surface area relative to clamping jaws 1108, 1110 alone. In one embodiment, the capture surface area of clamping jaws defined by the facing clamping faces of jaws is approximately 18 mm$^2$ and when one or more stabilizing loops is deployed, the capture area provided by the combination of the jaw and the loop is approximately 52.19 mm$^2$, and increase of approximately 290% that more than doubles and nearly triples the capture surface area. Further, because stabilizing loop(s) are collapsible this increased surface area can be obtained without increasing the device profile. For example, in the described embodiment, the device profile or diameter is 18 French whereas transapical heart valve repair devices as described herein can have a diameter of 28 French.

Figure 11A:
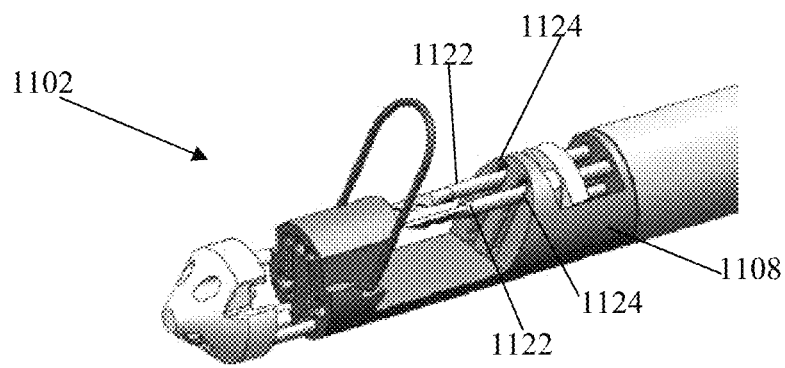
FIGS. 11A-11B depict a distal capture assembly of a leaflet capture catheter according to an embodiment and FIG. 11C depicts an embodiment of a needle for a distal capture assembly.
Figure 11B:
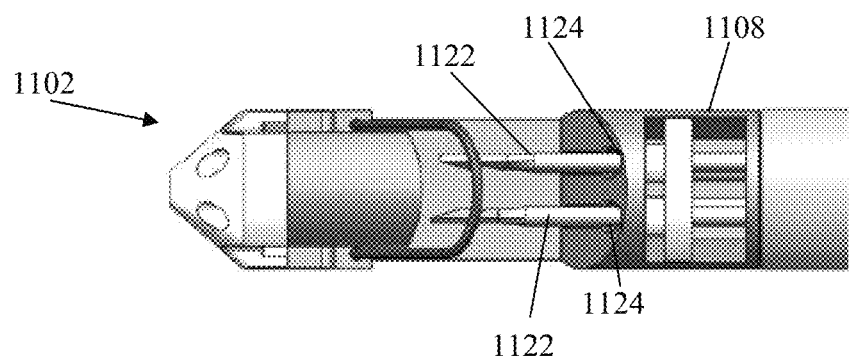
Figure 11C:
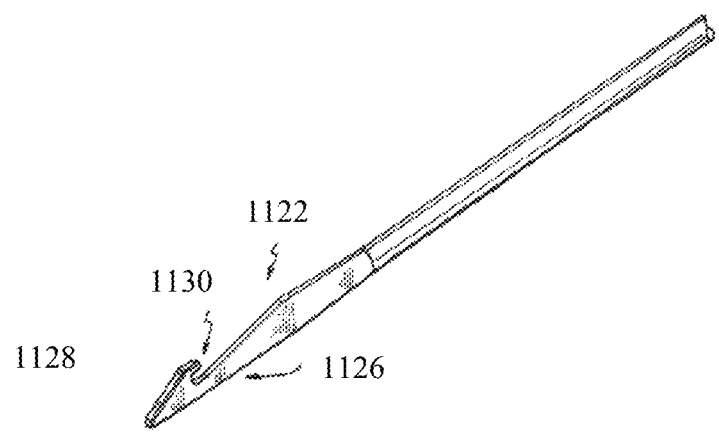

Leaflet capture assembly 1102 may further include one or more needles configured to puncture a captured leaflet and draw a suture through the leaflet. FIGS. 11A-11B depict an embodiment having a pair of needles 1122 each configured to be extended from a corresponding channel 1124 in the proximal clamping jaw 1108. As can be seen in FIG. 11C, in one embodiment each needle 1122 can include a needle end 1126 having a ramp portion 1128 and a hook forming a notch 1130. These features enable the needle end 1126 to be advanced passed a suture that is tensioned across the distal clamping jaw 1110 (discussed in more detail below) after penetrating the leaflet and withdrawn to retrieve the suture and pull it through the leaflet. As the needle end 1126 is advanced, the ramp portion 1128 of the needle 1122 will contact the suture and displace the suture slightly as it goes by without dislodging the suture. When the needle 1122 is retrieved, the suture is aligned with the notch 1130 and captured therein. Further detail regarding retrieval of a suture through a valve leaflet with such a needle can be found in U.S. Patent Publication No. 2014/0364875, which is hereby incorporated by reference herein.

Figure 12A:
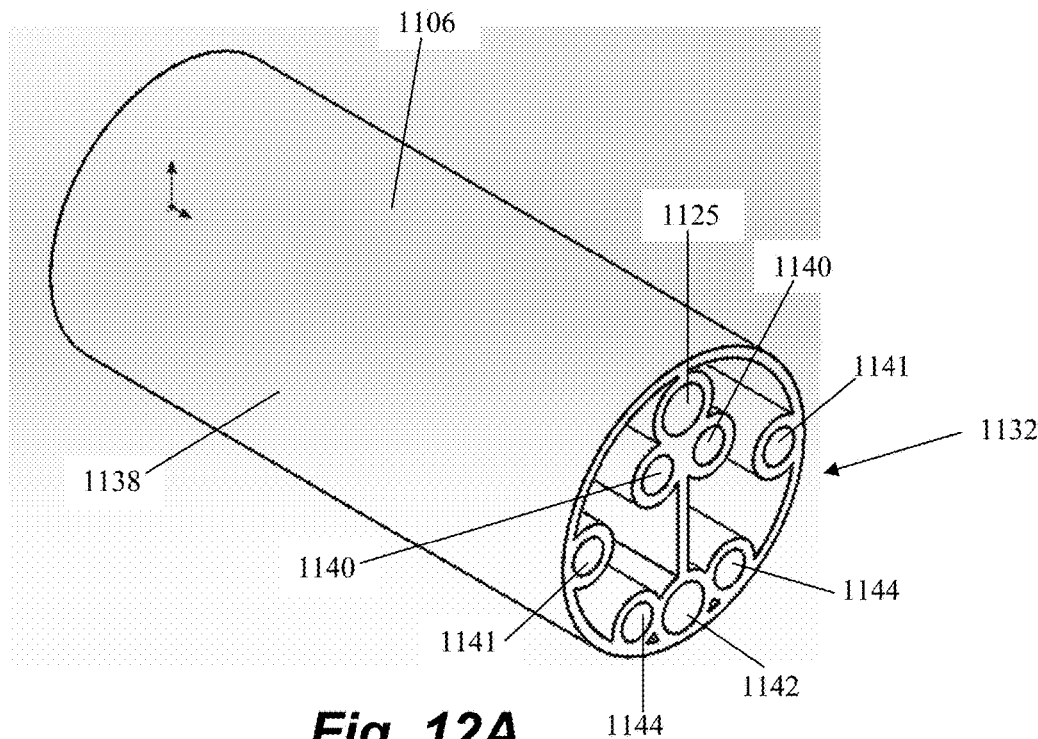
FIGS. 12A-12F depict various components of distal capture assemblies of leaflet capture catheters according to embodiments.
Figure 12B:
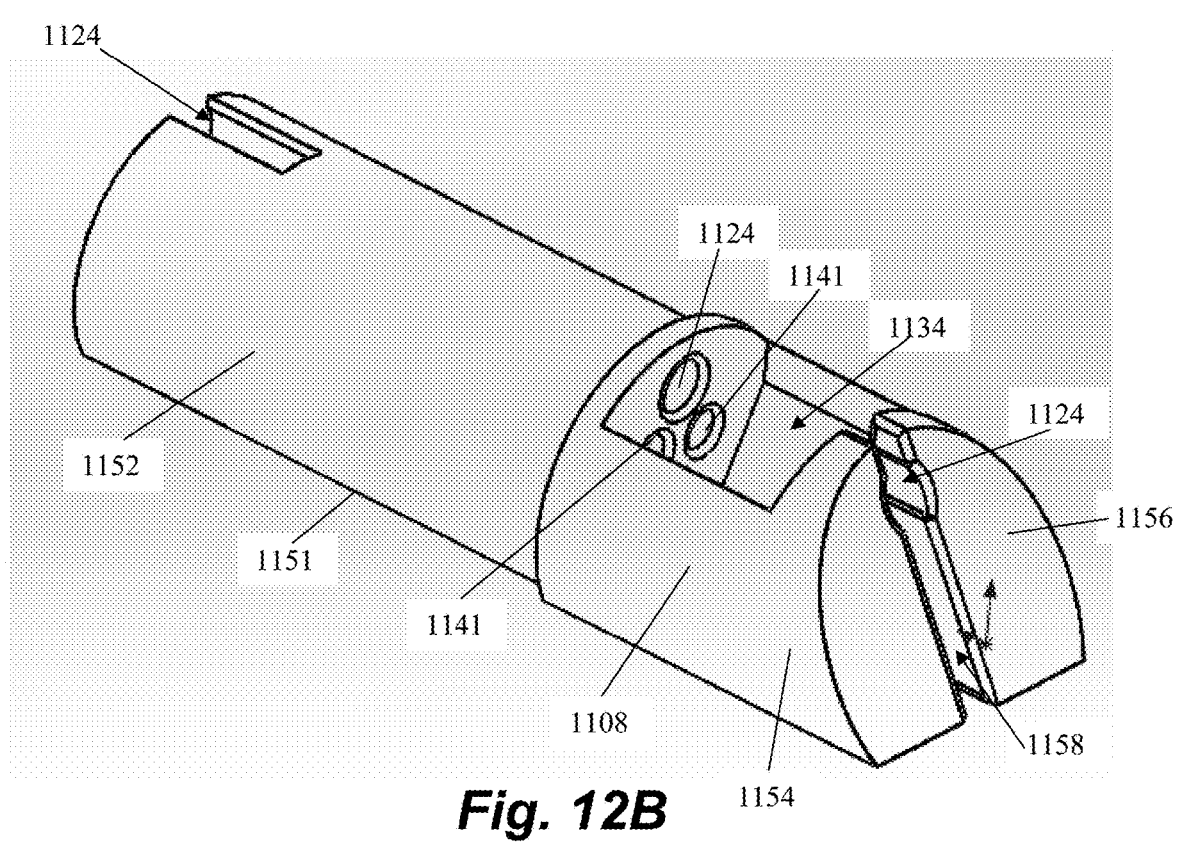
Figure 12C:
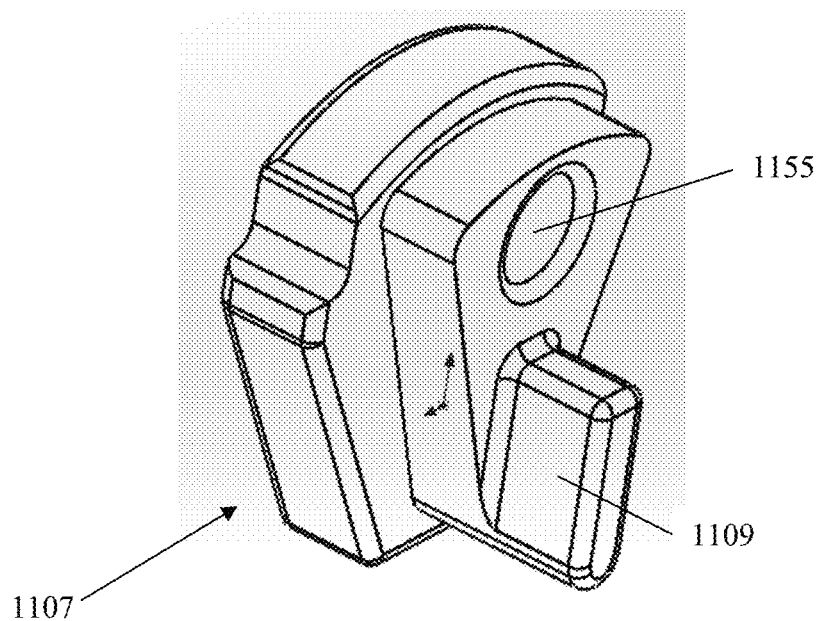
Figure 12D:
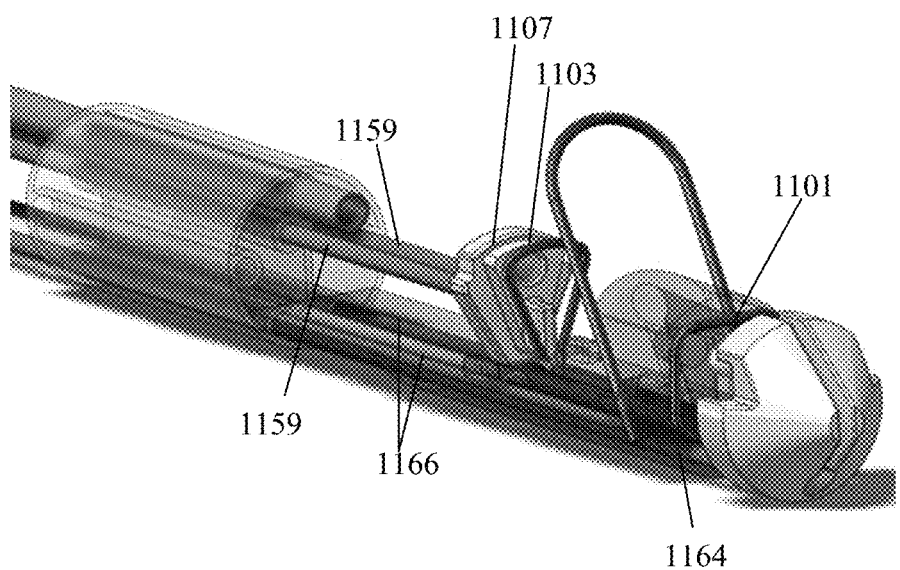
Figure 12E:
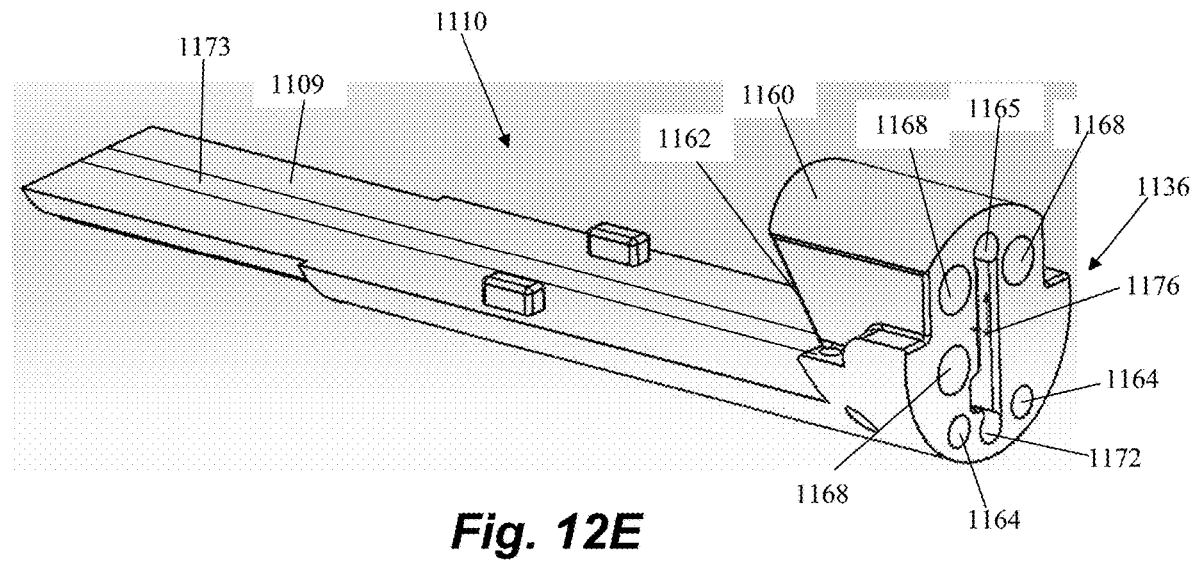
Figure 12F:
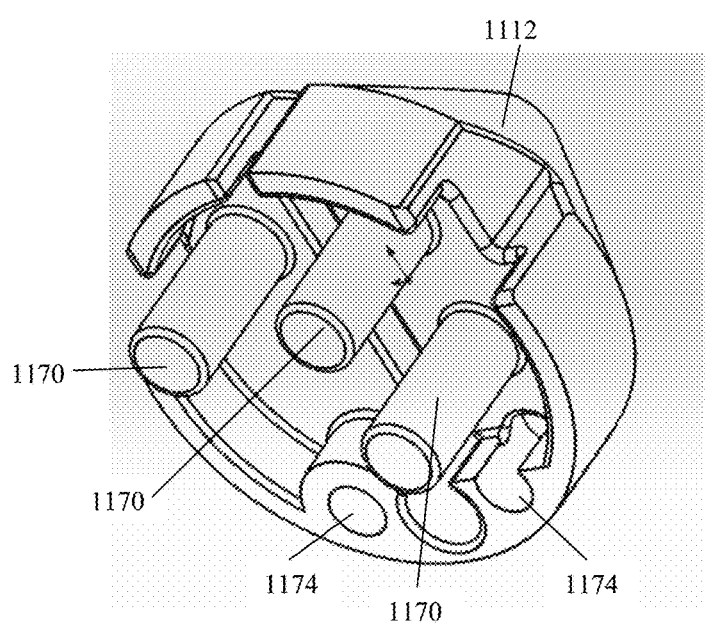
Figure 13A:
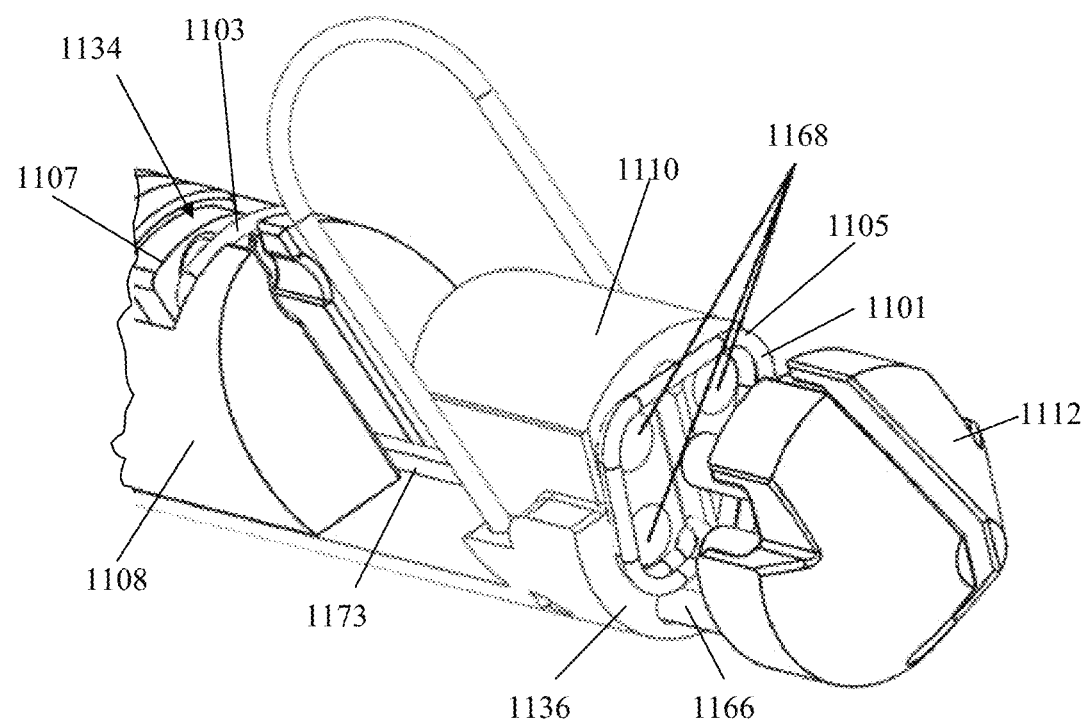
FIG. 13A-13E depict a distal capture assembly of a leaflet capture catheter according to an embodiment.
Figure 13B:
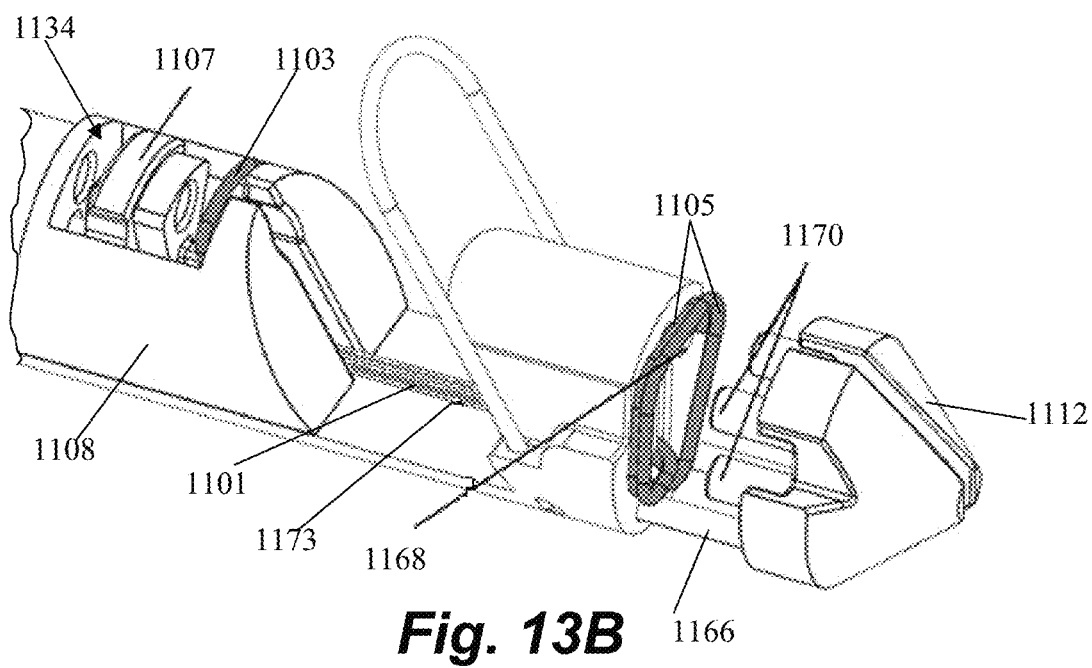
Figure 13C:
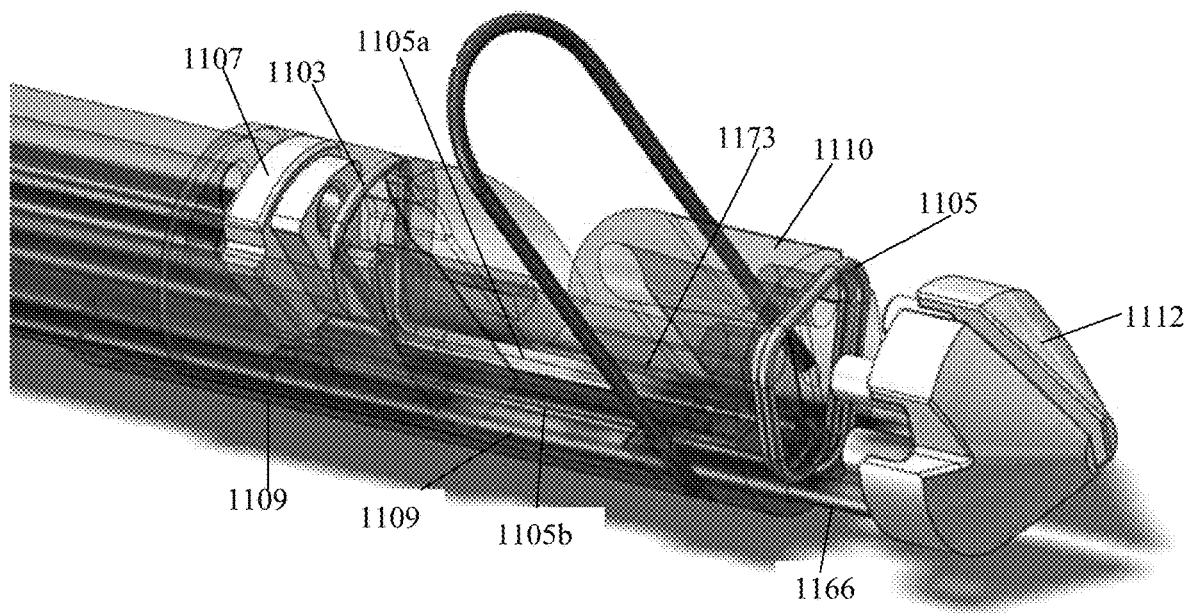
Figure 13D:
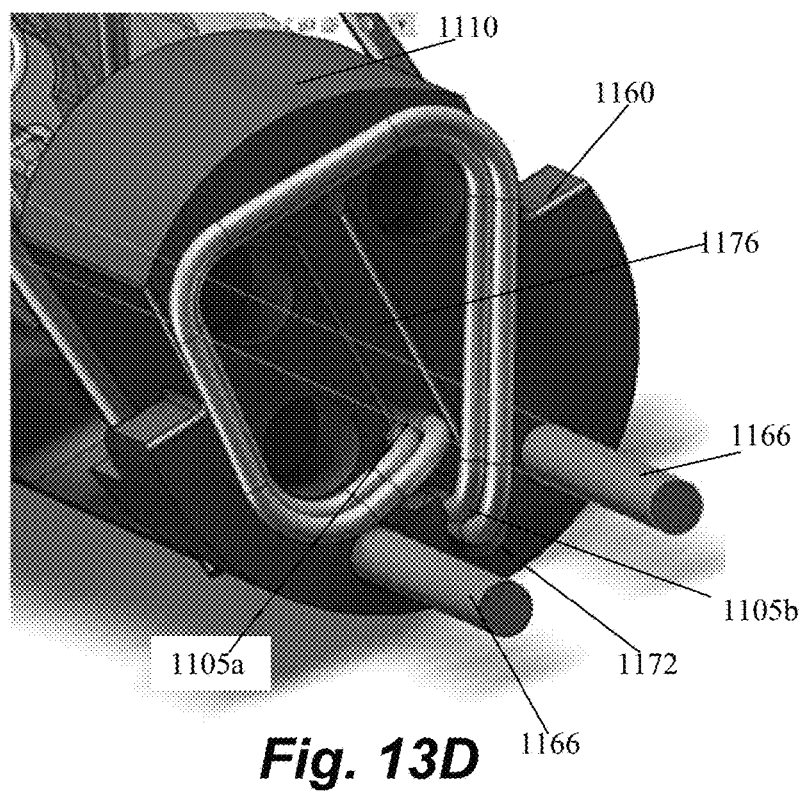
Figure 13E:
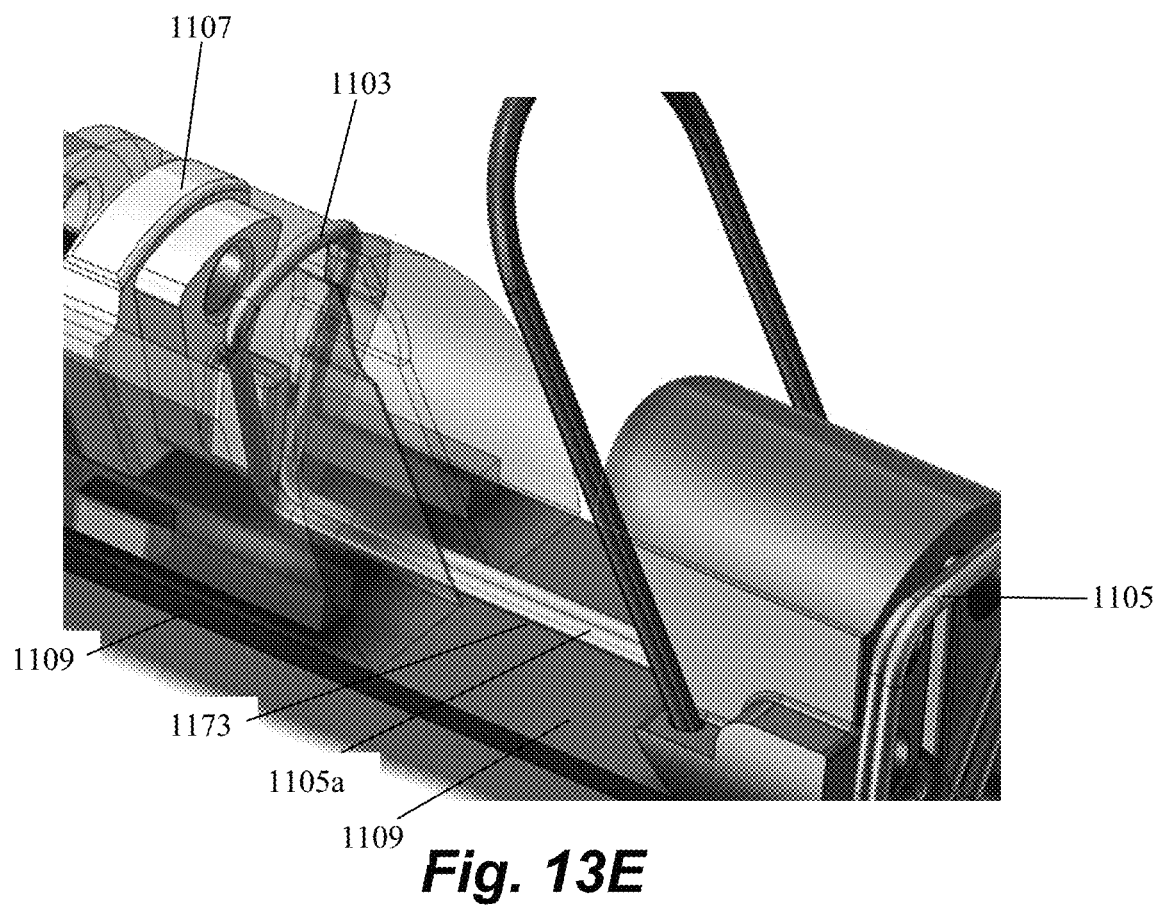

FIGS. 12A-12F, further details regarding various components of embodiments of leaflet capture assemblies 1102 are depicted. A shaft 1106 is depicted in FIG. 12A and a proximal clamping jaw 1108 configured to extend from a distal end 1132 of shaft 1106 is depicted in FIG. 12B. A suture retainer 1107 that seats within a retainer recess 1134 in proximal clamping jaw 1108 is depicted in FIG. 12C. A distal clamping jaw 1110 and corresponding nose cone 1112 configured to be positioned at a distal end 1136 of the distal clamping jaw 1110 are depicted in FIGS. 12E and 12F, respectively.

Referring now to FIG. 12A, shaft 1106 defines a generally cylindrical body 1138 and a plurality of channels or lumens that extend through the body 1138 to the distal end 1132 of the shaft. Shaft body 1138 is comprised of a flexible material to enable the shaft 1106 to be routed through the guide catheters in the patient's vasculature. Channels can include one or more needle channels 1125 through which a needle 1122 can be inserted from a proximal end of the shaft to be extended out of the distal end 1132 of the shaft 1125 and through which needle 1122 can be withdrawn after retaining a suture. Suture retainer rod channels 1140 adjacent the needle channel 1125 are configured to guide rods that extend to and control positioning of the suture retainer 1107, as will be described in more detail below. A suture channel 1142 is configured to contain and guide a suture 1101 through the device prior to retrieval of the suture by the needle 1122. Channels can further include nose cone control channels 1144 through which rods that extend to and control positioning of the nose cone 1112 are guided. In some embodiments, shaft 1106 may further include a channel or lumen through which a rod or rods for controlling movement of the proximal clamping jaw 1108, as described below, can extend. Alternatively, the proximal clamping jaw control rod(s) can extend through the shaft through one or more open areas between the channels depicted in FIG. 12A. In some embodiments, shaft 1106 further includes one or more stabilizing rods 1141 that provide structural reinforcement for the flexible shaft 1106.

An embodiment of a proximal clamping jaw 1108 is depicted in FIG. 12B. Proximal clamping jaw 1108 includes a proximal shaft body 1150 and a proximal jaw body 1152. Body 1150 and jaw 1152 can partially confirm to the shape of the shaft 1106 and include a generally planar bottom surface 1151 that interfaces with distal clamping jaw 1110. Proximal jaw body 1152 includes a retainer recess 1134 configured to receive proximal suture retainer 1107 (depicted in more detail in FIG. 10C). A needle channel 1124 aligns with the needle channel 1125 of the shaft 1106 and extends through the proximal shaft body 1150 and the proximal jaw body 1152. Retainer rod channels 1141 extend through body 1150 and align with retainer rod channels 1140 of shaft 1106 to accommodate suture retainer rods 1159 use to control the suture retainer 107 as described below. Proximal jaw body 1152 defines a distally facing clamping face 1156 and further defines a slot 1158 extending from the needle channel 1124 along the clamping face 1156.

FIG. 12C depicts an embodiment of suture retainer 1107 configured to be disposed within the retainer recess 1134 of the proximal clamping jaw 1106. Suture retainer 1107 includes a needle channel 1155 configured to enable passage of the needle 1125 and connects to one or more suture retainer rods 1159, as shown in, e.g., FIG. 12D. As can further be seen in FIG. 12D, a loop 1103 of suture 1101 can be positioned adjacent the suture retainer 1107 and clamped within retainer recess 1134 of proximal clamping jaw 1108 by clamp 1109 to secure a loop 1103 of the suture 1101 in place prior to retrieval of the suture with the needle 1122. As will be described below, the suture retainer 1107 can be moved proximally via rods 1159 to release the suture 1101.

An embodiment of a distal clamping jaw 1110 is depicted in FIG. 12E. Distal clamping jaw includes jaw shaft 1109 and clamping body 1160. Jaw shaft 1109 interfaces with bottom 1151 of proximal clamping jaw 1108 to form a generally cylindrical profile. Clamping body 1160 includes a proximally facing clamping face 1162 and a needle channel 1165 that is aligned with needle channels 1124, 1125 and 1155 to enable the needle 1122 to be able to travel through clamping body 1160. A suture lumen 1172 is also defined through clamping body 1160 and a slot 1176 can extend through the clamping body 1160 between the needle channel 1165 and the suture channel 1168. Suture lumen 1172 can extending internally through jaw shaft 1109 and align with suture lumen 1142 though shaft 1106. Slot 1176 can interface with suture channel 1173 in jaw shaft 1109.

The nose cone 1112, an embodiment of which is depicted in FIG. 12F, can be selectively positioned with respect to the distal clamping jaw 1110 by a pair of nose cone control rods 1166 that extend through the nose cone control channels 1144 in the shaft 1106 and into and through jaw nose cone channels 1164 through the jaw shaft 1109 and clamping body 1160 of the distal clamping jaw 1160. The nose cone control rods 1166 attached to the nose cone 1112 in corresponding nose cone channels 1174 to enable control of the relative positioning of the nose cone 1112 with respect to the distal clamping jaw 1110. The nose cone 1112 can further include a plurality of suture rods 1170 that can be selectively positioned within corresponding suture rod channels 1168 in the clamping body 1160 of the distal clamping jaw 1110. In other embodiments, nose cone 1112 can be opened by a spring force when actuated and/or by a hinged attachment to the distal clamping jaw 1110. Nose cone 1112 in the depicted embodiment has generally conical shape due to its location at the distal-most end of leaflet capture catheter to provide an atraumatic shape for insertion into the delivery system and the heart. However, nose cone can be provided with different shapes and, in some embodiments, could be positioned proximal to clamping body 1160 of distal clamping jaw 1110 rather than distal, as the primary function of the nose cone is to hold the suture in place to be engaged by the needle.

FIGS. 13A-13E depict in further detail the manner in which a suture 1101 is contained by the distal capture assembly 1102 of the leaflet capture catheter 1100 prior to retrieval of the suture 1101 according to an embodiment. Suture 1101 includes a suture loop 1103 in the retainer recess 1134 adjacent the suture retainer 1107 and a pair of suture strands 1105 adjacent the distal end 1136 of the distal clamping jaw 1110 between the distal clamping jaw 1110 and the nose cone 1112. The suture loop 1103 is retained in the retainer recess 1134 by the suture retainer 1107 with a first length of the two suture strands 1105a extending along the channel 1173 through the slot 1176 in the distal end 1136 of the distal clamping jaw 1110, where they are wrapped around the suture rods 1170 of the nose cone 1112 in tension to aid in capture by the needle 1122. Suture strands 1105 are held in place around suture rods 1170 by compression between the nose cone 1112 and the distal end 1136 of the distal clamping jaw 1110. (Note that for clarity in these Figures the nose cone is shown displaced from the distal clamping jaw 1110, but in the described initial configuration the suture rods 1170 would be inserted into suture rod channels 1168 with the suture 1101 held securely therebetween.) A second length of the suture strands 1105b then extends back through the internal suture lumen 1172 of the distal clamping jaw 1110 and is subsequently routed through the suture channel 1142 in the shaft 1106 (See FIG. 12A). In an alternative embodiment, the suture can consist of a loop of suture at the end of a single suture strand. Such a loop would be sized specifically to enable fixation around an edge of the leaflet with the single strand extending from the loop/leaflet to the anchor point below the leaflet.

After a leaflet has been captured between the jaws 1108, 1110, the needle end 1126 of needle 1122 is advanced through needle channels 1124, 1125, 1155 and 1165 past the suture 1101 as described above and then retracted to retrieve the suture 1101 in the notch 1130 of the needle end 1126. The nose cone 1112 can then be advanced distally to release the suture ends 1105 held there and the suture ends 1155 are pulled back through the suture loop 1103 with the needle 1122. The suture retainer 1107 is then retracted proximally to release the suture loop 1103, enabling the loop 1103 to be tightened around the leaflet in a girth hitch knot as the suture ends 105 are further withdrawn and the device externalized. Further details regarding formation of such knots around heart valve leaflets can be found in U.S. Patent Publication No. 2017/0290582, which is hereby incorporated by reference herein.

FIGS. 14A-14G depict a proximal handle control 1104 for a leaflet capture catheter according to an embodiment. Proximal handle control 1104 is used to control and manipulate the distal leaflet capture assembly 1102 and can include a handle body 1180 and a suture retainer control 1182, a nose cone control 1184 and a clamping jaw control 1186. A needle 1122 can be inserted through device and manually controlled with needle control 1188. FIGS. 14B-14G show the device with portions of the device removed from each Figure for sake of clarity.

Figure 14A:
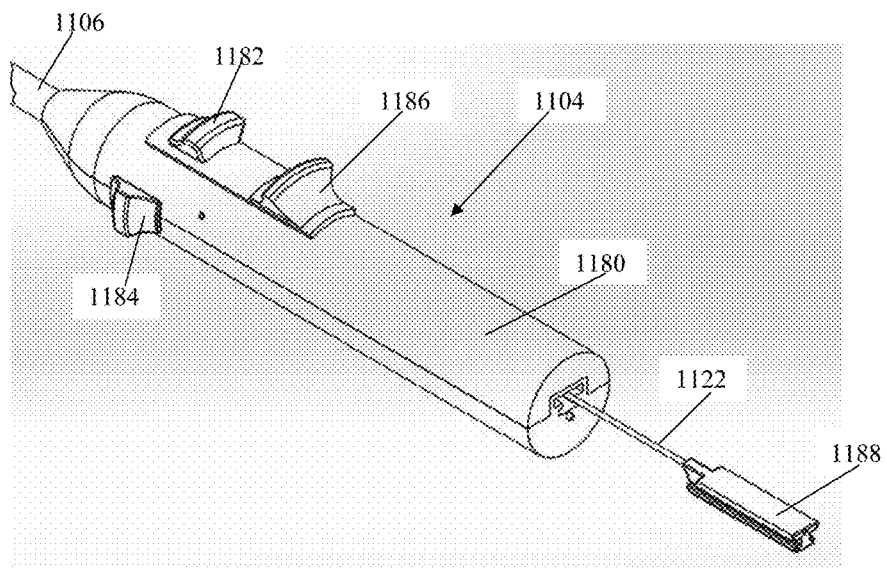
FIGS. 14A-14H depict a control handle of a leaflet capture catheter according to an embodiment.
Figure 14B:
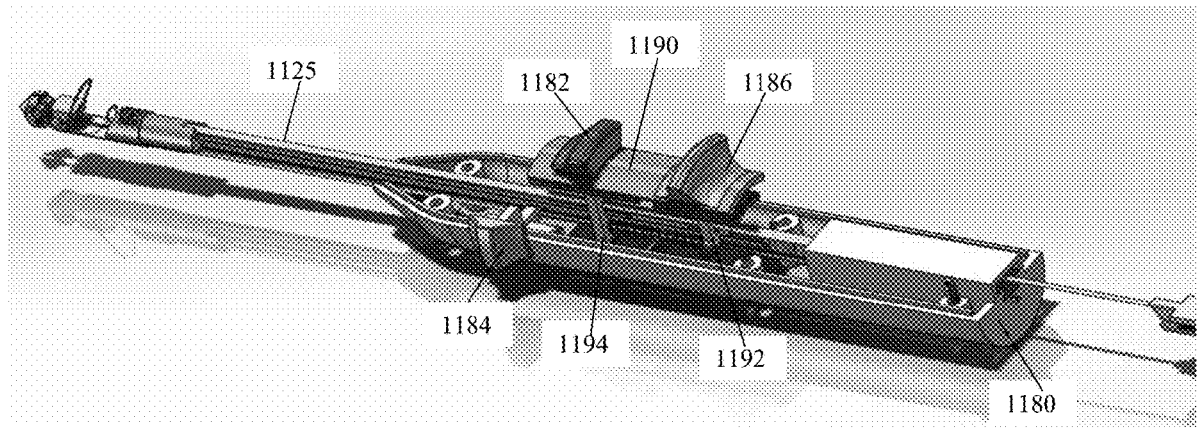
Figure 14C:
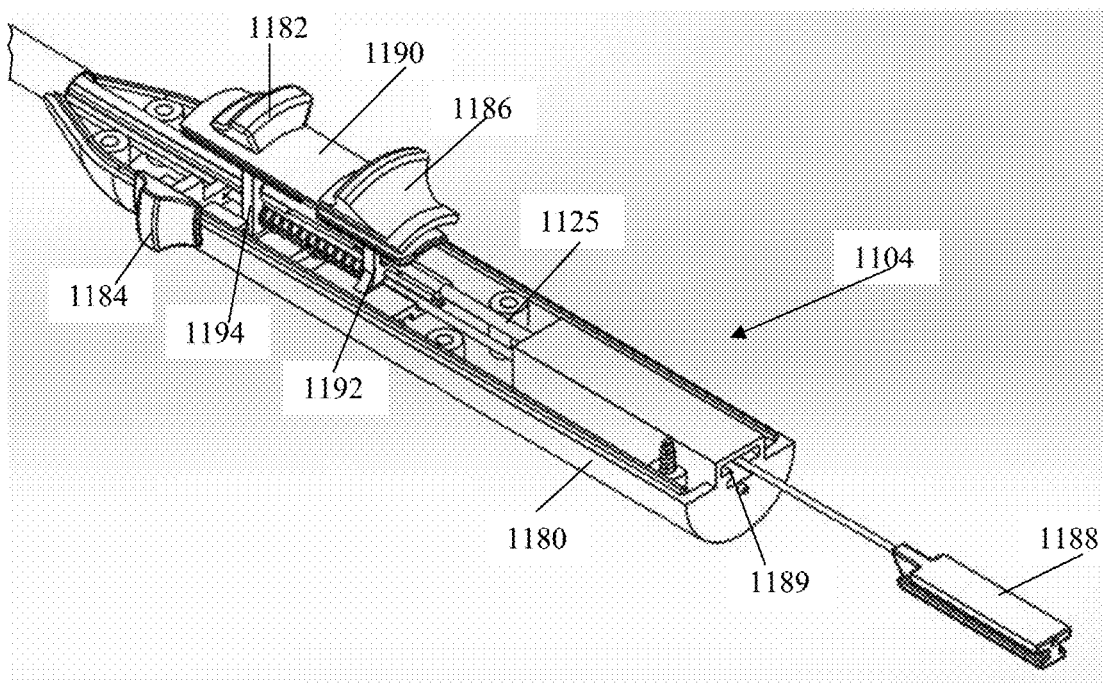
Figure 14D:
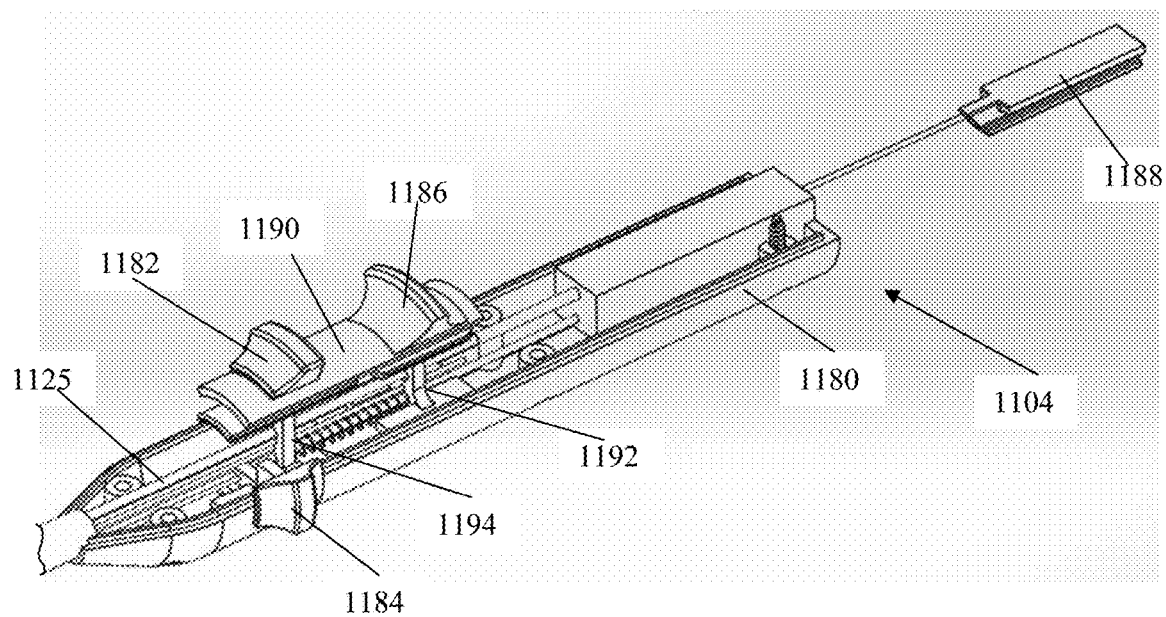

FIG. 14B-14D depict handle 1104 with a portion of handle body 1180 removed in order to further illustrate the interrelation between the various control elements in the handle 1104. Clamping jaw control or lever 1186 and suture retainer control or lever 1182 are each connected to an independently movable lever support 1192, 1194 that separately control the corresponding rods controlled by each control lever. Clamping jaw lever 1186 includes a lever body 1190 above which the suture retainer lever 1182 seats and through which the suture retainer lever support 1194 extends. Supports 1192, 1194 each further include apertures through which the needle lumen 1125 extends and which enable the suture retainer lever 182 and the clamping jaw lever 1186 to slide over and move independently of needle lumen 1125. As will be seen below, clamping jaw lever 1186 is only able to then move distally a relatively short amount before clamping jaw lever support 1192 contacts the suture retainer lever support 1194 (see, e.g., FIG. 14F), causing the proximal jaw 1108 and the suture retainer 1107 to move distally in unison with each other. This provides the advantage of keeping the suture loop 1103 firmly clamped by the suture retainer 1107 as the proximal jaw 1108 is advanced to grasp a leaflet.

Figure 14E:
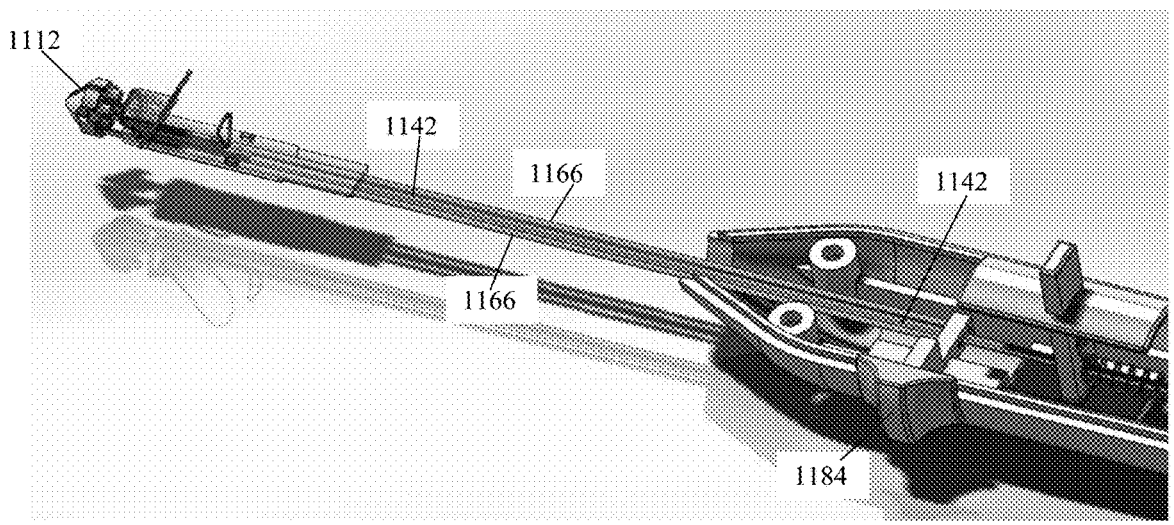

FIG. 14E depicts the elements related to the nose cone control or lever 1184. The nose cone control or lever 1184 is operably connected to nose cone control rods 1166 to advance and retract the nose cone 1112 relative to the distal clamping jaw 1100. Suture lumen 1142 extends through a portion of the nose cone lever 1184 and between nose control rods 1166 (See FIG. 12A). Nose cone lever 1184 slides over the suture lumen 1142 when operated to move the nose control rods 1166 such that the suture lumen 1142 is not controlled by the nose cone lever 1184. Moving the nose cone 1112 away from the distal jaw 1110 to create a space therebetween enables the suture 1101 to be released from around the suture rods 1170 of the nose cone 1112 as described above.

Figure 14F:
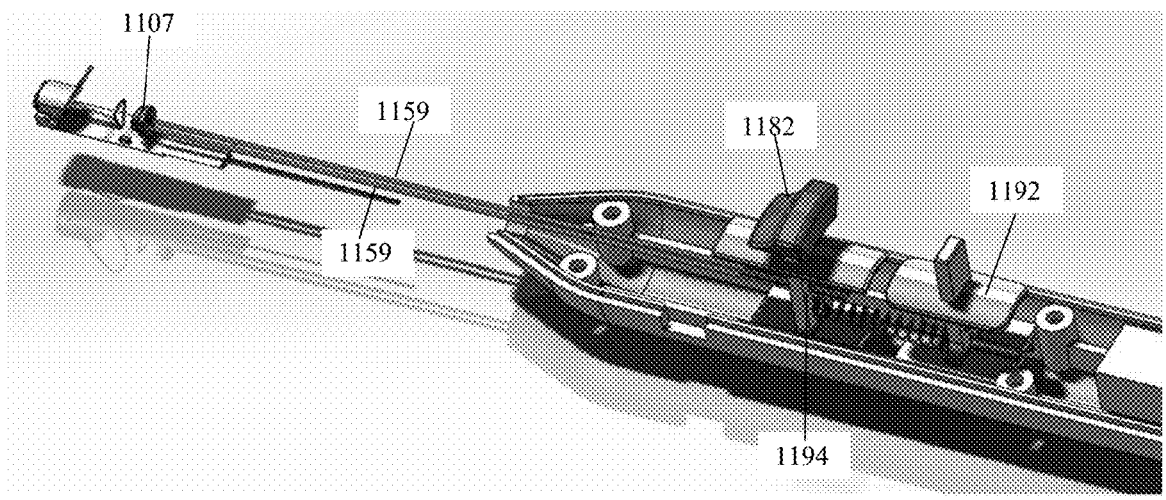

Further details relating to the suture retainer lever 1182 can be seen in FIG. 14F. Suture retainer lever 1182 is operably connected to suture retainer rods 1159 to move the proximal suture loop retainer 1107 within suture retainer recess 1134 of proximal clamping jaw 1108. In the depicted embodiment, suture retainer rods 1159 are affixed to the base of the suture retainer lever support 1194. Suture retainer lever 1182 can be moved distally to advance the suture retainer 1107 via suture retainer rods 1159 to firmly clamp the suture loop 1103 as described above. Subsequent proximal movement of the suture retainer level 1182 moves the suture retainer 1107 proximally, which, as described above, releases the suture loop to enable the girth hitch knot to be tightened around the leaflet edge.

Figure 14G:
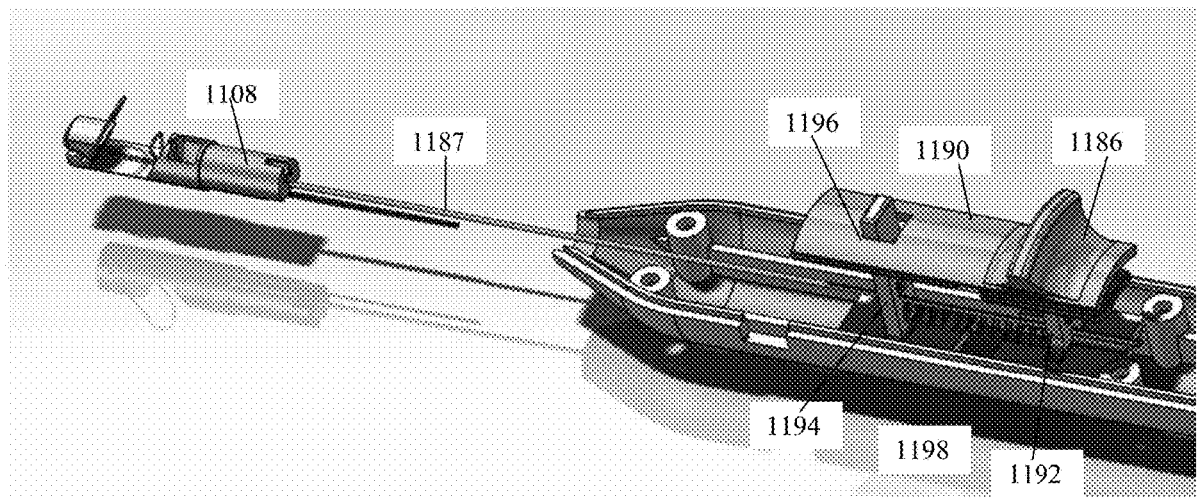

FIG. 14G depicts further details regarding the clamping jaw lever 1186 used to control the proximal clamping jaw 1108. Lever body 1190 includes an opening 1196 through which suture retainer lever support 1194 extends and that is larger than the portion of the lever support 1194 that extends therethrough to enable independent movement of the suture retainer lever 1182. A clamping jaw rod 1187 extends from clamping jaw lever support 1192 to the proximal clamping jaw 1108 such that distal and proximal movement of the clamping jaw lever 186 causes a corresponding movement of the jaw 1108. In the depicted embodiment, a spring 1198 is disposed between the clamping jaw lever support 1192 and the suture retainer lever support 1194. This causes the proximal clamping jaw 1108 to be biased proximally, such that distal movement of the clamping jaw lever 1186 must overcome the spring force to close the space between the jaws 1108, 1110 and upon releasing the lever 1186 the proximal clamping jaw 1108 will automatically spring proximally back to a more open position. Correspondingly, spring 1198 will cause the suture retainer lever 1196 to be biased distally. In another embodiment, the proximal clamping jaw 1108 is distally biased into a closed position with respect to the distal clamping jaw 1110, such that the clamping jaw lever 1186 must be actuated to open the jaws and then the jaws will automatically close when the lever 1186 is released.

Figure 14H:
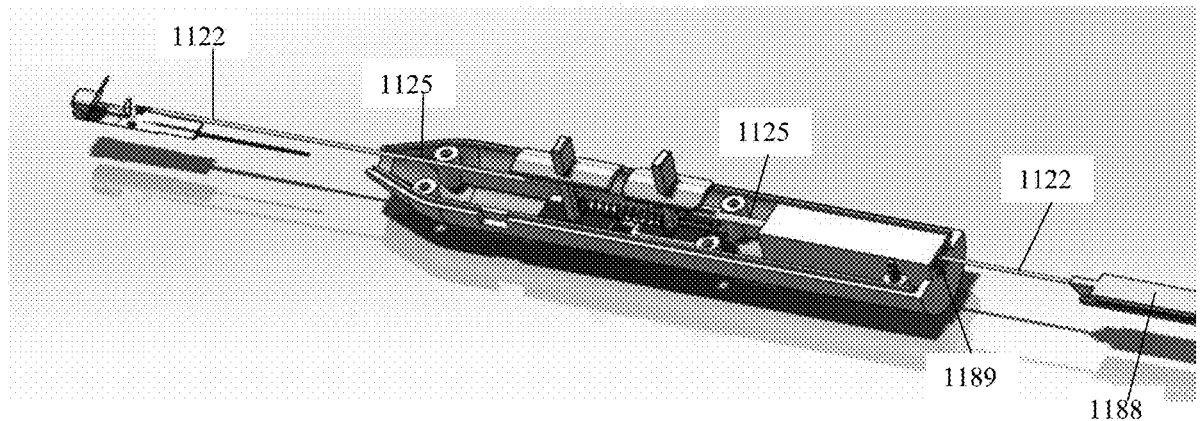

The needle 1122, as shown in FIG. 14H, extends through needle lumen 1125 and is manually controlled by a user with the needle handle 1188. Needle handle 1188 is provided with an asymmetric shape configured to match a shape of an opening 1189 in handle 1104 (see also FIG. 14C). This ensures that the needle 1122 is in the correct orientation to capture the suture when actuated (as described above).

Figure 15B:
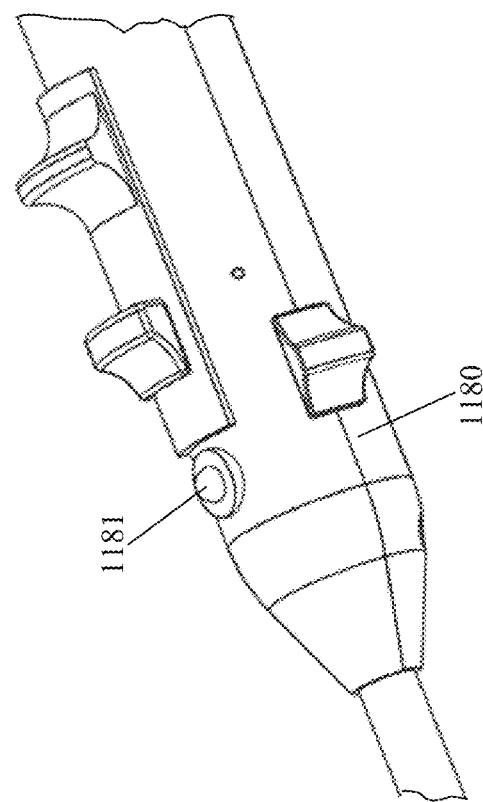
FIGS. 15A-15B depict a control handle of a leaflet capture catheter according to an embodiment.
Figure 15A:
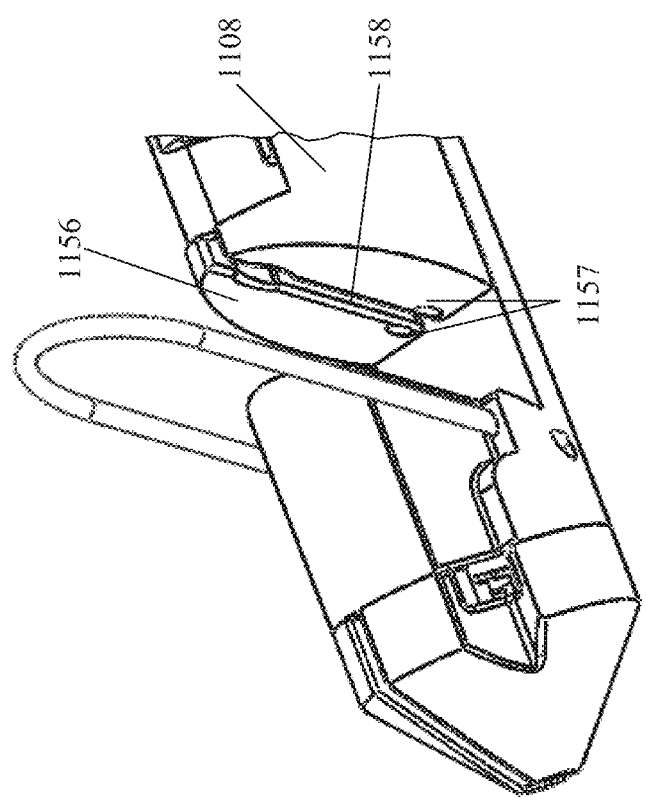

In some embodiments, one or more channels through the device could alternatively accommodate or could additionally be added to incorporate fiber optic capture confirmation elements. In such an embodiment, one or more pairs of transmission and return fibers run through the device to enable the capture confirmation system to provide a binary indication of whether the valve leaflet is grasped between the clamping jaws by displaying a first color when a surface of the valve leaflet confronts the fiber optic pairs and a second color (e.g., of blood) when the valve leaflet does not confront the fiber optic pairs at the interior surfaces. FIGS. 12A-12B depict one such embodiment. Referring to FIG. 15A, one or more fiber optic channels 1157 can be provided along the slot 1158 in the clamping face 1156 of the proximal clamping jaw 1108. As depicted in FIG. 15B, one or more indicator lights 1281 can be provided on handle body 1280 of proximal handle control to provide one or more indications of whether or not the leaflet is captured between the clamping jaws from the fiber optics extending through the channels 1257. Further detail regarding fiber optic capture confirmation of a valve leaflet in a beating heart of a patient can be found in U.S. Pat. Nos. 8,465,500 and 8,758,393, previously incorporated herein by reference.

Figure 16:
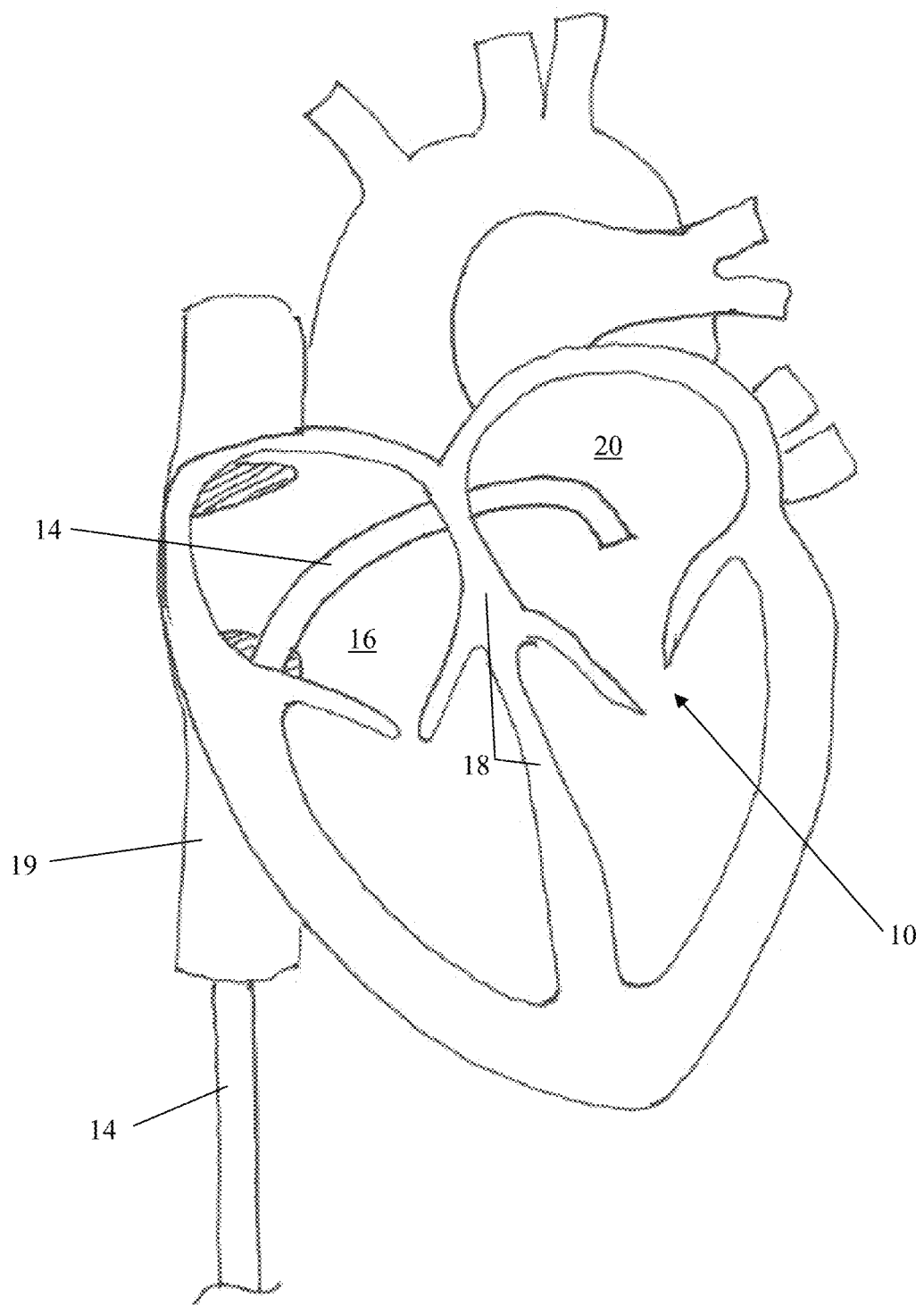
FIG. 16 is a schematic representation of a method for inserting a leaflet capture catheter into a beating heart of a patient according to an embodiment.

In various embodiments, leaflet capture catheters as described herein are configured to access the heart intravascularly for leaflet repair. FIG. 16 depicts a schematic representation of an embodiment of an access approach for a heart valve repair system including a leaflet capture catheter accessing the mitral valve 10. FIG. 16 depicts a guide catheter 14 accessing the interior of the heart via the femoral vein. In some embodiments, such a system can further include an outer guide catheter and an inner guide catheter. In such embodiments, the outer guide catheter can be inserted into the femoral vein at the patient's groin and advanced through the femoral vein into the inferior vena cava 19 and then into the right atrium 16. In various embodiments, the outer guide catheter can be steerable in a single plane and can have an outer diameter of 24 french. The septum 18 can then be punctured using an appropriate puncture tool and the outer guide catheter advanced into the septum 18 or through the septum 18 into the left atrium 20. The inner guide catheter can then be axially advanced through the outer guide catheter into the left atrium 20. In some embodiments, the inner guide catheter can have two plans of steerability and can be maneuvered along with and/or beyond the outer guide catheter to establish a stable position superior to the mitral valve 10 and to provide a desired trajectory for operation of the leaflet capture catheter 100 (not pictured in FIG. 16) to repair the valve, as discussed below.

Figure 17A:
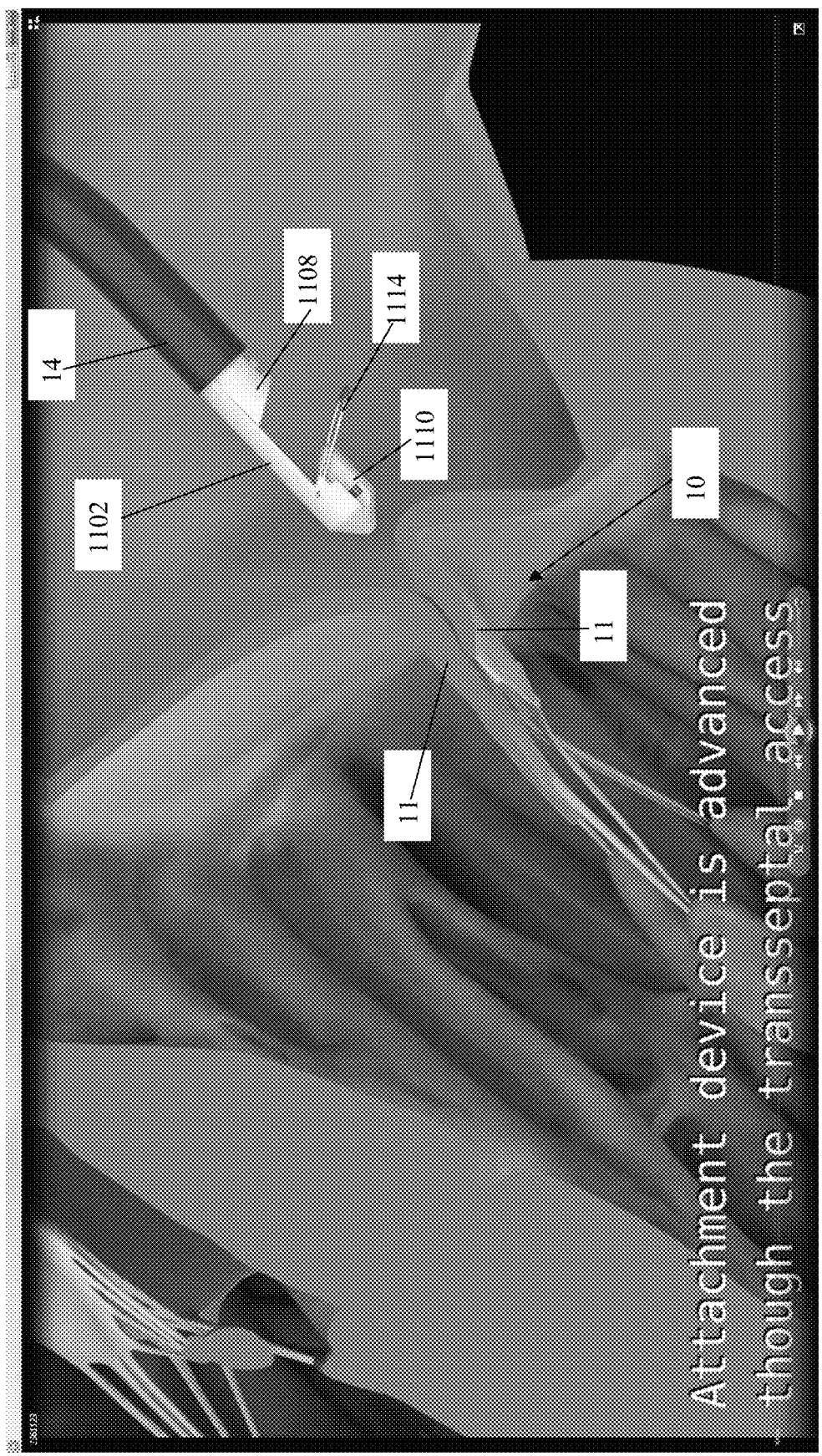
FIGS. 17A-17G depict various steps in a method of inserting a suture in a beating heart of a patient to function as an artificial chordae according to an embodiment.
Figure 17B:
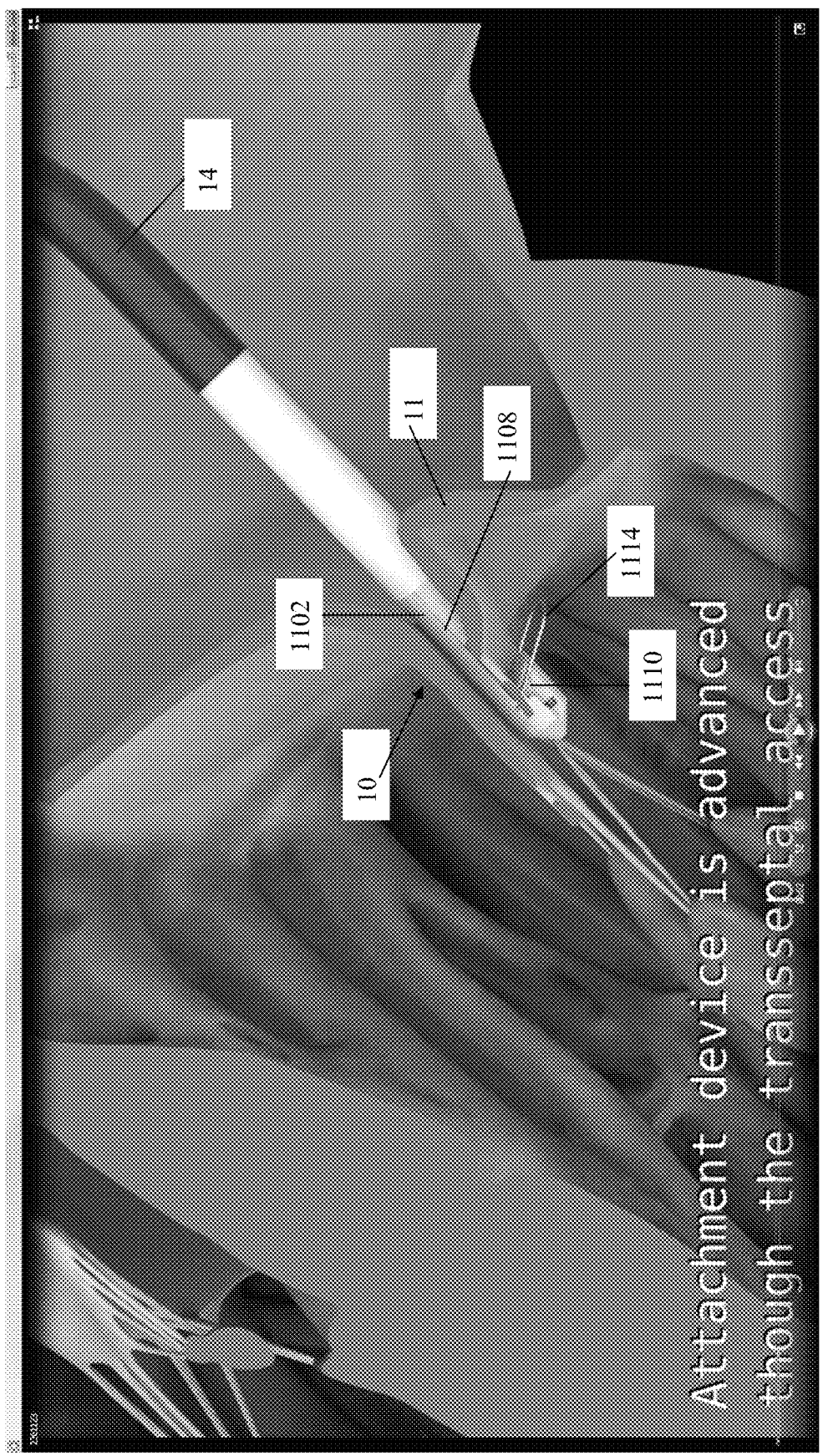
Figure 17C:
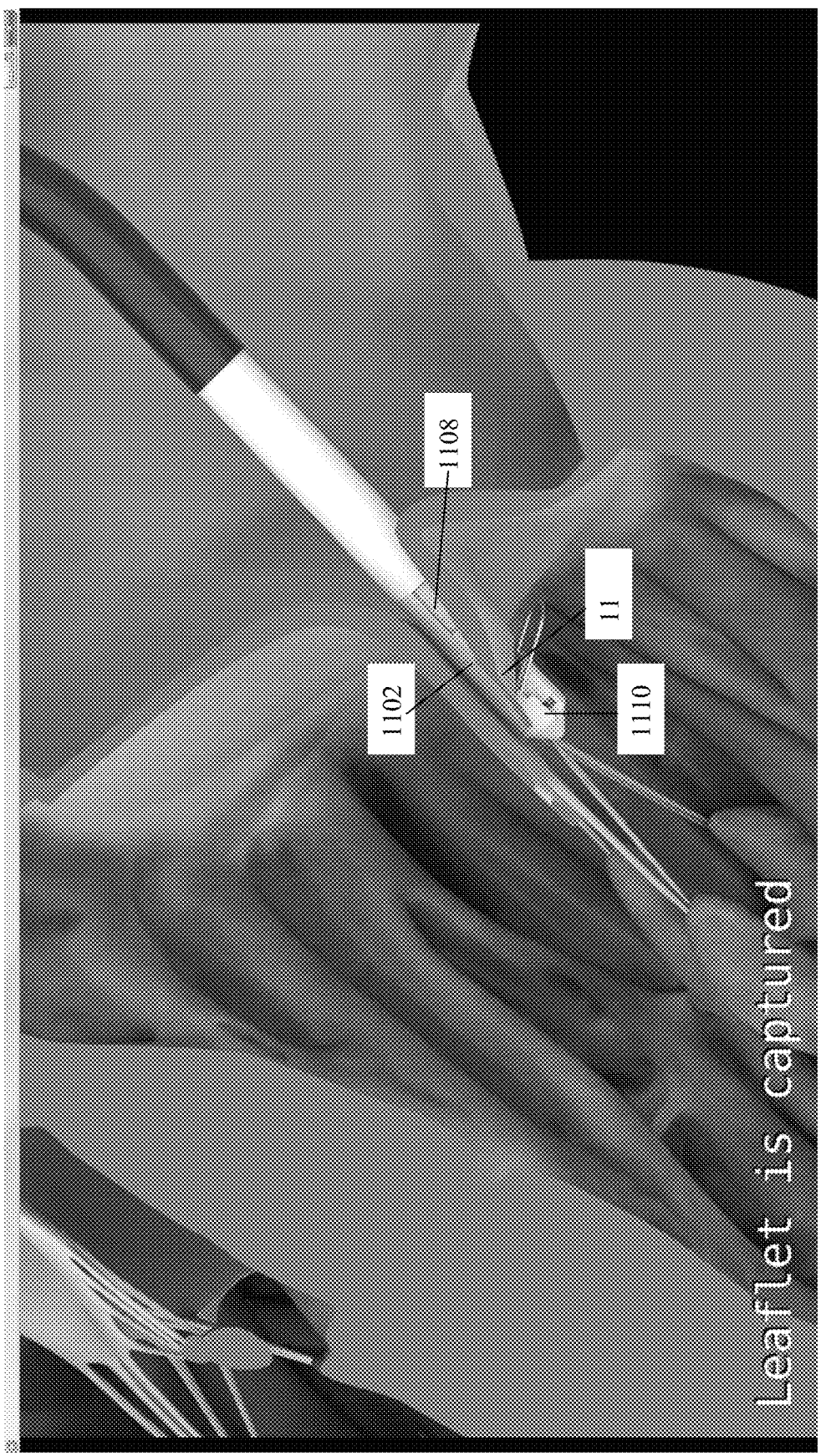

Schematic representations of various steps of a method of repairing a heart valve by inserting a suture into a valve leaflet with a leaflet capture catheter 102, 1102 as described herein are depicted in FIGS. 17A-17G. In one embodiment, leaflet capture catheter 1102 is preloaded with a suture positioned as described above. Referring to FIG. 17A, after transseptal access to the right atrium is obtained, for example as described above with respect to FIG. 14, the leaflet capture catheter 1102 is positioned superior to the mitral valve 10. As the distal capture assembly is extended from the guide catheter 14, the stabilizing loop 1114 automatically transitions from its collapsed position to its extended position because it is no longer constrained by the guide catheter 14. The distal capture assembly 1102 can be further advanced to position the distal clamping jaw 1110 and the proximal clamping jaw 1108 around a leaflet 11 as shown in FIG. 17B, with the stabilizing loop 1114 helping to guide and restrain the leaflet 11 between the jaws 1108, 1110. The proximal clamping jaw 1110 can then be advanced by actuating the clamping jaw lever 1186 to clamp the leaflet 11 between the jaws 1108, 1110 as shown in FIG. 17C.

Figure 17D:
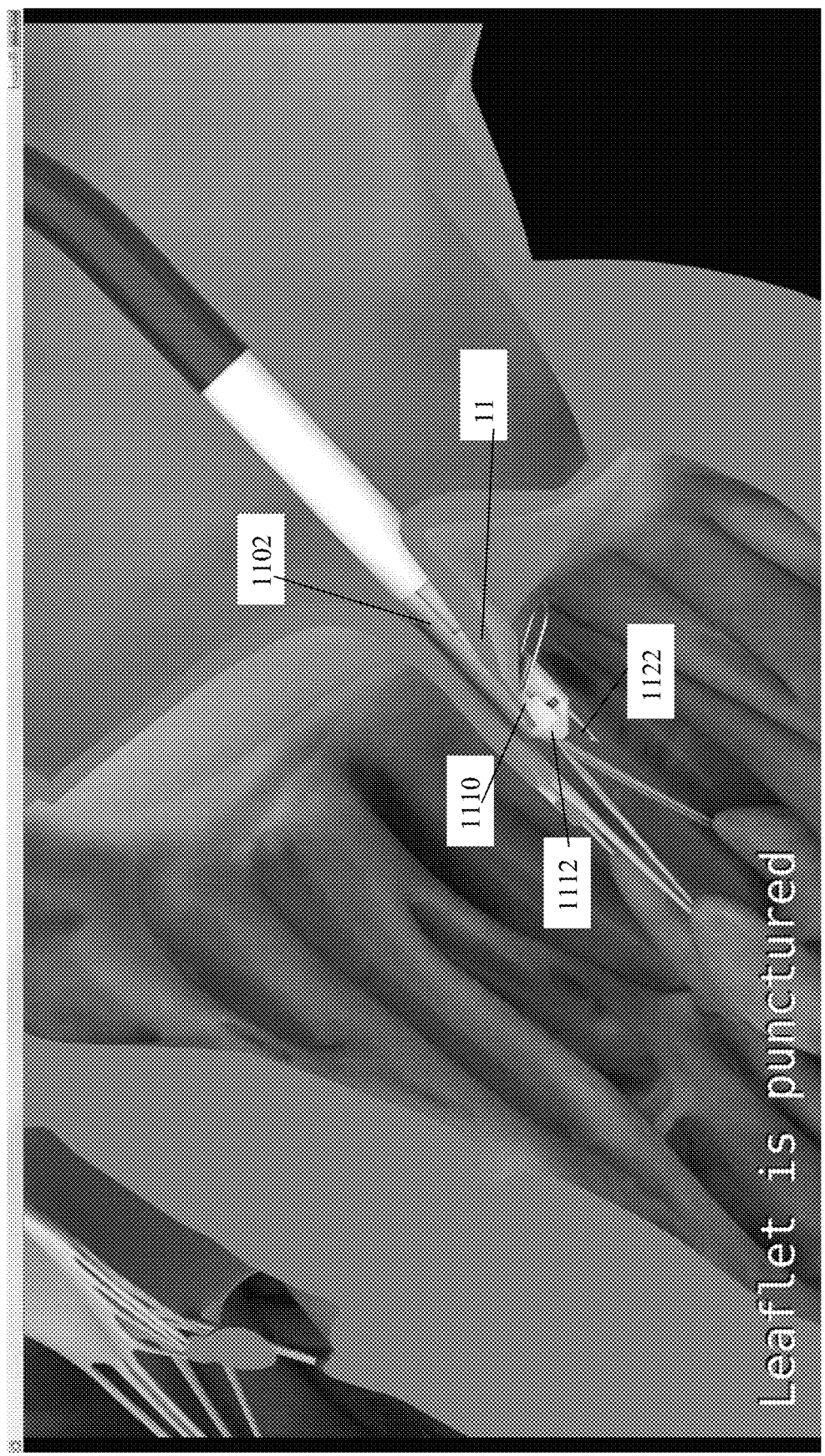
Figure 17E:
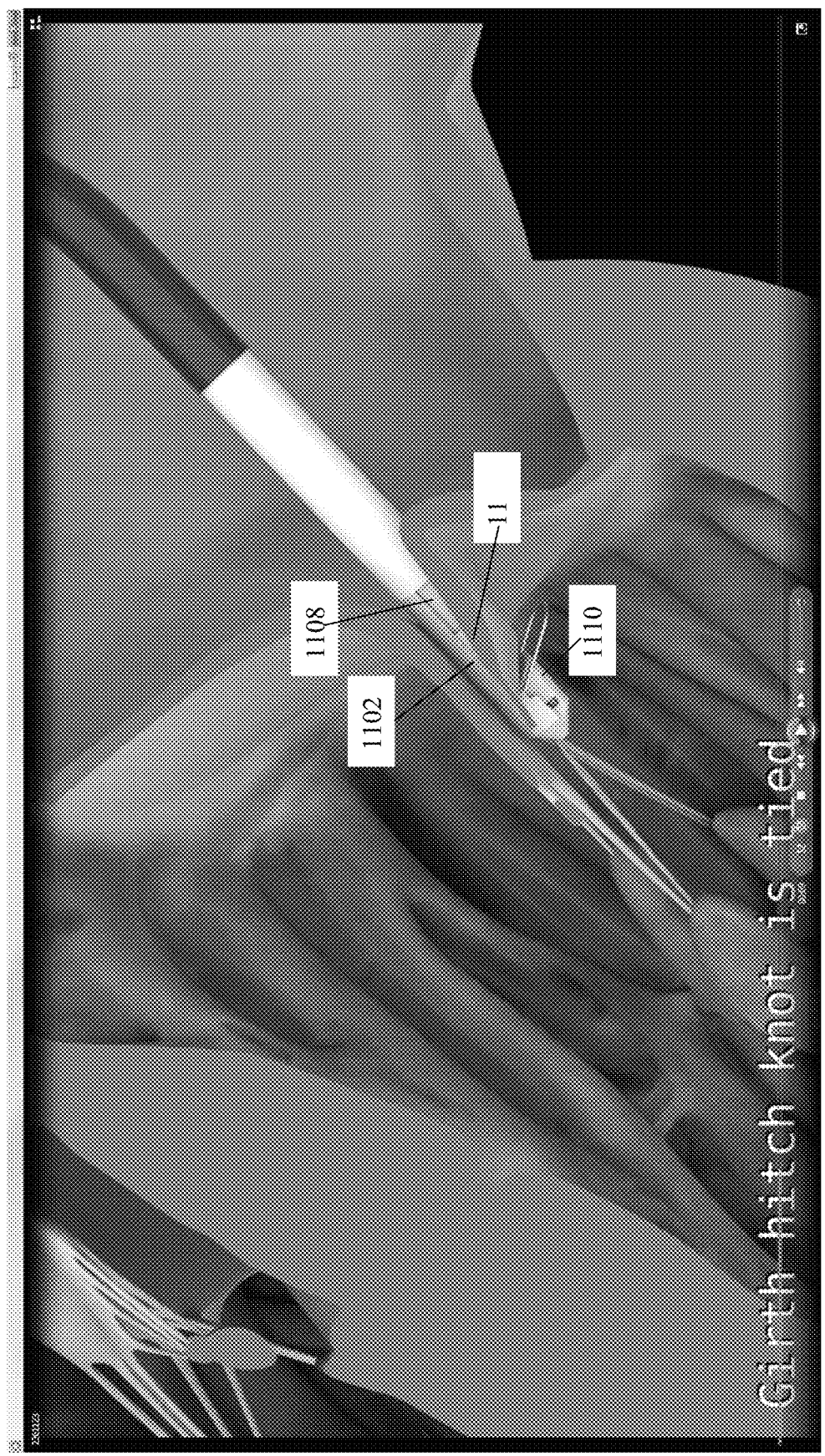
Figure 17F:
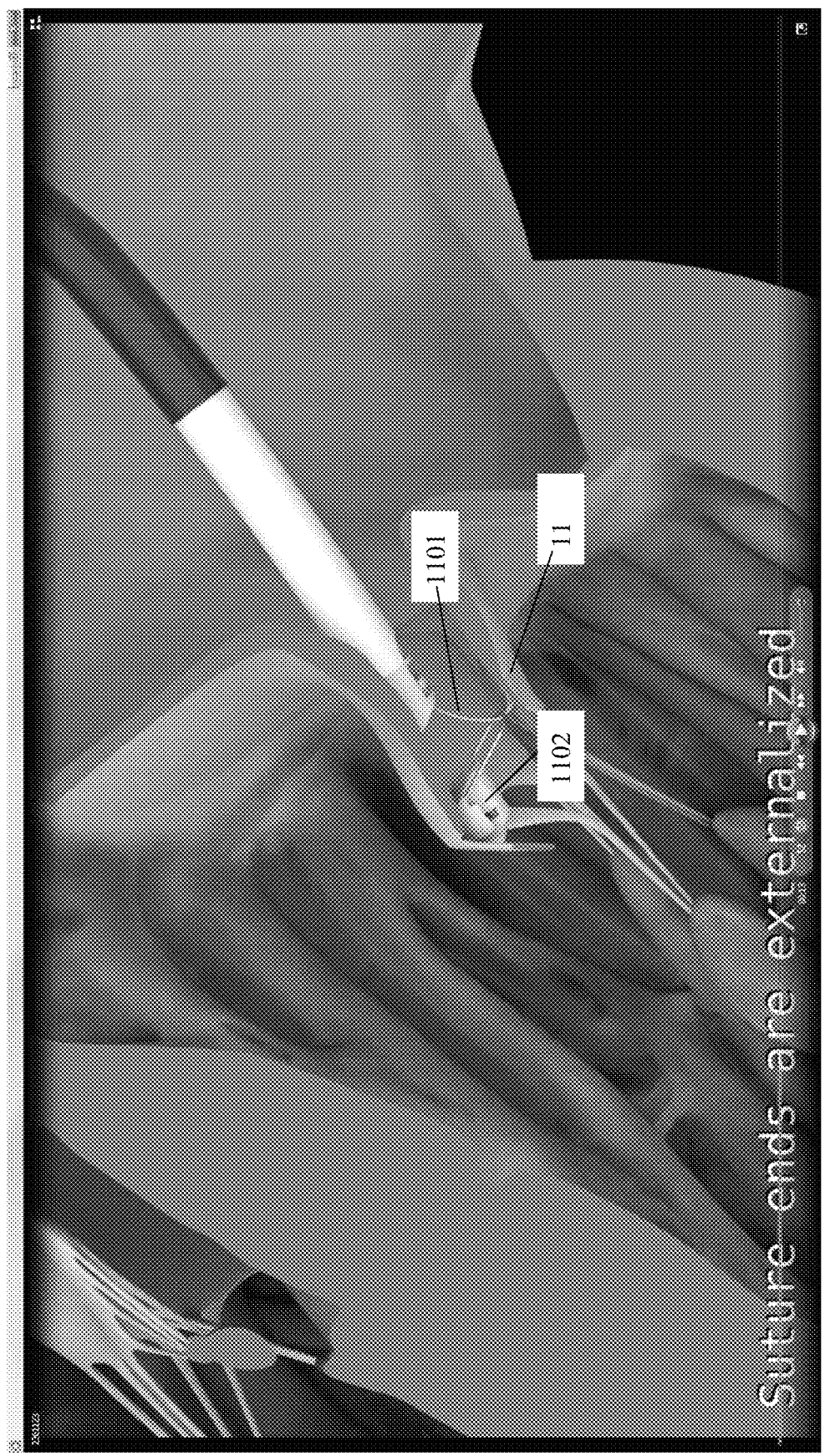
Figure 17G:
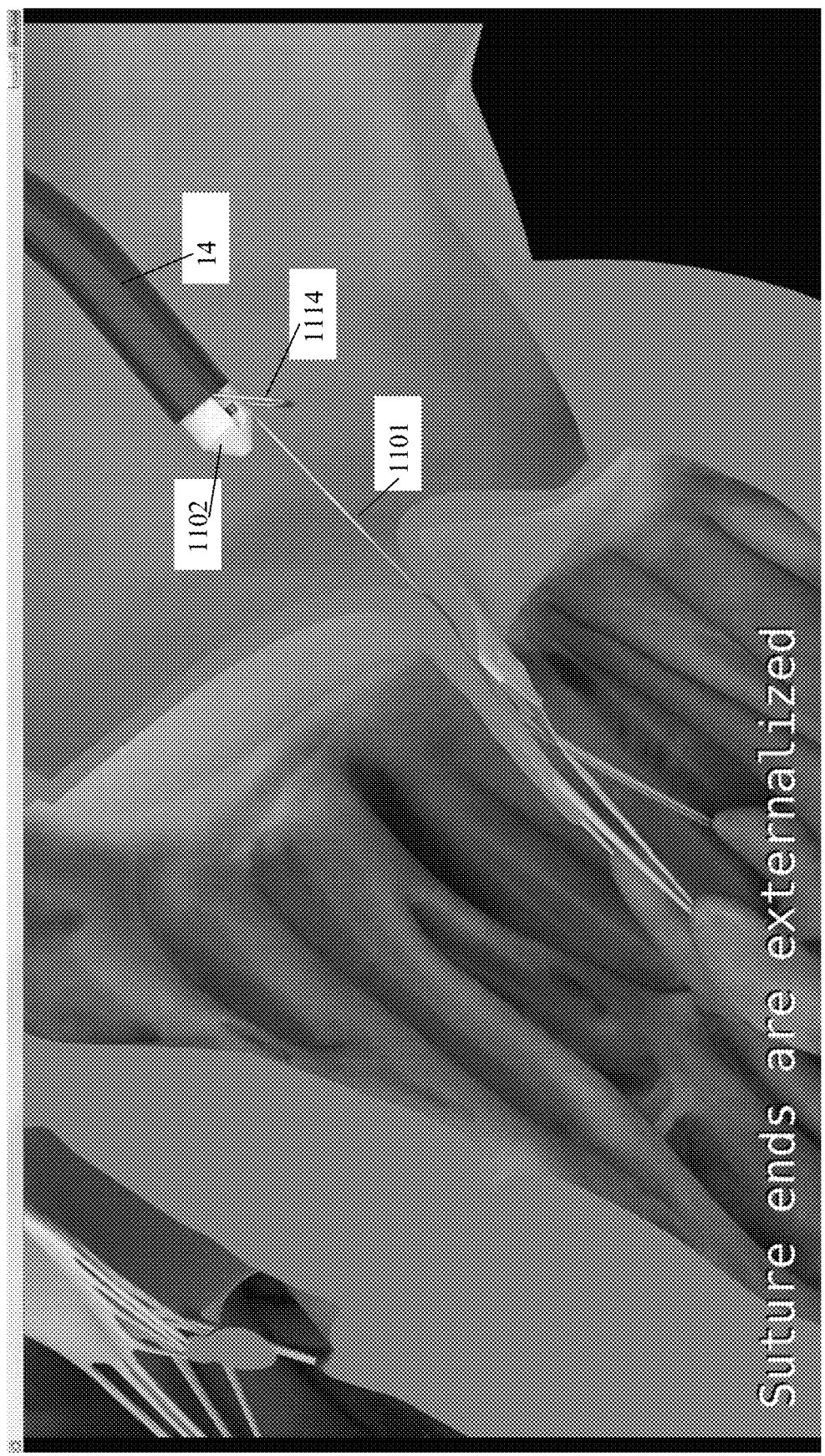

Referring now to FIG. 17D, once the leaflet 11 is firmly clamped between the jaws 1108, 1110, the needle 1122 can be actuated with the needle lever 1188 at the proximal end of the device to puncture the leaflet. The needle 1122 is then retracted through the leaflet 11 to retrieve the suture 1101 as described above. The proximal jaw 1108 can then be retracted and the distal capture assembly 1102 disengaged from the leaflet 11 with a loop of suture 1101 extending through the leaflet 11 as depicted in FIG. 17F. Distal capture assembly 1102 can then be withdrawn into the guide catheter 14. As can be seen in FIG. 17G, stabilizing loop 1114 will automatically be collapsed when contacting guide catheter 14 to conform to the shape of the leaflet capture catheter 100 to enable withdrawal of the leaflet capture catheter 1102 from the body through the guide catheter 14. Subsequently, the free ends of the suture extending from the suture loop through the leaflet can be anchored in the heart.

Although specifically described with respect to the mitral valve, it should be understood the devices described herein could be used to treat any other malfunctioning valve, such as the tricuspid and aortic valves. Further, although it should be understood that the devices described in the present application could be implanted into the beating heart of the patient via various access approaches known in the art, including transapical approaches (e.g., through the apex of the left ventricle) and transvascular approaches, such as transfemorally (through the femoral vein). One example of a transapical access approach that could be employed is described in U.S. Pat. No. 9,044,221, previously incorporated by reference herein. One example of a transvascular access approach that could be employed is described in U.S. Patent Publication No. 2013/0035757, which is hereby incorporated by reference herein. This versatility in access approach enables the access site for the procedure to be tailored to the needs of the patient.

Various embodiments of systems, devices, and methods have been described herein. These embodiments are given only by way of example and are not intended to limit the scope of the present invention. It should be appreciated, moreover, that the various features of the embodiments that have been described may be combined in various ways to produce numerous additional embodiments. Moreover, while various materials, dimensions, shapes, implantation locations, etc. have been described for use with disclosed embodiments, others besides those disclosed may be utilized without exceeding the scope of the invention.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

For purposes of interpreting the claims, it is expressly intended that the provisions of 35 U.S.C. § 112(f) are not to be invoked unless the specific terms "means for" or "step for" are recited in a claim.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

The invention claimed is:

1. A suture attachment catheter configured to repair a heart valve by inserting a suture in a valve leaflet of a beating heart of a patient, comprising:
a generally flexible catheter body having a proximal end, a distal end, and a length greater than 100 cm;
a suture attachment assembly operably attached to the distal end of the catheter body, the suture attachment assembly including:
a rail defining a portion of a clamping jaw;
a distal clamping jaw hingedly operably attached to the rail; and
a proximal clamping jaw operably attached to the rail, wherein the rail enables at least one of the proximal clamping jaw and the distal clamping jaw to be selectively slideable with respect to the other of the proximal clamping jaw and the distal clamping jaw to adjust a distance between the proximal clamping jaw and the distal clamping jaw of the clamping jaw;
a needle selectively slideable within the catheter body, the needle configured to penetrate a valve leaflet to insert a suture through the valve leaflet when the valve leaflet is captured between the proximal clamping jaw and the distal clamping jaw; and
a control handle operably attached to the proximal end of the catheter body, the control handle including:
a steering mechanism operably connected to the catheter body to selectively steer the distal end of the catheter body;
a jaw actuator operably connected to the clamping jaw; and
a needle actuator operably connected to the needle.

2. The suture attachment catheter of claim 1, wherein the distal clamping jaw is configured to pivot between a first position with respect to the rail and a second position with respect to the rail.

3. The suture attachment catheter of claim 2, wherein in the first position the distal clamping jaw is aligned generally longitudinally with respect to the rail and in the second position the distal clamping jaw is aligned generally transverse to the rail.

4. The suture attachment catheter of claim 3, wherein in the first position the distal clamping jaw is aligned at an obtuse angle with respect to the rail and in the second position the distal clamping jaw is aligned at an acute angle with respect to the rail.

5. The suture attachment catheter of claim 2, wherein the distal clamping jaw is pivoted with respect to the rail by actuation of a distal jaw control on the control handle.

6. The suture attachment catheter of claim 5, wherein the distal jaw control selectively moves a flexible member extending from the distal jaw control through the catheter body to the distal clamping jaw to pivot the distal clamping jaw.

7. The suture attachment catheter of claim 6, wherein the flexible member comprises a wire.

8. The suture attachment catheter of claim 1, further comprising a suture configured to be retrieved by the needle.

9. The suture attachment catheter of claim 8, wherein the distal clamping jaw includes one or more suture attachment features that retain the suture under tension on the distal clamping jaw in position to be caught by the needle.

10. The suture attachment catheter of claim 1, wherein the suture attachment assembly is less flexible than the catheter body.

11. The suture attachment catheter of claim 1, wherein the suture attachment catheter is configured for insertion into a left atrium of the patient's heart via a vasculature access to a right atrium of the beating heart of the patient and a transeptal access between the right atrium and a left atrium of the beating heart of the patient.

12. The suture attachment catheter of claim 1, wherein the distal clamping jaw is selectively slideable with respect to the proximal clamping jaw by sliding the rail within a channel in the proximal clamping jaw with the jaw actuator.

13. The suture attachment catheter of claim 12, further comprising a rail lock disposed in the channel, the rail lock configured to prevent the rail from being slid distally entirely out of the channel.

14. The suture attachment catheter of claim 12, where the proximal jaw is longitudinally stationary with respect to the catheter body.

15. The suture attachment catheter of claim 1, wherein the proximal clamping jaw is selectively manually slideable with respect to the distal clamping jaw.

16. The suture attachment catheter of claim 1, wherein the proximal clamping jaw is slideable by sliding the proximal clamping jaw along the rail with the jaw actuator.

17. The suture attachment catheter of claim 1, further comprising a wire loop extending from one of the proximal clamping jaw and the distal clamping jaw, the wire loop configured to effectively increase a capture area of the one of the proximal clamping jaw and the distal clamping jaw from which the wire loop extends.

18. The suture attachment catheter of claim 17, wherein the wire loop extends from the proximal clamping jaw.

19. The suture attachment catheter of claim 17, wherein the wire loop is configured to automatically transition from a collapsed position to an expanded position when the one of the proximal clamping jaw and the distal clamping jaw is extended out of a delivery catheter.

* * * * *